United States Patent
Benz et al.

(10) Patent No.: US 11,814,375 B2
(45) Date of Patent: *Nov. 14, 2023

(54) HETEROCYCLIC COMPOUNDS

(71) Applicant: Hoffmann-La Roche Inc., Little Falls, NJ (US)

(72) Inventors: Joerg Benz, Basel (CH); Luca Gobbi, Basel (CH); Uwe Grether, Basel (CH); Katrin Groebke Zbinden, Basel (CH); Benoit Hornsperger, Basel (CH); Carsten Kroll, Basel (CH); Bernd Kuhn, Basel (CH); Rainer E. Martin, Basel (CH); Fionn O'Hara, Basel (CH); Bernd Puellmann, Basel (CH); Hans Richter, Basel (CH); Martin Ritter, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 252 days.

This patent is subject to a terminal disclaimer.

(21) Appl. No.: 17/017,200

(22) Filed: Sep. 10, 2020

(65) Prior Publication Data

US 2021/0094943 A1 Apr. 1, 2021

(30) Foreign Application Priority Data

Sep. 12, 2019 (EP) .................................. 19196879

(51) Int. Cl.
| | | |
|---|---|---|
| *C07D 413/12* | (2006.01) | |
| *A61K 9/20* | (2006.01) | |
| *C07D 265/28* | (2006.01) | |
| *A61K 9/48* | (2006.01) | |

(52) U.S. Cl.
CPC .......... *C07D 413/12* (2013.01); *A61K 9/2009* (2013.01); *A61K 9/2054* (2013.01); *A61K 9/2059* (2013.01); *A61K 9/485* (2013.01); *A61K 9/4858* (2013.01); *A61K 9/4866* (2013.01); *C07D 265/28* (2013.01)

(58) Field of Classification Search
CPC .................................................. C07D 413/12
See application file for complete search history.

(56) References Cited

U.S. PATENT DOCUMENTS

| 5,214,038 A | 5/1993 | Effland et al. |
|---|---|---|
| 8,431,695 B2 | 4/2013 | O'Connor et al. |
| 10,106,556 B2 | 10/2018 | Ikeda et al. |
| 10,610,520 B2 | 4/2020 | Ikeda et al. |
| 11,390,610 B2 | 7/2022 | Benz et al. |
| 11,420,961 B2 | 8/2022 | Benz et al. |
| 2011/0251169 A1 | 10/2011 | Green et al. |
| 2014/0309218 A1 | 10/2014 | Hubschwerlen et al. |
| 2015/0018335 A1 | 1/2015 | Cisar et al. |
| 2020/0255439 A1 | 8/2020 | Kamata et al. |
| 2020/0308158 A1 | 10/2020 | Bell et al. |
| 2020/0308190 A1 | 10/2020 | Bell et al. |
| 2021/0024546 A1 | 1/2021 | Petersen et al. |
| 2021/0094943 A1 | 4/2021 | Benz et al. |
| 2021/0094971 A1 | 4/2021 | Grether et al. |
| 2021/0094972 A1 | 4/2021 | Benz et al. |
| 2021/0094973 A1 | 4/2021 | Gobbi et al. |
| 2021/0107920 A1 | 4/2021 | Bell et al. |
| 2021/0107921 A1 | 4/2021 | Benz et al. |
| 2021/0277020 A1 | 9/2021 | Anselm et al. |
| 2021/0387999 A1 | 12/2021 | Kuhn et al. |
| 2022/0098176 A1 | 3/2022 | Benz et al. |
| 2022/0106328 A1* | 4/2022 | Benz ..................... A61P 25/08 |
| 2022/0135591 A1 | 5/2022 | Benz et al. |
| 2022/0202963 A1 | 6/2022 | Collin et al. |
| 2022/0213093 A1 | 7/2022 | Benz et al. |
| 2022/0220373 A1 | 7/2022 | Benz et al. |
| 2022/0242876 A1 | 8/2022 | Kroll et al. |
| 2022/0267349 A1 | 8/2022 | Benz et al. |

(Continued)

FOREIGN PATENT DOCUMENTS

| EA | 009645 B1 | 2/2008 |
|---|---|---|
| EP | 3 279 191 A1 | 2/2018 |
| RU | 2042680 C1 | 8/1995 |

(Continued)

OTHER PUBLICATIONS

Alpar, A., et al., "Endocannabinoids modulate cortical development by configuring Slit2/Robo1 signaling" Nat Commun 5(4421):1-13 (Jul. 17, 2014).
Bernal-Chico, A., et al., "Blockade of Monoacylglycerol Lipase Inhibits Oligodendrocyte Excitotoxicity and Prevents Demyelination In Vivo" GLIA 63(1):163-176 (Jan. 1, 2015).
Chanda, P.K., et al., "Monoacylglycerol Lipase Activity Is a Critical Modulator of the Tone and Integrity of the Endocannabinoid System" Mol Pharmacol 78(6):996-1003 (Dec. 1, 2010).
Dugar, S. et al., "A Concise and Efficient Synthesis of Substituted Morpholines" Synthesis 47:712-720 (2015).

(Continued)

*Primary Examiner* — John S Kenyon
(74) *Attorney, Agent, or Firm* — Katherine J. Mackenzie

(57) ABSTRACT

The invention provides new heterocyclic compounds having the general formula (I)

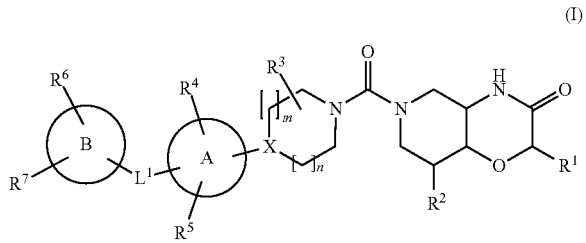

(I)

wherein A, B, L¹, X, m, n, and R¹ to R⁷ are as described herein, compositions including the compounds, processes of manufacturing the compounds and methods of using the compounds.

17 Claims, No Drawings

(56) References Cited

U.S. PATENT DOCUMENTS

2022/0275005 A1 9/2022 Grether et al.

FOREIGN PATENT DOCUMENTS

| WO | 2005/019215 | A1 | 3/2005 | |
|----|---|---|---|---|
| WO | 2005/066187 | A1 | 7/2005 | |
| WO | 2007/002057 | A1 | 1/2007 | |
| WO | 2007/098418 | A1 | 8/2007 | |
| WO | 2007/117557 | A2 | 10/2007 | |
| WO | 2009/097287 | A1 | 8/2009 | |
| WO | 2010/049302 | | 5/2010 | |
| WO | 2011/058766 | A1 | 5/2011 | |
| WO | 2011/059118 | A1 | 5/2011 | |
| WO | 2012/155199 | A1 | 11/2012 | |
| WO | 2013/059118 | A1 | 4/2013 | |
| WO | 2013/093849 | A1 | 6/2013 | |
| WO | 2013/179024 | A1 | 12/2013 | |
| WO | 2014/102630 | A1 | 7/2014 | |
| WO | 2014/170821 | A1 | 10/2014 | |
| WO | 2016/109501 | A1 | 7/2016 | |
| WO | 2016/180536 | A1 | 11/2016 | |
| WO | 2016/185279 | A1 | 11/2016 | |
| WO | 2016/205590 | A1 | 12/2016 | |
| WO | 2017/087858 | A1 | 5/2017 | |
| WO | 2017/087863 | A1 | 5/2017 | |
| WO | 2017/171100 | A1 | 10/2017 | |
| WO | 2018/228934 | A1 | 12/2018 | |
| WO | 2019/072785 | A1 | 4/2019 | |
| WO | 2019/105915 | A1 | 6/2019 | |
| WO | 2019/115660 | A1 | 6/2019 | |
| WO | 2019/134985 | A1 | 7/2019 | |
| WO | 2019/180185 | A1 | 9/2019 | |
| WO | WO-2019180185 | A1 * | 9/2019 | ......... A61K 31/5383 |
| WO | 2020/035424 | A1 | 2/2020 | |
| WO | 2020/035425 | A1 | 2/2020 | |
| WO | 2020/103815 | | 5/2020 | |
| WO | 2020/104494 | A1 | 5/2020 | |

OTHER PUBLICATIONS

Feliu, A., et al., "2-Arachidonoylglycerol Reduces Proteoglycans and Enhances Remyelination in a Progressive Model of Demyelination" J Neurosci 37(35):8385-8398 (Aug. 30, 2017).
Iannotti, F. A., et al., "Endocannabinoids and endocannabinoid-related mediators: Targets metabolism and role in neurological disorders" Prog Lipid Res 62:107-128 (Apr. 1, 2016).
Ignatowska-Jankowska, B., et al., "Selective Monoacylglycerol Lipase Inhibitors: Antinociceptive versus Cannabimimetic Effects in Mice" J Pharmacol Exp Ther 353(2):424-432 (May 1, 2015).
International Search Report and Written Opinion for PCT/EP2020/075260 dated Nov. 18, 2020.
Lleo, A., et al., "Molecular targets of non-steroidal anti-inflammatory drugs in neurodegenerative diseases" Cell Mol Life Sci 64(11):1403-1418 (Apr. 20, 2007).
Long, J.Z., et al., "Selective blockade of 2-arachidonoylglycerol hydrolysis produces cannabinoid behavioral effects" Nat Chem Biol 5(1):37-44 (Nov. 23, 2008).
Nomura, D.K., et al., "Endocannabinoid Hydrolysis Generates Brain Prostaglandins That Promote Neuroinflammation" Science 334(6057):809-813 (Nov. 11, 2011).
Nomura, D.K., et al., "Monoacylglycerol Lipase Exerts Dual Control over Endocannabinoid and Fatty Acid Pathways to Support Prostate Cancer" Chem Biol 18(7):846-856 (Jul. 29, 2011).
Nomura, D.K., et al., "Monoacylglycerol Lipase Regulates a Fatty Acid Network that Promotes Cancer Pathogenesis" Cell 140(1):49-61 (Jan. 8, 2010).
Qin, H., et al., "The role of monoacylglycerol lipase (MAGL) in the cancer progress" Cell Biochem Biophys 70:33-36 (Mar. 16, 2014).
Rafinski, Z. et al., "Enantioselective Synthesis of Chromanones Beating Quaternary Substituted Stereocenters Catalyzed by (1R)-Camphor-Derived N-Heterocyclic Carbenes" J. Org. Chem. 80:7468-7476 (2015).

U.S. Appl. No. 16/827,211, filed Mar. 23, 2020.
U.S. Appl. No. 16/844,262, filed Aug. 12, 2019.
U.S. Appl. No. 16/884,562, filed May 27, 2020.
U.S. Appl. No. 16/899,928 J, filed Jun. 12, 2020.
U.S. Appl. No. 16/922,427, filed Jul. 7, 2020.
U.S. Appl. No. 17/012,589, filed Sep. 4, 2020.
U.S. Appl. No. 17/025,155, filed Sep. 18, 2020.
U.S. Appl. No. 17/026,619, filed Sep. 21, 2020.
U.S. Appl. No. 17/027,952, filed Sep. 22, 2020.
U.S. Appl. No. 17/027,976, filed Sep. 22, 2020.
Viader, A., et al., "Metabolic Interplay between Astrocytes and Neurons Regulates Endocannabinoid Action" Cell Rep 12(5):798-808 (Aug. 4, 2015).
Yin, J., et al., "ARSZ/MAGL signaling in glioblastoma stem cells promotes self-renewal and M2-like polarization of tumor-associated macrophages" Nat Commun 11(1 Suppl 2978):1-15 (Jun. 11, 2020).
Zhong, P., et al., "Monoacylglycerol Lipase Inhibition Blocks Chronic Stress-Induced Depressive-Like Behaviors via Activation of mTOR Signaling" Neuropsychopharmacology 39(7):1763-1776 (Feb. 19, 2014).
Anderson, A.C., "The Process of Structure-Based Drug Design" Chem Biol 10(9):787-797 (Sep. 1, 2003).
Ashton, K., et al., "Design and synthesis of novel amide AKT1 inhibitors with selectivity over CDK2" Bioorg Med Chem Lett 21(18):5191-5196 (Sep. 15, 2011).
Barney, C., et al., "A convenient synthesis of hindered amines and α-trifluoromethylamines from ketones" Tetrahedron Lett 31(39):5547-5550 (1990).
Belikov, V.G. Pharmaceutical Chemistry—Tutorial "Part I: General Pharmaceutical Chemistry" (Extract—Eng. Translation), Fourth, Revised edition, Moscow—RU:MEDPress-Inform,:27-29 (2007).
Chang, J. et al., "Highly Selective Inhibitors of Monoacylglycerol Lipase Bearing a Reactive Group that is Bio-isosteric with Endocannabinoid Substrates" Chem Biol 19(5):579-588 (May 1, 2012).
Cisar, J., et al., "Identification of ABX-1431, a Selective Inhibitor of Monoacylglycerol Lipase and Clinical Candidate for Treatment of Neurological Disorders" ACS J Med Chem 61(20):9062-9084 (Aug. 1, 2018).
Damasio, A., "Alzheimer's Disease and Related Dementias" Cecil Textbook of Medicine 20(2):1992-1996 (Jan. 1, 1996).
Duncan, M., et al., "Review article: endocannabinoids and their receptors in the enteric nervous system" Aliment Pharmacol Ther 22(8):667-683 (Oct. 15, 2005).
Durnov and Goldbenko, "Children's Oncology" Medicine, : 139 (2002), (English machine translation).
Evano, G., et al., "Copper-Mediated Coupling Reactions and Their Applications in Natural Products and Designed Biomolecules Synthesis" Chem Rev 108(8):3054-3131 (Aug. 13, 2008).
Fray, M., et al., "Second generation N-(1,2-diphenylethyl)piperazines as dual serotonin and noradrenaline reuptake inhibitors: improving metabolic stability and reducing ion channel activity" Bioorg Med Chem Lett 20(12):3788-3792 (Jun. 15, 2010).
Fray, M., et al., "Structure-activity relationships of N-substituted piperazine amine reuptake inhibitors" Bioorg Med Chem Lett 16(16):4349-4353 (Aug. 15, 2006).
Gavryushin, A., et al., "Efficient Cross-Coupling of Functionalized Arylzinc Halides Catalyzed by a Nickel Chloride-Diethyl Phosphite System" Org Lett 7(22):4871-4874 (Oct. 7, 2005).
Grill, M., et al., "Members of the endocannabinoid system are distinctly regulated in inflammatory bowel disease and colorectal cancer" Sci Rep 9(2358):1-13 (Feb. 20, 2019).
Gura, T., "Systems for Identifying New Drugs Are Often Faulty" Science 278(5340):1041-1042 (Nov. 7, 1997).
Haas, D., et al., "Recent Developments in Negishi Cross-Coupling Reactions" ACS Catal 6(3):1540-1552 (Feb. 3, 2016).
He, S., et al., "High-Affinity Small-Molecule Inhibitors of the Menin-Mixed Lineage Leukemia (MLL) Interaction Closely Mimic a Natural Protein-Protein Interaction" J Med Chem 57(4):1543-1556 (Feb. 27, 2014).
Heravi, M., et al., "Buchwald-Hartwig reaction: An overview" J Organometallic Chem 861:17-104 (Apr. 15, 2018).

(56) References Cited

OTHER PUBLICATIONS

Hutchings, K., et al., "Synthesis and antibacterial activity of the C-7 side chain of 3-aminoquinazolinediones" Bioorg Med Chem Lett 18(18):5087-5090 (Sep. 15, 2008).
"International Preliminary Report on Patentability—PCT/EP2019/081870" (Report dated May 25, 2021; Chapter I), pp. 1-8 (Jun. 3, 2021).
"International Preliminary Report on Patentability—PCT/EP2019/071520" (Report dated Feb. 16, 2021, Chapter I),:pp. 1-8 (Feb. 25, 2021).
"International Preliminary Report on Patentability—PCT/EP2019/057174" (Report dated Sep. 22, 2020—Chapter I),:pp. 1-9 (Oct. 1, 2020).
"International Preliminary Report on Patentability—PCT/EP2019/071522" (Report dated Feb. 16, 2021, Chapter I),:pp. 1-9 (Feb. 25, 2021).
"International Preliminary Report on Patentability—PCT/EP2020/076346" (Report dated Mar. 15, 2022; Chapter I),:pp. 1-9 (Apr. 7, 2022).
"International Preliminary Report on Patentability—PCT/EP2020/074897" (Report dated Mar. 9, 2022; Chapter I),:pp. 1-8 (Mar. 17, 2022).
"International Preliminary Report on Patentability—PCT/EP2020/076228" (Report dated Mar. 15, 2022; Chapter I),:pp. 1-9 (Apr. 7, 2022).
"International Search Report—PCT/EP2019/057174" (w/Written Opinion),:pp. 1-14 (dated Jul. 3, 2019).
"International Search Report—PCT/EP2019/071520" (w/Written Opinion),:pp. 1-14 (dated Sep. 17, 2019).
"International Search Report—PCT/EP2019/071522" (w/Written Opinion),:pp. 1-15 (dated Sep. 17, 2019).
"International Search Report—PCT/EP2019/081870" (w/Written Opinion),:pp. 1-12 (dated Jan. 14, 2020).
"International Search Report—PCT/EP2020/074897" (w/Written Opinion),:pp. 1-15 (dated Nov. 18, 2020).
"International Search Report—PCT/EP2020/076228" (w/Written Opinion),:pp. 1-14 (dated Nov. 12, 2020).
"International Search Report—PCT/EP2020/076346" (w/Written Opinion),:pp. 1-16 (dated Nov. 13, 2020).
"International Search Report—PCT/EP2020/076347" (w/Written Opinion),:pp. 1-16 (dated Nov. 30, 2020).
Ishichi, Y., et al., "Novel triple reuptake inhibitors with low risk of CAD associated liabilities: design, synthesis and biological activities of 4-[(1S)-1-(3,4-dichlorophenyl)-2-methoxyethyl]piperidine and related compounds" Bioorg Med Chem 21(15):4600-4613 (Aug. 1, 2013).
Janssen, F., et al., "Inhibitors of diacylglycerol lipases in neurodegenerative and metabolic disorders" Bioorg Med Chem Lett 26(16):3831-3837 (Aug. 15, 2016).
Johnson, J.I., et al., "Relationships between drug activity in NCI preclinical in vitro and in vivo models and early clinical trials" Brit J Cancer 84(10):1424-1431 (May 1, 2001).
Keenan, M., et al., "Design, structure-activity relationship and in vivo efficacy of piperazine analogues of fenarimol as inhibitors of Trypanosoma cruzi" Bioorg Med Chem 21(7):1756-1763 (Apr. 1, 2013).
Kitbunnadaj, R., et al., "Synthesis and structure-activity relationships of conformationally constrained histamine H(3) receptor agonists" J Med Chem 46(25):5445-5457 (Dec. 4, 2003).
Kummerer, K., "Pharmaceuticals in the Environment" Ann Rev Environ Res 35:57-75 (Nov. 1, 2010).
Layzer, R., "Section Five: Degenerative Diseases of the Nervous System" Cecil Textbook of Medicine 20(2):2050-2057 (Jan. 1, 1996).
Liu, F., et al., "Structure-Based Optimization of Pyridoxal 5'-Phosphate-Dependent Transaminase Enzyme (BioA) Inhibitors that Target Biotin Biosynthesis in *Mycobacterium tuberculosis*" J Med Chem 60(13):5507-5520 (Jul. 13, 2017).
Liu, Y. et al., "Discovery of 4-benzoylpiperidine and 3-(piperidin-4-yl)benzo[d]isoxazole derivatives as potential and selective GlyT1 inhibitors" RSC Adv 5(51):40964-40977 (Apr. 30, 2015).
Marquez, L., et al., "Ulcerative Colitis Induces Changes on the Expression of the Endocannabinoid System in the Human Colonic Tissue" PLOS One 4(9):e6893 (1-13) (Sep. 4, 2009).
McAllister, L., et al., "Discovery of Trifluoromethyl Glycol Carbamates as Potent and Selective Covalent Monoacylglycerol Lipase (MAGL) Inhibitors for Treatment of Neuroinflammation" J Med Chem 61(7):3008-3026 (Apr. 12, 2018).
Merck Manual et al. Merck Manual—Online Professional "Acute Leukemia" Kenilworth, N.J.—USA:Merck and Company, Inc.,:1-6 (Jul. 10, 2013).
Muccioli, G., et al., "CAY10499, a Novel Monoglyceride Lipase Inhibitor Evidenced by an Expeditious MGL Assay" Chem Bio Chem 9(16):2704-2710 (Nov. 3, 2008).
Mulvihill, M., et al., "Therapeutic Potential of Monoacylglycerol Lipase Inhibitors" Life Sci 92(8-9):492-497 (Nov. 8, 2013).
Negishi, E., "Palladium- or Nickel-Catalyzed Cross Coupling. A New Selective Method for Carbon-Carbon Bond Formation" Acc Chem Res 15(11):340-348 (Nov. 1, 1982).
Patel, J. et al., "Loratadine analogues as MAGL inhibitors" Bioorg Med Chem Lett 25(7):1436-1442 (Feb. 24, 2015).
Pearce, H., et al. Cancer Drug Design and Discovery "Chapter 18: Failure modes in anticancer drug discovery and development" Neidle, S., ed., 1st edition, New York, NY—USA:Academic Presss,:424-435 ( 2008).
Perisetti, A., et al., "Role of cannabis in inflammatory bowel diseases" Ann Gastroenterol 33(2):134-144 (Feb. 12, 2020).
Scalvini, L., et al., "Monoglyceride lipase: Structure and inhibitors" Chem Phys Lipids 197:13-24 (Jul. 26, 2015).
Senter, T., et al., "Progress towards small molecule menin-mixed lineage leukemia (MLL) interaction inhibitors with in vivo utility" Bioorg Med Chem Lett 25(13):2720-2725 (Jul. 1, 2015).
Simone, J.V,, "Oncology: Introduction" Cecil Textbook of Medicine 1(20):1004-1010 (Jan. 1, 1996).
Surry, D., et al., "Biaryl Phosphane Ligands in Palladium-Catalyzed Amination" Angew Chem Int Ed Engl 47(34):6338-6361 (Aug. 11, 2008).
Thiel, K.,, "Structure-aided drug design's next generation" Nat Biotechnol 22(5):513-519 (May 1, 2004).
"U.S. Appl. No. 17/749,496, filed May 20, 2022".
U.S. Appl. No. 17/818,459, filed Aug. 9.
Ukrorgsyntez, Ltd., CAS Registry Database, 1941372-36-6, (Stereosearch—C20 H27 N3 03), pp. 1Creation Date Jun. 29, 2016.
Walsh, D., et al., "Synthesis and antiallergy activity of 4-(diarylhydroxymethyl)-1-[3-(aryloxy)propyl]piperidines and structurally related compounds" J Med Chem 32(1):105-118 (Jan. 1, 1989).
Wang, J., et al., "Effect of monoacylglycerol lipase inhibition on intestinal permeability in chronic stress model" Biochem Biophys Res Commun 525(4):962-967 (May 14, 2020).
Williams, D., et al. Foye's Principles of Medicinal Chemistry, Chapter 2(5th edition):59-63 (2002).
Wright, K., et al., "Differential expression of cannabinoid receptors in the human colon: cannabinoids promote epithelial wound healing" Gastroenterology 129(2):437-453 (Aug. 1, 2005).
"Written Opinion of the International Searching Authority—PCT/EP2019/071520":pp. 1-6 (dated Sep. 17, 2019).
Wu, W., et al., "Synthesis and structure-activity relationships of piperidine-based melanin-concentrating hormone receptor 1 antagonists" Bioorg Med Chem Lett 16(14):3668-3673 (Jul. 15, 2006).
Zhang, P., et al., "Silyl Radical Activation of Alkyl Halides in Metallaphotoredox Catalysis: A Unique Pathway for Cross-Electrophile Coupling" J Am Chem Soc 138(26):8084-8087 (Jul. 6, 2016).
Zhang, X., et al., "Direct Aldehyde C-H Arylation and Alkylation via the Combination of Nickel, Hydrogen Atom Transfer, and Photoredox Catalysis" J Am Chem Soc 139(33):11353-11356 (Aug. 23, 2017).

* cited by examiner

HETEROCYCLIC COMPOUNDS

CROSS-REFERENCE TO RELATED APPLICATIONS

This application claims priority to EP Application No. 19196879.1, filed Sep. 12, 2019, the disclosure of which is incorporated herein by reference in its entirety.

FIELD OF THE INVENTION

The present invention relates to organic compounds useful for therapy or prophylaxis in a mammal, and in particular to monoacylglycerol lipase (MAGL) inhibitors for the treatment or prophylaxis of neuroinflammation, neurodegenerative diseases, pain, cancer, mental disorders, multiple sclerosis, Alzheimer's disease, Parkinson's disease, amyotrophic lateral sclerosis, traumatic brain injury, neurotoxicity, stroke, epilepsy, anxiety, migraine, depression, inflammatory bowel disease, abdominal pain, abdominal pain associated with irritable bowel syndrome and/or visceral pain in a mammal.

BACKGROUND OF THE INVENTION

Endocannabinoids (ECs) are signaling lipids that exert their biological actions by interacting with cannabinoid receptors (CBRs), CB1 and CB2. They modulate multiple physiological processes including neuroinflammation, neurodegeneration and tissue regeneration (Iannotti, F. A., et al., *Progress in lipid research* 2016, 62, 107-28). In the brain, the main endocannabinoid, 2-arachidonoylglycerol (2-AG), is produced by diacyglycerol lipases (DAGL) and hydrolyzed by the monoacylglycerol lipase, MAGL. MAGL hydrolyses 85% of 2-AG; the remaining 15% being hydrolysed by ABHD6 and ABDH12 (Nomura, D. K., et al., *Science* 2011, 334, 809). MAGL is expressed throughout the brain and in most brain cell types, including neurons, astrocytes, oligodendrocytes and microglia cells (Chanda, P. K., et al., *Molecular pharmacology* 2010, 78, 996; Viader, A., et al., *Cell reports* 2015, 12, 798). 2-AG hydrolysis results in the formation of arachidonic acid (AA), the precursor of prostaglandins (PGs) and leukotrienes (LTs). Oxidative metabolism of AA is increased in inflamed tissues. There are two principal enzyme pathways of arachidonic acid oxygenation involved in inflammatory processes, the cyclo-oxygenase which produces PGs and the 5-lipoxygenase which produces LTs. Of the various cyclooxygenase products formed during inflammation, PGE2 is one of the most important. These products have been detected at sites of inflammation, e.g. in the cerebrospinal fluid of patients suffering from neurodegenerative disorders and are believed to contribute to inflammatory response and disease progression. Mice lacking MAGL (Mgll−/−) exhibit dramatically reduced 2-AG hydrolase activity and elevated 2-AG levels in the nervous system while other arachidonoyl-containing phospho- and neutral lipid species including anandamide (AEA), as well as other free fatty acids, are unaltered. Conversely, levels of AA and AA-derived prostaglandins and other eicosanoids, including prostaglandin E2 (PGE2), D2 (PGD2), F2 (PGF2), and thromboxane B2 (TXB2), are strongly decreased. Phospholipase $A_2$ ($PLA_2$) enzymes have been viewed as the principal source of AA, but $cPLA_2$-deficient mice have unaltered AA levels in their brain, reinforcing the key role of MAGL in the brain for AA production and regulation of the brain inflammatory process.

Neuroinflammation is a common pathological change characteristic of diseases of the brain including, but not restricted to, neurodegenerative diseases (e.g. multiple sclerosis, Alzheimer's disease, Parkinson disease, amyotrophic lateral sclerosis, traumatic brain injury, neurotoxicity, stroke, epilepsy and mental disorders such as anxiety and migraine). In the brain, production of eicosanoids and prostaglandins controls the neuroinflammation process. The pro-inflammatory agent lipopolysaccharide (LPS) produces a robust, time-dependent increase in brain eicosanoids that is markedly blunted in Mgll−/− mice. LPS treatment also induces a widespread elevation in pro-inflammatory cytokines including interleukin-1-a (IL-1-a), IL-1b, IL-6, and tumor necrosis factor-a (TNF-α) that is prevented in Mgll−/− mice.

Neuroinflammation is characterized by the activation of the innate immune cells of the central nervous system, the microglia and the astrocytes. It has been reported that anti-inflammatory drugs can suppress in preclinical models the activation of glia cells and the progression of disease including Alzheimer's disease and multiple sclerosis (Lleo A., *Cell Mol Life Sci.* 2007, 64, 1403). Importantly, genetic and/or pharmacological disruption of MAGL activity also blocks LPS-induced activation of microglial cells in the brain (Nomura, D. K., et al., *Science* 2011, 334, 809).

In addition, genetic and/or pharmacological disruption of MAGL activity was shown to be protective in several animal models of neurodegeneration including, but not restricted to, Alzheimer's disease, Parkinson's disease and multiple sclerosis. For example, an irreversible MAGL inhibitor has been widely used in preclinical models of neuroinflammation and neurodegeneration (Long, J. Z., et al., *Nature chemical biology* 2009, 5, 37). Systemic injection of such inhibitor recapitulates the Mgll−/− mice phenotype in the brain, including an increase in 2-AG levels, a reduction in AA levels and related eicosanoids production, as well as the prevention of cytokines production and microglia activation following LPS-induced neuroinflammation (Nomura, D. K., et al., *Science* 2011, 334, 809), altogether confirming that MAGL is a druggable target.

Consecutive to the genetic and/or pharmacological disruption of MAGL activity, the endogenous levels of the MAGL natural substrate in the brain, 2-AG, are increased. 2-AG has been reported to show beneficial effects on pain with, for example, anti-nociceptive effects in mice (Ignatowska-Jankowska B. et al., *J Pharmacol. Exp. Ther.* 2015, 353, 424) and on mental disorders, such as depression in chronic stress models (Zhong P. et al., *Neuropsychopharmacology* 2014, 39, 1763).

Furthermore, oligodendrocytes (OLs), the myelinating cells of the central nervous system, and their precursors (OPCs) express the cannabinoid receptor 2 (CB2) on their membrane. 2-AG is the endogenous ligand of CB1 and CB2 receptors. It has been reported that both cannabinoids and pharmacological inhibition of MAGL attenuate OLs's and OPCs's vulnerability to excitotoxic insults and therefore may be neuroprotective (Bernal-Chico, A., et al., *Glia* 2015, 63, 163). Additionally, pharmacological inhibition of MAGL increases the number of myelinating OLs in the brain of mice, suggesting that MAGL inhibition may promote differentiation of OPCs in myelinating OLs in vivo (Alpar, A., et al., *Nature communications* 2014, 5, 4421). Inhibition of MAGL was also shown to promote remyelination and functional recovery in a mouse model of progressive multiple sclerosis (Feliu A. et al., *Journal of Neuroscience* 2017, 37 (35), 8385).

In addition, in recent years, metabolism is talked highly important in cancer research, especially the lipid metabolism. Researchers believe that the de novo fatty acid synthesis plays an important role in tumor development. Many studies illustrated that endocannabinoids have anti-tumorigenic actions, including anti-proliferation, apoptosis induction and anti-metastatic effects. MAGL as an important decomposing enzyme for both lipid metabolism and the endocannabinoids system, additionally as a part of a gene expression signature, contributes to different aspects of tumourigenesis, including in glioblastoma (Qin, H., et al., *Cell Biochem. Biophys.* 2014, 70, 33; Nomura D K et al., *Cell* 2009,140(1), 49-61; Nomura D K et al., *Chem. Biol.* 2011, 18(7), 846-856, Jinlong Yin et al, *Nature Communications* 2020, 11, 2978).

The endocannabinoid system is also involved in many gastrointestinal physiological and physiopathological actions (Marquez, Suarez et al. 2009). All these effects are driven mainly via cannabinoid receptors (CBRs), CB1 and CB2. CB1 receptors are present throughout the GI tract of animals and healthy humans, especially in the enteric nervous system (ENS) and the epithelial lining, as well as smooth muscle cells of blood vessels in the colonic wall (Wright, Rooney et al. 2005), (Duncan, Davison et al. 2005). Activation of CB1 produces anti-emetic, anti-motility, and anti-inflammatory effect, and help to modulate pain (Perisetti, Rimu et al. 2020). CB2 receptors are expressed in immune cells such as plasma cells and macrophages, in the lamina propria of the GI tract (Wright, Rooney et al. 2005), and primarily on the epithelium of human colonic tissue associated with inflammatory bowel disease (IBD). Activation of CB2 exerts anti-inflammatory effect by reducing pro-inflammatory cytokines. Expression of MAGL is increased in colonic tissue in UC patients (Marquez, Suarez et al. 2009) and 2-AG levels are increased in plasma of IBD patients (Grill, Hogenauer et al. 2019). Several animal studies have demonstrated the potential of MAGL inhibitors for symptomatic treatment of IBD. MAGL inhibition prevents TNBS-induced mouse colitis and decreases local and circulating inflammatory markers via a CB1/CB2 MoA (Marquez, Suarez et al. 2009). Furthermore, MAGL inhibition improves gut wall integrity and intestinal permeability via a CBT driven MoA (Wang, Zhang et al. 2020).

In conclusion, suppressing the action and/or the activation of MAGL is a promising new therapeutic strategy for the treatment or prevention of neuroinflammation, neurodegenerative diseases, pain, cancer, mental disorders, inflammatory bowel disease, abdominal pain and abdominal pain associated with irritable bowel syndrome. Furthermore, suppressing the action and/or the activation of MAGL is a promising new therapeutic strategy for providing neuroprotection and myelin regeneration. Accordingly, there is a high unmet medical need for new MAGL inhibitors.

SUMMARY OF THE INVENTION

In a first aspect, the present invention provides compounds of formula (I)

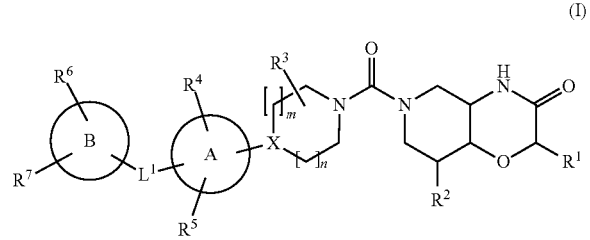

(I)

wherein A, B, $L^1$, X, m, n, and $R^1$ to $R^7$ are as defined herein.

In a further aspect, the present invention provides a process of manufacturing the compounds of formula (I) as described herein, or pharmaceutically acceptable salts thereof, comprising:

reacting 4a,5,6,7,8,8a-hexahydro-4H-pyrido[4,3-b][1,4] oxazin-3-ones 1, wherein $R^1$ and $R^2$ are as defined herein,

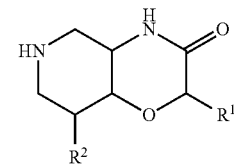

1 with a heterocyclic amine 2, wherein A, B, $L^1$, X, m, n, and $R^3$ to $R^7$ are as defined herein

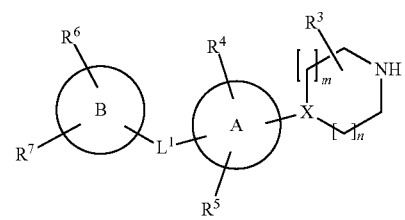

2 in the presence of a base and a urea forming reagent, to form said compounds of formula (I) or pharmaceutically acceptable salts thereof.

In a further aspect, the present invention provides a compound of formula (I) as described herein, or a pharmaceutically acceptable salt thereof, when manufactured according to the processes described herein.

In a further aspect, the present invention provides a compound of formula (I) as described herein, or a pharmaceutically acceptable salt thereof, for use as therapeutically active substance.

In a further aspect, the present invention provides a pharmaceutical composition comprising a compound of formula (I) as described herein, or a pharmaceutically acceptable salt thereof, and a therapeutically inert carrier.

In a further aspect, the present invention provides a compound of formula (I) as described herein, or a pharmaceutically acceptable salt thereof, for use in a method of inhibiting monoacylglycerol lipase in a mammal.

In a further aspect, the present invention provides a compound of formula (I) as described herein, or a pharmaceutically acceptable salt thereof, for use in the treatment or prophylaxis of neuroinflammation, neurodegenerative diseases, pain, cancer and/or mental disorders in a mammal.

In a further aspect, the present invention provides a compound of formula (I) as described herein, or a pharmaceutically acceptable salt thereof, for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

DETAILED DESCRIPTION OF THE INVENTION

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" refers to a mono- or multivalent, e.g., a mono- or bivalent, linear or branched saturated hydrocarbon group of 1 to 12 carbon atoms. In some preferred embodiments, the alkyl group contains 1 to 6 carbon atoms ("$C_{1-6}$-alkyl"), e.g., 1, 2, 3, 4, 5, or 6 carbon atoms. In other embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. Particularly preferred, yet non-limiting examples of alkyl are methyl and 2,2-dimethylpropyl. The term "alkoxy" refers to an alkyl group, as previously defined, attached to the parent molecular moiety via an oxygen atom. Unless otherwise specified, the alkoxy group contains 1 to 12 carbon atoms. In some preferred embodiments, the alkoxy group contains 1 to 6 carbon atoms ("$C_{1-6}$-alkoxy"). In other embodiments, the alkoxy group contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy and tert-butoxy. A particularly preferred, yet non-limiting example of alkoxy is methoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "cycloalkyl" as used herein refers to a saturated or partly unsaturated monocyclic or bicyclic hydrocarbon group of 3 to 10 ring carbon atoms ("$C_{3-10}$-cycloalkyl"). In some preferred embodiments, the cycloalkyl group is a saturated monocyclic hydrocarbon group of 3 to 8 ring carbon atoms. "Bicyclic cycloalkyl" refers to cycloalkyl moieties consisting of two saturated carbocycles having two carbon atoms in common, i.e., the bridge separating the two rings is either a single bond or a chain of one or two ring atoms, and to spirocyclic moieties, i.e., the two rings are connected via one common ring atom. Preferably, the cycloalkyl group is a saturated monocyclic hydrocarbon group of 3 to 6 ring carbon atoms, e.g., of 3, 4, 5 or 6 carbon atoms. Some non-limiting examples of cycloalkyl include cyclopropyl, cyclobutyl, cyclopentyl, cyclohexyl and cycloheptyl. A particularly preferred, yet non-limiting example of cycloalkyl is cyclopropyl.

The term "aryl" refers to a monocyclic, bicyclic, or tricyclic carbocyclic ring system having a total of 6 to 14 ring members ("$C_6$-$C_{14}$-aryl"), preferably, 6 to 12 ring members, and more preferably 6 to 10 ring members, and wherein at least one ring in the system is aromatic. Some non-limiting examples of aryl include phenyl and 9H-fluorenyl (e.g. 9H-fluoren-9-yl). A particularly preferred, yet non-limiting example of aryl is phenyl.

The term "heteroaryl" refers to a mono- or multivalent, monocyclic, bicyclic or tricyclic, preferably bicyclic ring system having a total of 5 to 14 ring members, preferably, 5 to 12 ring members, and more preferably 5 to 10 ring members, wherein at least one ring in the system is aromatic, and at least one ring in the system contains one or more heteroatoms. Preferably, "heteroaryl" refers to a 5-10 membered heteroaryl comprising 1, 2, 3 or 4 heteroatoms independently selected from O, S and N. Most preferably, "heteroaryl" refers to a 5-10 membered heteroaryl comprising 1 to 2 heteroatoms independently selected from 0, S and N. Some non-limiting examples of heteroaryl include spiro[cyclopropane-1,3'-indoline](e.g., spiro[cyclopropane-1,3'-indoline]-1'-yl), 2-pyridyl, 3-pyridyl, 4-pyridyl, indol-1-yl, 1H-indol-2-yl, 1H-indol-3-yl, 1H-indol-4-yl, 1H-indol-5-yl, 1H-indol-6-yl, 1H-indol-7-yl, 1,2-benzoxazol-3-yl, 1,2-benzoxazol-4-yl, 1,2-benzoxazol-5-yl, 1,2-benzoxazol-6-yl, 1,2-benzoxazol-7-yl, 1H-indazol-3-yl, 1H-indazol-4-yl, 1H-indazol-5-yl, 1H-indazol-6-yl, 1H-indazol-7-yl, pyrazol-1-yl, 1H-pyrazol-3-yl, 1H-pyrazol-4-yl, 1H-pyrazol-5-yl, imidazol-1-yl, 1H-imidazol-2-yl, 1H-imidazol-4-yl, 1H-imidazol-5-yl, oxazol-2-yl, oxazol-4-yl, oxazol-5-yl, 1,2,4-oxadiazol-3-yl, 1,2,4-oxadiazol-3-yl, thiazol-2-yl, thiazol-4-yl, thiazol-5-yl, pyridazin-3-yl, and pyridazin-4-yl. Particularly preferred, yet non-limiting examples of heteroaryl are oxadiazolyl, pyridazinyl, pyridyl, and thiazolyl.

The term "hydroxy" refers to an —OH group.
The term "cyano" refers to a —CN (nitrile) group.
The term "amino" refers to an —$NH_2$ group.
The term "alkylsulfonyl" refers to a group alkyl-$SO_2$—.
The term "carbamoyl" refers to a group $H_2N$—C(O)—.
The term "cycloalkylalkoxy" refers to an alkoxy group, wherein at least one of the hydrogen atoms of the alkoxy group has been replaced by a cycloalkyl group. Preferably, "cycloalkylalkoxy" refers to an alkoxy group wherein 1, 2 or 3 hydrogen atoms, most preferably 1 hydrogen atom of the alkoxy group have been replaced by a cycloalkyl group. A particularly preferred, yet non-limiting example of cycloalkylalkoxy is cyclopropylmethoxy.

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. Particularly preferred, yet non-limiting examples of haloalkyl are trifluoromethyl and trifluoroethyl.

The term "haloalkoxy" refers to an alkoxy group, wherein at least one of the hydrogen atoms of the alkoxy group has been replaced by a halogen atom, preferably fluoro. Preferably, "haloalkoxy" refers to an alkoxy group wherein 1, 2 or 3 hydrogen atoms of the alkoxy group have been replaced by a halogen atom, most preferably fluoro. A particularly preferred, yet non-limiting example of haloalkoxy is trifluoromethoxy (—$OCF_3$).

The term "cycloalkylalkoxy" refers to an alkoxy group, wherein at least one of the hydrogen atoms of the alkoxy group has been replaced by a cycloalkyl group. Preferably, "cycloalkylalkoxy" refers to an alkoxy group wherein 1, 2 or 3 hydrogen atoms, most preferably 1 hydrogen atom of the alkoxy group have been replaced by a cycloalkyl group. A particularly preferred, yet non-limiting example of cycloalkylalkoxy is cyclopropylmethoxy.

The term "hydroxyalkyl" refers to an alkyl group, wherein at least one of the hydrogen atoms of the alkyl group has been replaced by a hydroxy group. Preferably, "hydroxyalkyl" refers to an alkyl group wherein 1, 2 or 3 hydrogen atoms, most preferably 1 hydrogen atom of the alkyl group have been replaced by a hydroxy group. Preferred, yet non-limiting examples of hydroxyalkyl are hydroxymethyl and hydroxyethyl (e.g. 2-hydroxyethyl). A particularly preferred, yet non-limiting example of hydroxyalkyl is hydroxymethyl.

The term "aminoalkoxy" refers to an alkoxy group, wherein at least one of the hydrogen atoms of the alkoxy group has been replaced by an amino group. Preferably, "aminoalkoxy" refers to an alkoxy group wherein 1, 2 or 3 hydrogen atoms, most preferably 1 hydrogen atom of the alkoxy group have been replaced by an amino group. Preferred, yet non-limiting examples of aminoalkoxy are aminomethoxy and aminoethoxy (e.g. 2-aminoethoxy).

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochloride salts.

The term "protective group" (PG) denotes the group which selectively blocks a reactive site in a multifunctional compound such that a chemical reaction can be carried out selectively at another unprotected reactive site in the meaning conventionally associated with it in synthetic chemistry. Protective groups can be removed at the appropriate point. Exemplary protective groups are amino-protective groups, carboxy-protective groups or hydroxy-protective groups. Particular protective groups are the tert-butoxycarbonyl (Boc), benzyloxycarbonyl (Cbz), fluorenylmethoxycarbonyl (Fmoc) and benzyl (Bn). Further particular protective groups are the tert-butoxycarbonyl (Boc) and the fluorenylmethoxycarbonyl (Fmoc). More particular protective group is the tert-butoxycarbonyl (Boc). Exemplary protective groups and their application in organic synthesis are described, for example, in "Protective Groups in Organic Chemistry" by T. W. Greene and P. G. M. Wutts, 5th Ed., 2014, John Wiley & Sons, N.Y.

The term "urea forming reagent" refers to a chemical compound that is able to render a first amine to a species that will react with a second amine, thereby forming an urea derivative. Non-limiting examples of a urea forming reagent include bis(trichloromethyl) carbonate, phosgene, trichloromethyl chloroformate, (4-nitrophenyl)carbonate, 1,1'-carbonyl-di-(1,2,4-triazole), and 1,1'-carbonyldiimidazole. The urea forming reagents described in G. Sartori et al., *Green Chemistry* 2000, 2, 140 are incorporated herein by reference.

The compounds of formula (I) can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates.

According to the Cahn-Ingold-Prelog Convention, the asymmetric carbon atom can be of the "R" or "S" configuration.

The abbreviation "MAGL" refers to the enzyme monoacylglycerol lipase. The terms "MAGL" and "monoacylglycerol lipase" are used herein interchangeably.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

The term "neuroinflammation" as used herein relates to acute and chronic inflammation of the nervous tissue, which is the main tissue component of the two parts of the nervous system; the brain and spinal cord of the central nervous system (CNS), and the branching peripheral nerves of the peripheral nervous system (PNS). Chronic neuroinflammation is associated with neurodegenerative diseases such as Alzheimer's disease, Parkinson's disease and multiple sclerosis. Acute neuroinflammation usually follows injury to the central nervous system immediately, e.g., as a result of traumatic brain injury (TBI).

The term "traumatic brain injury" ("TBI", also known as "intracranial injury"), relates to damage to the brain resulting from external mechanical force, such as rapid acceleration or deceleration, impact, blast waves, or penetration by a projectile.

The term "neurodegenerative diseases" relates to diseases that are related to the progressive loss of structure or function of neurons, including death of neurons. Examples of neurodegenerative diseases include, but are not limited to, multiple sclerosis, Alzheimer's disease, Parkinson's disease and amyotrophic lateral sclerosis.

The term "mental disorders" (also called mental illnesses or psychiatric disorders) relates to behavioral or mental patterns that may cause suffering or a poor ability to function in life. Such features may be persistent, relapsing and remitting, or occur as a single episode. Examples of mental disorders include, but are not limited to, anxiety and depression.

The term "pain" relates to an unpleasant sensory and emotional experience associated with actual or potential tissue damage. Examples of pain include, but are not limited to, nociceptive pain, chronic pain (including idiopathic pain), neuropathic pain including chemotherapy induced neuropathy, phantom pain and psychogenic pain. A particular example of pain is neuropathic pain, which is caused by damage or disease affecting any part of the nervous system involved in bodily feelings (i.e., the somatosensory system). In one embodiment, "pain" is neuropathic pain resulting from amputation or thoracotomy. In one embodiment, "pain" is chemotherapy induced neuropathy.

The term "neurotoxicity" relates to toxicity in the nervous system. It occurs when exposure to natural or artificial toxic substances (neurotoxins) alter the normal activity of the nervous system in such a way as to cause damage to nervous tissue. Examples of neurotoxicity include, but are not limited to, neurotoxicity resulting from exposure to substances used in chemotherapy, radiation treatment, drug therapies, drug abuse, and organ transplants, as well as exposure to heavy metals, certain foods and food additives, pesticides, industrial and/or cleaning solvents, cosmetics, and some naturally occurring substances.

The term "cancer" refers to a disease characterized by the presence of a neoplasm or tumor resulting from abnormal uncontrolled growth of cells (such cells being "cancer cells"). As used herein, the term cancer explicitly includes, but is not limited to, hepatocellular carcinoma, colon carcinogenesis and ovarian cancer.

The term "mammal" as used herein includes both humans and non-humans and includes but is not limited to humans, non-human primates, canines, felines, murines, bovines, equines, and porcines. In a particularly preferred embodiment, the term "mammal" refers to humans.

Compounds of the Invention

In a first aspect (A1), the present invention provides compounds of Formula (I)

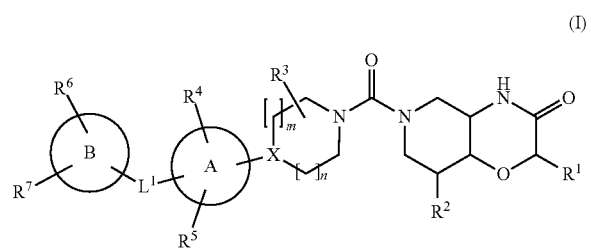

(I)

or pharmaceutically acceptable salts thereof, wherein:

A is selected from $C_6$-$C_{14}$-aryl, 5- to 14-membered heteroaryl and 3- to 14-membered heterocyclyl;

B is
(i) $C_6$-$C_{14}$-aryl; and $L^1$ is —O—; or
(ii) 5- to 14-membered heteroaryl; and $L^1$ is a covalent bond or —O—;

m is 0, n is 0 or 1 and X is $CR^8$; or
m is 1, n is 1 or 2 and X is $CR^8$ or N;

$R^1$, $R^2$, and $R^3$ are independently selected from hydrogen and $C_{1-6}$-alkyl;

$R^4$, $R^5$, $R^6$ and $R^7$ are independently selected from hydrogen, halogen, cyano, hydroxy, $C_{1-6}$-alkoxy, halo-$C_{1-6}$-alkoxy, amino-$C_{1-6}$-alkoxy, $C_{1-6}$-alkyl, halo-$C_{1-6}$-alkyl, hydroxy-$C_{1-6}$-alkyl, $C_{1-6}$-alkylsulfonyl, $SF_5$, carbamoyl, $C_{3-10}$-cycloalkyl-$C_{1-6}$-alkoxy-, $C_{1-6}$-alkyl-NH—C(O)—, $C_{1-6}$-alkyl-C(O)—NH—, and $C_{3-10}$-cycloalkyl, wherein each $C_{3-10}$-cycloalkyl is optionally substituted with 1-2 substituents selected from $C_{1-6}$-alkyl and halo-$C_{1-6}$-alkyl; and $R^8$ is selected from hydrogen, halogen, hydroxy, halo-$C_{1-6}$-alkyl, and $C_{1-6}$-alkyl.

The invention also provides the following enumerated Embodiments (E) of the first aspect (A1) of the invention:

E1. The compound of formula (I) according to A1, or a pharmaceutically acceptable salt thereof, wherein A is $C_6$-$C_{14}$-aryl or 5- to 14-membered heteroaryl.

E2. The compound of formula (I) according to A1, or a pharmaceutically acceptable salt thereof, wherein A is phenyl or pyridyl.

E3. The compound of formula (I) according to A1, or a pharmaceutically acceptable salt thereof, wherein A is $C_6$-$C_{14}$-aryl.

E4. The compound of formula (I) according to A1, or a pharmaceutically acceptable salt thereof, wherein A is phenyl.

E5. The compound of formula (I) according to anyone of A1 and E1-E4, or a pharmaceutically acceptable salt thereof, wherein
B is
(i) phenyl; and $L^1$ is —O—; or
(ii) selected from oxadiazolyl, pyridazinyl, pyridyl, and thiazolyl; and $L^1$ is a covalent bond or —O—.

E6. The compound of formula (I) according to anyone of A1 and E1-E5, wherein:
m is 0, n is 0 and X is $CR^8$; or
m is 1, n is 1 and X is $CR^8$ or N.

E7. The compound of formula (I) according to any one of A1 and E1-E5, wherein m is 0, n is 0 and X is $CR^8$.

E8. The compound of formula (I) according to any one of A1 and E1-E7, wherein $R^1$ is hydrogen.

E9. The compound of formula (I) according to any one of A1 and E1-E8, wherein $R^2$ is hydrogen.

E10. The compound of formula (I) according to any one of A1 and E1-E9, wherein $R^3$ is hydrogen.

E11. The compound of formula (I) according to any one of A1 and E1-E10, wherein $R^4$ is hydrogen.

E12. The compound of formula (I) according to any one of A1 and E1-E11, wherein $R^5$ is hydrogen.

E13. The compound of formula (I) according to any one of A1 and E1-E12, wherein $R^6$ is selected from hydrogen, halogen, cyano, $C_{1-6}$-alkyl, $C_{1-6}$-alkoxy, halo-$C_{1-6}$-alkyl, $C_{3-10}$-cycloalkyl, and $C_{1-6}$-alkylsulfonyl.

E14. The compound of formula (I) according to any one of A1 and E1-E12, wherein $R^6$ is selected from hydrogen, halogen, cyano, and $C_{1-6}$-alkyl.

E15. The compound of formula (I) according to any one of A1 and E1-E12, wherein $R^6$ is selected from hydrogen, fluoro, chloro, cyano, methyl, and 2,2-dimethylpropyl.

E16. The compound of formula (I) according to any one of A1 and E1-E15, wherein $R^7$ is selected from hydrogen, halogen, and $C_{1-6}$-alkyl.

E17. The compound of formula (I) according to any one of A1 and E1-E15, wherein $R^7$ is selected from hydrogen, fluoro, and methyl.

E18. The compound of formula (I) according to any one of A1 and E1-E15, wherein $R^7$ is hydrogen or halogen.

E19. The compound of formula (I) according to any one of A1 and E1-E15, wherein $R^7$ is hydrogen or fluoro.

E20. The compound of formula (I) according to any one of A1 and E1-E19, wherein $R^8$ is hydrogen or hydroxy.

E21. The compound of formula (I) according to any one of A1 and E1-E19, wherein $R^8$ is hydrogen.

E22. The compound of formula (I) according to A1, wherein the compound of formula (I) is a compound of formula (II), or a pharmaceutically acceptable salt thereof,

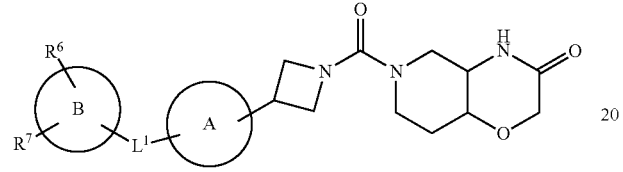

(II)

wherein:

A is $C_6$-$C_{14}$-aryl;

B is (i) $C_6$-$C_{14}$-aryl; and $L^1$ is —O—; or (ii) 5- to 14-membered heteroaryl; and $L^1$ is a covalent bond or —O—;

$R^6$ is selected from hydrogen, halogen, cyano, $C_{1-6}$-alkyl, $C_{1-6}$-alkoxy, halo-$C_{1-6}$-alkyl, $C_{3-10}$-cycloalkyl, and $C_{1-6}$-alkylsulfonyl; and $R^7$ is selected from hydrogen, halogen, and $C_{1-6}$-alkyl.

E23. The compound of formula (I) according to A1, wherein the compound of formula (I) is a compound of formula (II), or a pharmaceutically acceptable salt thereof,

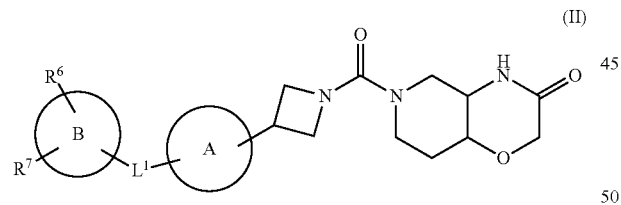

(II)

wherein:

A is $C_6$-$C_{14}$-aryl;

B is (i) $C_6$-$C_{14}$-aryl; and $L^1$ is —O—; or (ii) 5- to 14-membered heteroaryl; and $L^1$ is a covalent bond or —O—;

$R^6$ is selected from hydrogen, halogen, cyano, and $C_{1-6}$-alkyl; and $R^7$ is selected from hydrogen, and halogen.

E24. The compound of formula (I) according to A1, wherein the compound of formula (I) is a compound of formula (III), or a pharmaceutically acceptable salt thereof,

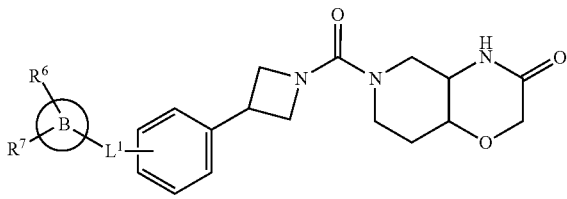

(III)

wherein:

B is (i) phenyl; and $L^1$ is —O—; or (ii) selected from oxadiazolyl, pyridazinyl, pyridyl, and thiazolyl; and $L^1$ is a covalent bond or —O—;

$R^6$ is selected from hydrogen, fluoro, chloro, cyano, methyl, and 2,2-dimethylpropyl; and $R^7$ is selected from hydrogen, and fluoro.

E25. The compound of formula (I) according to A1, wherein the compound of formula (I) is a compound of formula (IIa), or a pharmaceutically acceptable salt thereof,

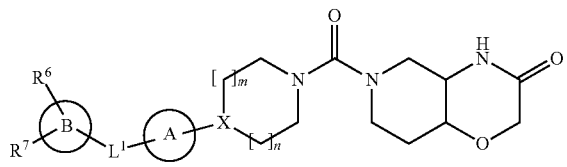

(IIa)

wherein:

A is $C_6$-$C_{14}$-aryl or 5- to 14-membered heteroaryl;

B is (i) $C_6$-$C_{14}$-aryl; and $L^1$ is —O—; or (ii) 5- to 14-membered heteroaryl; and $L^1$ is a covalent bond or —O—;

m is 0, n is 0 and X is $CR^8$; or m is 1, n is 1 and X is $CR^8$ or N;

$R^6$ is selected from hydrogen, halogen, cyano, $C_{1-6}$-alkyl, $C_{1-6}$-alkoxy, halo-$C_{1-6}$-alkyl, $C_{3-10}$-cycloalkyl, and $C_{1-6}$-alkylsulfonyl;

$R^7$ is selected from hydrogen, halogen, and $C_{1-6}$-alkyl; and $R^8$ is selected from hydrogen and hydroxy.

E26. The compound of formula (I) according to A1, wherein the compound of formula (I) is a compound of formula (IIb), or a pharmaceutically acceptable salt thereof,

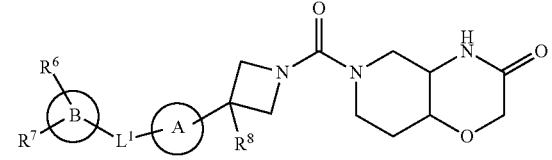

(IIb)

wherein:
A is $C_6$-$C_{14}$-aryl or 5- to 14-membered heteroaryl;
B is
  (i) $C_6$-$C_{14}$-aryl; and $L^1$ is —O—; or
  (ii) 5- to 14-membered heteroaryl; and $L^1$ is a covalent bond or —O—;
$R^6$ is selected from hydrogen, halogen, cyano, and $C_{1-6}$-alkyl;
$R^7$ is selected from hydrogen, $C_{1-6}$-alkyl, and halogen; and
$R^8$ is selected from hydrogen and hydroxy.

E27. The compound of formula (I) according to A1, wherein the compound of formula (I) is a compound of formula (IIb), or a pharmaceutically acceptable salt thereof,

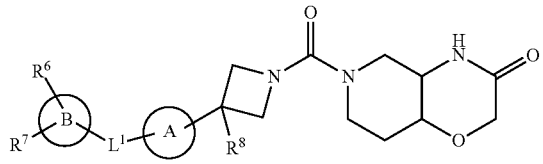

(IIb)

wherein:
A is phenyl or pyridyl;
B is
  (i) phenyl; and $L^1$ is —O—; or
  (ii) selected from oxadiazolyl, pyridazinyl, pyridyl, and thiazolyl; and $L^1$ is a covalent bond or —O—;
$R^6$ is selected from hydrogen, fluoro, chloro, cyano, methyl, and 2,2-dimethylpropyl;
$R^7$ is selected from hydrogen, methyl, and fluoro; and
$R^8$ is selected from hydrogen and hydroxy.

E28. The compound of formula (I) according to any one of A1 and E1-E21, or a pharmaceutically acceptable salt thereof, wherein $R^1$, $R^2$, and $R^3$ are all hydrogen.

E29. The compound of formula (I) according to any one of A1 and E1-E21, or a pharmaceutically acceptable salt thereof, wherein A is $C_6$-$C_{14}$-aryl and $R^4$ and $R^5$ are both hydrogen.

E30. The compound of formula (I) according to any one of A1 and E1-E21, or a pharmaceutically acceptable salt thereof, wherein A is phenyl and $R^4$ and $R^5$ are both hydrogen.

E31. The compound of formula (I) according to any one of A1 and E1-E21, or a pharmaceutically acceptable salt thereof, wherein
B is
  (i) $C_6$-$C_{14}$-aryl; and $L^1$ is —O—; or
  (ii) 5- to 14-membered heteroaryl; and $L^1$ is a covalent bond or —O—;
$R^6$ is selected from hydrogen, halogen, cyano, $C_{1-6}$-alkyl, $C_{1-6}$-alkoxy, halo-$C_{1-6}$-alkyl, $C_{3-10}$-cycloalkyl, and $C_{1-6}$-alkylsulfonyl; and
$R^7$ is selected from hydrogen, halogen, and $C_{1-6}$-alkyl.

E32. The compound of formula (I) according to any one of A1 and E1-E21, or a pharmaceutically acceptable salt thereof, wherein
B is
  (i) $C_6$-$C_{14}$-aryl; and $L^1$ is —O—; or
  (ii) 5- to 14-membered heteroaryl; and $L^1$ is a covalent bond or —O—;
$R^6$ is selected from hydrogen, halogen, cyano, and $C_{1-6}$-alkyl; and
$R^7$ is selected from hydrogen, and halogen.

E33. The compound of formula (I) according to any one of A1 and E1-E21, or a pharmaceutically acceptable salt thereof, wherein
B is
  (i) phenyl; and $L^1$ is —O—; or
  (ii) oxadiazolyl, pyridazinyl, pyridyl, and thiazolyl; and $L^1$ is a covalent bond or —O—;
$R^6$ is selected from hydrogen, fluoro, chloro, cyano, methyl, and 2,2-dimethylpropyl; and
$R^7$ is selected from hydrogen, and fluoro.

E34. The compound of formula (I) according to any one of A1 and E1-E33, or a pharmaceutically acceptable salt thereof, selected from:

(4aR,8aS)-6-(3-(4-Phenoxyphenyl)azetidine-1-carbonyl)hexahydro-2H-pyrido[4,3-b][1,4]oxazin-3(4H)-one;

(4aR,8aS)-6-[3-[4-(2-Chlorophenoxy)phenyl]azetidine-1-carbonyl]-4,4a,5,7,8,8a-hexahydropyrido[4,3-b][1,4]oxazin-3-one;

(4aR,8aS)-6-[3-(4-Pyrimidin-2-yloxyphenyl)azetidine-1-carbonyl]-4,4a,5,7,8,8a-hexahydropyrido[4,3-b][1,4]oxazin-3-one;

(4aR,8aS)-6-[3-[4-[(2-Methyl-3-pyridyl)oxy]phenyl]azetidine-1-carbonyl]-4,4a,5,7,8,8a-hexahydropyrido[4,3-b][1,4]oxazin-3-one;

(4aR,8aS)-6-[3-[4-(4-Methylpyrimidin-2-yl)oxyphenyl]azetidine-1-carbonyl]-4,4a,5,7,8,8a-hexahydropyrido[4,3-b][1,4]oxazin-3-one;

(4aR,8aS)-6-[3-(4-Pyridazin-3-yloxyphenyl)azetidine-1-carbonyl]-4,4a,5,7,8,8a-hexahydropyrido[4,3-b][1,4]oxazin-3-one;

(4aR,8aS)-6-[3-[4-[(4-Methyl-3-pyridyl)oxy]phenyl]azetidine-1-carbonyl]-4,4a,5,7,8,8a-hexahydropyrido[4,3-b][1,4]oxazin-3-one;

(4aR,8aS)-6-[3-[4-[(5-Fluoro-3-pyridyl)oxy]phenyl]azetidine-1-carbonyl]-4,4a,5,7,8,8a-hexahydropyrido[4,3-b][1,4]oxazin-3-one;

(4aR,8aS)-6-[3-[4-[(5-Chloro-3-pyridyl)oxy]phenyl]azetidine-1-carbonyl]-4,4a,5,7,8,8a-hexahydropyrido[4,3-b][1,4]oxazin-3-one;

(4aR,8aS)-6-[3-[4-(3-Pyridyloxy)phenyl]azetidine-1-carbonyl]-4,4a,5,7,8,8a-hexahydropyrido[4,3-b][1,4]oxazin-3-one;

(4aR,8aS)-6-[3-[4-(4-Methylpyridazin-3-yl)oxyphenyl]azetidine-1-carbonyl]-4,4a,5,7,8,8a-hexahydropyrido[4,3-b][1,4]oxazin-3-one;

(4aR,8aS)-6-[3-[4-(3-Chloropyridazin-4-yl)oxyphenyl]azetidine-1-carbonyl]-4,4a,5,7,8,8a-hexahydropyrido[4,3-b][1,4]oxazin-3-one;

(4aR,8aS)-6-[3-[4-(4-Methoxypyrimidin-2-yl)oxyphenyl]azetidine-1-carbonyl]-4,4a,5,7,8,8a-hexahydropyrido[4,3-b][1,4]oxazin-3-one;

(4aR,8aS)-6-[3-[4-[4-(Trifluoromethyl)pyrimidin-2-yl]oxyphenyl]azetidine-1-carbonyl]-4,4a,5,7,8,8a-hexahydropyrido[4,3-b][1,4]oxazin-3-one;

(4aR,8aS)-6-[3-[4-(3-Fluorophenoxy)phenyl]azetidine-1-carbonyl]-4,4a,5,7,8,8a-hexahydropyrido[4,3-b][1,4]oxazin-3-one;

(4aR,8aS)-6-[3-[4-(4-Fluorophenoxy)phenyl]azetidine-1-carbonyl]-4,4a,5,7,8,8a-hexahydropyrido[4,3-b][1,4]oxazin-3-one;

(4aR,8aS)-6-[3-[4-(2,4-Difluorophenoxy)phenyl]azetidine-1-carbonyl]-4,4a,5,7,8,8a-hexahydropyrido[4,3-b][1,4]oxazin-3-one;

(4aR,8aS)-6-[3-[4-(2-Fluorophenoxy)phenyl]azetidine-1-carbonyl]-4,4a,5,7,8,8a-hexahydropyrido[4,3-b][1,4]oxazin-3-one;

(4aR,8aS)-6-[3-[4-(4-Chlorophenoxy)phenyl]azetidine-1-carbonyl]-4,4a,5,7,8,8a-hexahydropyrido[4,3-b][1,4]oxazin-3-one;

(4aR,8aS)-6-[3-[4-(3-Chlorophenoxy)phenyl]azetidine-1-carbonyl]-4,4a,5,7,8,8a-hexahydropyrido[4,3-b][1,4]oxazin-3-one;

(4aR,8aS)-6-[3-[4-(2-Methylphenoxy)phenyl]azetidine-1-carbonyl]-4,4a,5,7,8,8a-hexahydropyrido[4,3-b][1,4]oxazin-3-one;

(4aR,8aS)-6-[3-[4-[3-(Trifluoromethyl)phenoxy]phenyl]azetidine-1-carbonyl]-4,4a,5,7,8,8a-hexahydropyrido[4,3-b][1,4]oxazin-3-one;

2-[4-[1-[(4aR,8aS)-3-Oxo-4,4a,5,7,8,8a-hexahydropyrido[4,3-b][1,4]oxazine-6-carbonyl]azetidin-3-yl]phenoxy]benzonitrile;

(4aR,8aS)-6-[3-[4-(2-Chloropyrimidin-4-yl)oxyphenyl]azetidine-1-carbonyl]-4,4a,5,7,8,8a-hexahydropyrido[4,3-b][1,4]oxazin-3-one;

(+)-(4aR,8aS)-6-[3-[4-(4-Cyclopropylpyrimidin-2-yl)oxyphenyl]azetidine-1-carbonyl]-4,4a,5,7,8,8a-hexahydropyrido[4,3-b][1,4]oxazin-3-one;

(4aR,8aS)-6-[3-[4-[(6-Methyl-2-pyridyl)oxy]phenyl]azetidine-1-carbonyl]-4,4a,5,7,8,8a-hexahydropyrido[4,3-b][1,4]oxazin-3-one;

(4aR,8aS)-6-[3-[4-[(4-chloro-3-pyridyl)oxy]phenyl]azetidine-1-carbonyl]-4,4a,5,7,8,8a-hexahydropyrido[4,3-b][1,4]oxazin-3-one;

(4aR,8aS)-6-[3-[4-[(3-Fluoro-4-pyridyl)oxy]phenyl]azetidine-1-carbonyl]-4,4a,5,7,8,8a-hexahydropyrido[4,3-b][1,4]oxazin-3-one;

(+)-(4aR,8aS)-6-[3-[4-(2-Methylsulfonylpyrimidin-4-yl)oxyphenyl]azetidine-1-carbonyl]-4,4a,5,7,8,8a-hexahydropyrido[4,3-b][1,4]oxazin-3-one;

(4aR,8aS)-6-[3-[4-[(3,6-Dimethyl-2-pyridyl)oxy]phenyl]azetidine-1-carbonyl]-4,4a,5,7,8,8a-hexahydropyrido[4,3-b][1,4]oxazin-3-one;

(4aR,8aS)-6-[3-[4-(1H-Pyrazol-5-yl)phenyl]azetidine-1-carbonyl]-4,4a,5,7,8,8a-hexahydropyrido[4,3-b][1,4]oxazin-3-one;

(4aR,8aS)-6-[3-[4-[2-(2,2-Dimethylpropyl)pyrazol-3-yl]phenyl]azetidine-1-carbonyl]-4,4a,5,7,8,8a-hexahydropyrido[4,3-b][1,4]oxazin-3-one;

(4aR,8aS)-6-[3-[4-[1-(2,2-Dimethylpropyl)pyrazol-3-yl]phenyl]azetidine-1-carbonyl]-4,4a,5,7,8,8a-hexahydropyrido[4,3-b][1,4]oxazin-3-one;

(4aR,8aS)-6-[3-[4-(3-Chloro-2-pyridyl)phenyl]azetidine-1-carbonyl]-4,4a,5,7,8,8a-hexahydropyrido[4,3-b][1,4]oxazin-3-one;

(4aR,8aS)-6-[3-[4-(2,4-Dimethyloxazol-5-yl)phenyl]azetidine-1-carbonyl]-4,4a,5,7,8,8a-hexahydropyrido[4,3-b][1,4]oxazin-3-one;

(4aR,8aS)-6-[3-[4-(3,5-Dimethylpyrazol-1-yl)phenyl]azetidine-1-carbonyl]-4,4a,5,7,8,8a-hexahydropyrido[4,3-b][1,4]oxazin-3-one;

(4aR,8aS)-6-[3-[4-[3-(2,2-Dimethylpropyl)triazol-4-yl]phenyl]azetidine-1-carbonyl]-4,4a,5,7,8,8a-hexahydropyrido[4,3-b][1,4]oxazin-3-one;

(4aR,8aS)-6-[3-[4-[5-(2,2-Dimethylpropyl)-1,2,4-oxadiazol-3-yl]phenyl]azetidine-1-carbonyl]-4,4a,5,7,8,8a-hexahydropyrido[4,3-b][1,4]oxazin-3-one;

(4aR,8aS)-6-[3-[4-[5-(2,2-Dimethylpropyl)-1,3,4-oxadiazol-2-yl]phenyl]azetidine-1-carbonyl]-4,4a,5,7,8,8a-hexahydropyrido[4,3-b][1,4]oxazin-3-one;

(4aR,8aS)-6-[3-[4-[2-(2-Fluoroethyl)pyrazol-3-yl]phenyl]azetidine-1-carbonyl]-4,4a,5,7,8,8a-hexahydropyrido[4,3-b][1,4]oxazin-3-one;

(4aR,8aS)-6-[3-[4-[1-(2-Fluoroethyl)pyrazol-4-yl]phenyl]azetidine-1-carbonyl]-4,4a,5,7,8,8a-hexahydropyrido[4,3-b][1,4]oxazin-3-one;

(4aR,8aS)-6-[3-[4-(4-Methyl-1,3-thiazol-2-yl)phenyl]azetidine-1-carbonyl]-4,4a,5,7,8,8a-hexahydropyrido[4,3-b][1,4]oxazin-3-one;

(4aR,8aS)-6-[3-[4-(1-Methylpyrazol-3-yl)phenyl]azetidine-1-carbonyl]-4,4a,5,7,8,8a-hexahydropyrido[4,3-b][1,4]oxazin-3-one;

(4aR,8aS)-6-[3-[4-(6-Fluoropyridin-3-yl)phenyl]azetidine-1-carbonyl]-4,4a,5,7,8,8a-hexahydropyrido[4,3-b][1,4]oxazin-3-one;

(4aR,8aS)-6-[3-[4-(2-Fluoropyridin-4-yl)phenyl]azetidine-1-carbonyl]-4,4a,5,7,8,8a-hexahydropyrido[4,3-b][1,4]oxazin-3-one;

(4aR,8aS)-6-[3-[4-(1-Methylpyrazol-4-yl)phenyl]azetidine-1-carbonyl]-4,4a,5,7,8,8a-hexahydropyrido[4,3-b][1,4]oxazin-3-one;

(4aR,8aS)-6-[3-[4-(2-Methylpyrazol-3-yl)phenyl]azetidine-1-carbonyl]-4,4a,5,7,8,8a-hexahydropyrido[4,3-b][1,4]oxazin-3-one;

(4aR,8aS)-6-[3-[5-(4-Fluorophenoxy)-2-pyridyl]azetidine-1-carbonyl]-4,4a,5,7,8,8a-hexahydropyrido[4,3-b][1,4]oxazin-3-one;

(4aR,8aS)-6-(3-(6-(4-Fluorophenoxy)pyridin-3-yl)azetidine-1-carbonyl)hexahydro-2H-pyrido[4,3-b][1,4]oxazin-3(4H)-one;

(4aR,8aS)-6-(3-(6-(4-(Trifluoromethoxy)phenoxy)pyridin-3-yl)azetidine-1-carbonyl)hexahydro-2H-pyrido[4,3-b][1,4]oxazin-3(4H)-one;

(4aR,8aS)-6-(3-(6-(4-Chlorophenoxy)pyridin-3-yl)azetidine-1-carbonyl)hexahydro-2H-pyrido[4,3-b][1,4]oxazin-3(4H)-one;

(4aR,8aS)-6-[3-[4-(3,6-Dimethylpyridazin-4-yl)oxyphenyl]azetidine-1-carbonyl]-4,4a,5,7,8,8a-hexahydropyrido[4,3-b][1,4]oxazin-3-one;

(4aR,8aS)-6-(3-(6-(2-Chlorophenoxy)pyridin-3-yl)azetidine-1-carbonyl)hexahydro-2H-pyrido[4,3-b][1,4]oxazin-3(4H)-one;

(4aR,8aS)-6-(3-(6-(3-Chlorophenoxy)pyridin-3-yl)azetidine-1-carbonyl)hexahydro-2H-pyrido[4,3-b][1,4]oxazin-3(4H)-one;

(4aR,8aS)-6-[4-[4-(4-Fluorophenoxy)phenyl]piperidine-1-carbonyl]-4,4a,5,7,8,8a-hexahydropyrido[4,3-b][1,4]oxazin-3-one;

(4aR,8aS)-6-[3-Hydroxy-3-(4-phenoxyphenyl)azetidine-1-carbonyl]-4,4a,5,7,8,8a-hexahydropyrido[4,3-b][1,4]oxazin-3-one;

(4aR,8aS)-6-[3-Hydroxy-3-(5-phenoxy-2-pyridyl)azetidine-1-carbonyl]-4,4a,5,7,8,8a-hexahydropyrido[4,3-b][1,4]oxazin-3-one;

(4aR,8aS)-6-[4-(4-Phenoxyphenyl)piperidine-1-carbonyl]-4,4a,5,7,8,8a-hexahydropyrido[4,3-b][1,4]oxazin-3-one; and (4aR,8aS)-6-[4-(4-Phenoxyphenyl)piperazine-1-carbonyl]-4,4a,5,7,8,8a-hexahydropyrido[4,3-b][1,4]oxazin-3-one.

E35. The compound of formula (I) according to E34, or a pharmaceutically acceptable salt thereof, selected from:

(4aR,8aS)-6-(3-(4-Phenoxyphenyl)azetidine-1-carbonyl)hexahydro-2H-pyrido[4,3-b][1,4]oxazin-3(4H)-one;

(4aR,8aS)-6-[3-[4-(3-Chloropyridazin-4-yl)oxyphenyl]azetidine-1-carbonyl]-4,4a,5,7,8,8a-hexahydropyrido[4,3-b][1,4]oxazin-3-one;

(4aR,8aS)-6-[3-[4-(2,4-Difluorophenoxy)phenyl]azetidine-1-carbonyl]-4,4a,5,7,8,8a-hexahydropyrido[4,3-b][1,4]oxazin-3-one;

(4aR,8aS)-6-[3-[4-(2-Fluorophenoxy)phenyl]azetidine-1-carbonyl]-4,4a,5,7,8,8a-hexahydropyrido[4,3-b][1,4]oxazin-3-one; 2-[4-[1-[(4aR,8aS)-3-Oxo-4,4a,5,7,8,8a-hexahydropyrido[4,3-b][1,4]oxazine-6-carbonyl]azetidin-3-yl]phenoxy]benzonitrile;

(4aR,8aS)-6-[3-[4-(3-Chloro-2-pyridyl)phenyl]azetidine-1-carbonyl]-4,4a,5,7,8,8a-hexahydropyrido[4,3-b][1,4]oxazin-3-one;

(4aR,8aS)-6-[3-[4-[5-(2,2-Dimethylpropyl)-1,2,4-oxadiazol-3-yl]phenyl]azetidine-1-carbonyl]-4,4a,5,7,8,8a-hexahydropyrido[4,3-b][1,4]oxazin-3-one;

(4aR,8aS)-6-[3-[4-(4-Methyl-1,3-thiazol-2-yl)phenyl]azetidine-1-carbonyl]-4,4a,5,7,8,8a-hexahydropyrido[4,3-b][1,4]oxazin-3-one;

(4aR,8aS)-6-[3-[5-(4-fluorophenoxy)-2-pyridyl]azetidine-1-carbonyl]-4,4a,5,7,8,8a-hexahydropyrido[4,3-b][1,4]oxazin-3-one;

(4aR,8aS)-6-[3-[4-(3,6-dimethylpyridazin-4-yl)oxyphenyl]azetidine-1-carbonyl]-4,4a,5,7,8,8a-hexahydropyrido[4,3-b][1,4]oxazin-3-one;

(4aR,8aS)-6-[3-[6-(2-chlorophenoxy)-3-pyridyl]azetidine-1-carbonyl]-4,4a,5,7,8,8a-hexahydropyrido[4,3-b][1,4]oxazin-3-one; and (4aR,8aS)-6-[3-hydroxy-3-(4-phenoxyphenyl)azetidine-1-carbonyl]-4,4a,5,7,8,8a-hexahydropyrido[4,3-b][1,4]oxazin-3-one.

E36. The compound of formula (I) according to any one of A1 and E1-E21, or a pharmaceutically acceptable salt thereof, wherein $R^1$ and $R^2$ are both hydrogen.

E37. The compound of formula (I) according to any one of A1 and E1-E21, or a pharmaceutically acceptable salt thereof, wherein:
$R^3$ is hydrogen;
m is 0, n is 0 and X is $CR^8$; or
m is 1, n is 1 and X is $CR^8$ or N; and
$R^8$ is hydrogen or hydroxy.

E38. The compound of formula (I) according to any one of A1 and E1-E21, or a pharmaceutically acceptable salt thereof, wherein:
$R^3$ is hydrogen;
m is 0, n is 0 and X is $CR^8$; and
$R^8$ is hydrogen or hydroxy.

E39. The compound of formula (I) according to any one of A1 and E1-E21, or a pharmaceutically acceptable salt thereof, wherein:
A is $C_6$-$C_{14}$-aryl or 5- to 14-membered heteroaryl;
B is
  (i) $C_6$-$C_{14}$-aryl; and $L^1$ is —O—; or
  (ii) 5- to 14-membered heteroaryl; and $L^1$ is a covalent bond or —O—;
$R^4$ and $R^5$ are both hydrogen;
$R^6$ is selected from hydrogen, halogen, cyano, $C_{1-6}$-alkyl, $C_{1-6}$-alkoxy, halo-$C_{1-6}$-alkyl, $C_{3-10}$-cycloalkyl, and $C_{1-6}$-alkylsulfonyl; and
$R^7$ is selected from hydrogen, halogen, and $C_{1-6}$-alkyl.

E40. The compound of formula (I) according to any one of A1 and E1-E21, or a pharmaceutically acceptable salt thereof, wherein:
A is $C_6$-$C_{14}$-aryl or 5- to 14-membered heteroaryl;
B is
  (i) $C_6$-$C_{14}$-aryl; and $L^1$ is —O—; or
  (ii) 5- to 14-membered heteroaryl; and $L^1$ is a covalent bond or —O—;
$R^4$ and $R^5$ are both hydrogen;
$R^6$ is selected from hydrogen, halogen, cyano, and $C_{1-6}$-alkyl; and
$R^7$ is selected from hydrogen, halogen, and $C_{1-6}$-alkyl.

E41. The compound of formula (I) according to any one of A1 and E1-E21, or a pharmaceutically acceptable salt thereof, wherein:
A is phenyl or pyridyl;
B is
  (i) phenyl; and $L^1$ is —O—; or
  (ii) selected from oxadiazolyl, pyridazinyl, pyridyl, and thiazolyl; and $L^1$ is a covalent bond or —O—;
$R^4$ and $R^5$ are both hydrogen;
$R^6$ is selected from hydrogen, fluoro, chloro, cyano, methyl, and 2,2-dimethylpropyl; and
$R^7$ is selected from hydrogen, halogen, and methyl.

In a particular embodiment, the present invention provides pharmaceutically acceptable salts of the compounds according to formula (I) as described herein, especially hydrochloride salts. In a further particular embodiment, the present invention provides compounds according to formula (I) as described herein as free bases.

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$C, $^{123}$I, and $^{125}$I, respectively. Certain isotopically-labeled compounds of formula (I), for example, those incorporating a radioactive isotope, are useful in drug and/or substrate tissue distribution studies. The radioactive isotopes tritium, i.e. $^3$H, and carbon-14, i.e., $^{14}$C, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^2$H, may afford certain therapeutic advantages resulting from greater metabolic stability, for example, increased in vivo half-life or reduced dosage requirements.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes of Manufacturing

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. The substituents and indices used in the following description of the processes have the significance given herein, unless indicated to the contrary.

If one of the starting materials, intermediates or compounds of formula (I) contain one or more functional groups which are not stable or are reactive under the reaction conditions of one or more reaction steps, appropriate protective groups (as described e.g., in "Protective Groups in Organic Chemistry" by T. W. Greene and P. G. M. Wutts, 5th Ed., 2014, John Wiley & Sons, N.Y.) can be introduced before the critical step applying methods well known in the art. Such protective groups can be removed at a later stage of the synthesis using standard methods described in the literature.

If starting materials or intermediates contain stereogenic centers, compounds of formula (I) can be obtained as mixtures of diastereomers or enantiomers, which can be separated by methods well known in the art e.g., chiral HPLC, chiral SFC or chiral crystallization. Racemic compounds can e.g., be separated into their antipodes via diastereomeric salts by crystallization with optically pure acids or by separation of the antipodes by specific chromatographic methods using either a chiral adsorbent or a chiral eluent. It is equally possible to separate starting materials and intermediates containing stereogenic centers to afford diastereomerically/enantiomerically enriched starting materials and intermediates. Using such diastereomerically/enantiomerically enriched starting materials and intermediates in the synthesis of compounds of formula (I) will typically lead to the respective diastereomerically/enantiomerically enriched compounds of formula (I).

A person skilled in the art will acknowledge that in the synthesis of compounds of formula (I)—insofar not desired otherwise—an "orthogonal protection group strategy" will be applied, allowing the cleavage of several protective groups one at a time each without affecting other protective groups in the molecule. The principle of orthogonal protection is well known in the art and has also been described in literature (e.g. Barany and R. B. Merrifield, *J Am. Chem. Soc.* 1977, 99, 7363; H. Waldmann et al., *Angew. Chem. Int. Ed. Engl.* 1996, 35, 2056).

A person skilled in the art will acknowledge that the sequence of reactions may be varied depending on reactivity and nature of the intermediates.

In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations*, 2nd Edition, Richard C. Larock. John Wiley & Sons, New York, NY 1999). It was found convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity, the sequence of reaction steps can be freely altered.

If starting materials or intermediates are not commercially available or their synthesis not described in literature, they can be prepared in analogy to existing procedures for close analogues or as outlined in the experimental section.

The following abbreviations are used in the present text: AcOH=acetic acid, ACN=acetonitrile, Bn=benzyl, Boc=tert-butyloxycarbonyl, CAS RN=chemical abstracts registration number, Cbz=benzyloxycarbonyl, $Cs_2CO_3$=cesium carbonate, CO=carbon monoxide, CuCl=copper(I) chloride, CuCN=copper(I) cyanide, CuI=copper(I) iodide, DAST=(diethylamino)sulfur trifluoride, DBU=1,8-diazabicyclo[5,4,0]undec-7-ene, DEAD=diethyl azodicarboxylate, DIAD=diisopropyl azodicarboxylate, DMAP=4-dimethylaminopyridine, DME=dimethoxyethane, DMEDA=N,N'-dimethylethylenediamine, DMF=N,N-dimethylformamide, DIPEA=N,N-diisopropylethylamine, dppf=1,1 bis(diphenyl phosphino)ferrocene, EDC·HCl=N-(3-dimethylaminopropyl)-N'-ethylcarbodiimide hydrochloride, EI=electron impact, ESI=electrospray ionization, EtOAc=ethyl acetate, EtOH=ethanol, h=hour(s), FA=formic acid, $H_2O$=water, $H_2SO_4$=sulfuric acid, HATU=1-[bis(dimethylamino)methylene]-1H-1,2,3-triazolo[4,5-b]pyridinium-3-oxide hexafluorophosphate, HBTU=O-benzotriazole-N,N,N',N'-tetramethyl-uronium-hexafluoro-phosphate, HCl=hydrogen chloride, HOBt=1-hydroxy-1H-benzotriazole; HPLC=high performance liquid chromatography, iPrMgCl=isopropylmagnesium chloride, $I_2$=iodine, IPA=2-propanol, ISP=ion spray positive (mode), ISN=ion spray negative (mode), $K_2CO_3$=potassium carbonate, $KHCO_3$=potassium bicarbonate, KI=potassium iodide, KOH=potassium hydroxide, $K_3PO_4$=potassium phosphate tribasic, $LiAlH_4$ or LAH=lithium aluminium hydride, LiHMDS=lithium bis(trimethylsilyl)amide, LiOH=lithium hydroxide, mCPBA=meta-chloroperoxybenzoic acid, $MgSO_4$=magnesium sulfate, min=minute(s), mL=milliliter, MPLC=medium pressure liquid chromatography, MS=mass spectrum, nBuLi=n-butyllithium, $NaBH_3CN$=sodium cyanoborohydride, NaH=sodium hydride, $NaHCO_3$=sodium hydrogen carbonate, $NaNO_2$=sodium nitrite, $NaBH(OAc)_3$=sodium triacetoxyborohydride, NaOH=sodium hydroxide, $Na_2CO_3$=sodium carbonate, $Na_2SO_4$=sodium sulfate, $Na_2S_2O_3$=sodium thiosulfate, NBS=N-bromosuccinimide, nBuLi=n-butyllithium, $NEt_3$=triethylamine (TEA), $NH_4Cl$=ammonium chloride, NMP=N-methyl-2-pyrrolidone, OAc=Acetoxy, $T_3P$=propylphosphonic anhydride, PE=petroleum ether, PG=protective group, Pd—C=palladium on activated carbon, $PdCl_2(dppf)$-$CH_2Cl_2$=1,1'-bis(diphenylphosphino)ferrocene-palladium (II)dichloride dichloromethane complex, $Pd_2(dba)_3$=tris (dibenzylideneacetone)dipalladium(O), $Pd(OAc)_2$=palladium(II) acetate, $Pd(OH)_2$=palladium hydroxide, $Pd(PPh_3)_4$=tetrakis(triphenylphosphine)palladium(O), PTSA=p-toluenesulfonic acid, R=any group, RT=room temperature, SFC=Supercritical Fluid Chromatography, S-PHOS=2-dicyclohexylphosphino-2',6'-dimethoxybiphenyl, TBAI=tetra butyl ammonium iodine, TEA=triethylamine, TFA=trifluroacetic acid, THF=tetrahydrofuran, TMEDA=N,N,N',N'-tetramethylethylenediamine, $ZnCl_2$=zinc chloride, Hal=halogen.

Compounds of formula I wherein A, B, $L^1$, X, m, n, $R^1$, $R^2$, $R^3$, $R^4$, $R^5$, $R^6$ and $R^7$ areas described herein can be synthesized in analogy to literature procedures and/or as depicted for example in Scheme 1.

Scheme 1

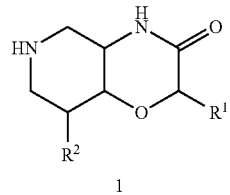

1

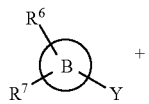

2

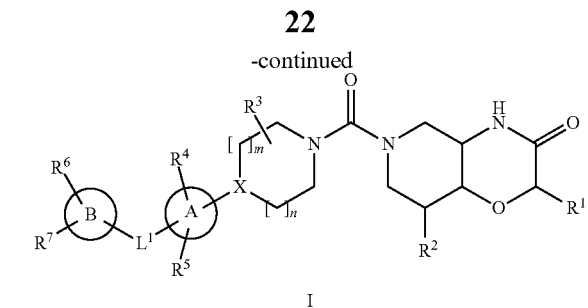

I

Accordingly, 4a,5,6,7,8,8a-hexahydro-4H-pyrido[4,3-b][1,4]oxazin-3-ones 1 are reacted with intermediates 2 in the presence of a urea forming reagent such as bis(trichloromethyl) carbonate using a suitable base and solvent such as, e.g. sodium bicarbonate in DCM, to give compounds of formula I (step a). Further urea forming reagents include but are not limited to phosgene, trichloromethyl chloroformate, (4-nitrophenyl)carbonate or 1,1'-carbonyldiimidazole. Reactions of this type and the use of these reagents are widely described in literature (e.g. G. Sartori et al., *Green Chemistry* 2000, 2, 140). A person skilled in the art will acknowledge that the order of the addition of the reagents can be important in this type of reactions due to the reactivity and stability of the intermediary formed carbamoyl chlorides, as well as for avoiding formation of undesired symmetrical urea by-products.

Compounds IA in which $R^1$ to $R^7$, m, n, $L^1$ A and B are as described herein, can be prepared by methods well known by a person skilled in the art and as exemplified by the general synthetic procedure outlined in Scheme 1a.

Scheme 1a

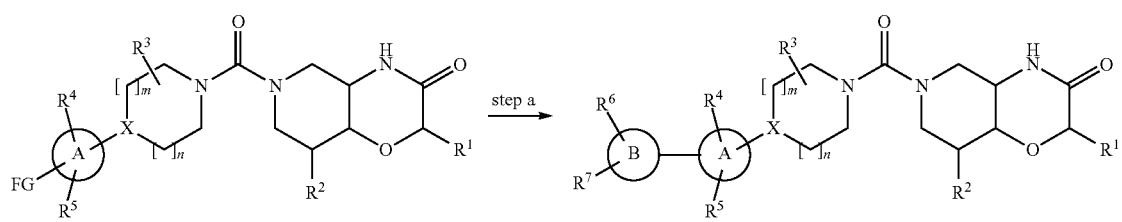

7a (Y = B(OR$^a$)$_2$)
7b (Y = Br)

2a
FG = Functional group, e.g. Br, I

↓ step b

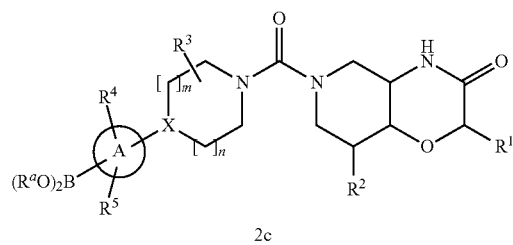

2c (R$^a$O)$_2$B = e.g. (HO)$_2$B,

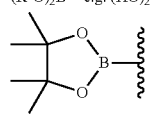

Intermediates 2a, prepared in analogy to scheme 1, can be reacted with aryl or heteroaryl boronic acids 7a (Y=B (OH)$_2$) or boronic esters, Y=e.g. 4,4,5,5-tetramethyl-2-phenyl-1,3,2-dioxaborolane (pinacol) ester, either commercially available or prepared using literature procedures as described for example in "Boronic Acids—Preparation and Applications in Organic Synthesis and Medicine" by Dennis G. Hall (ed.) 1st Ed., 2005, John Wiley & Sons, New York) using a suitable catalyst (e.g. dichloro[1,1'-bis(diphenylphosphino)-ferrocene]palladium(II) dichloromethane adduct, tetrakis(triphenylphosphine)palladium(0) or palladium(II)acetate with triphenylphosphine) in an appropriate solvent (e.g. dioxane, dimethoxyethane, water, toluene, DMF or mixtures thereof) and a suitable base (e.g. Na$_2$CO$_3$, NaHCO$_3$, KF, K$_2$CO$_3$ or TEA) at temperatures between room temperature and the boiling point of the solvent or solvent mixture, to yield compounds IA (step a). Suzuki reactions of this type are broadly described in literature (e.g. A. Suzuki, Pure Appl. Chem. 1991, 63, 419-422; A. Suzuki, N. Miyaura, Chem. Rev. 1995, 95, 2457-2483; A. Suzuki, J. Organomet. Chem. 1999, 576, 147-168; V. Polshettiwar et al., Chem. Sus. Chem. 2010, 3, 502-522) and are well known to those skilled in the art. Alternatively, aryl- or heteroaryl-trifluoroborates (7a with Y=BF$_3$) can be used in the cross-coupling reaction applying a palladium catalyst such as, e.g. tetrakis(triphenylphosphine)-palladium(0), palladium(II) acetate or dichloro[1,1'-bis(diphenylphosphino)ferrocene]-palladium(II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture (step a).

Alternatively, the bromine or iodine in intermediates 2a can be exchanged to a boronic acid or boronic ester group using for examples the methods described under step a) to give intermediates 2c (step b).

Intermediates 2c can then be reacted with intermediates 7b in which FG is for example bromine, either commercially available to prepared in analogy to literature methods, applying the reaction conditions described before to furnish compounds IA (step c).

Furthermore, intermediates 7b in which Y is preferably bromine can be subjected to a cross-electrophile coupling with intermediates 2a with FG preferably being bromine, prepared in analogy to scheme 1, under irradiation with a 420 nm blue light lamp using an appropriate photo catalyst such as [Ir{dF(CF$_3$)ppy}$_2$(dtbpy)]PF$_6$ ([4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate), a Nickel catalyst like NiCl$_2$ glyme (dichloro(dimethoxyethane)nickel), 4,4'-di-tert-butyl-2,2'-dipyridyl and tris(trimethylsilyl)silane, in the presence of a suitable base such as anhydrous sodium carbonate in a solvent like DME. Reactions of this type are described in literature, e.g. J. Am. Chem. Soc. 2016, 138, 8084. (step a).

Compounds of formula IB wherein A, B, R$^1$ to R$^7$, m, n, and X and are as described herein and L$^1$ is oxygen, may be synthesized according to the general procedure outlined in Scheme 1b.

Scheme 1b

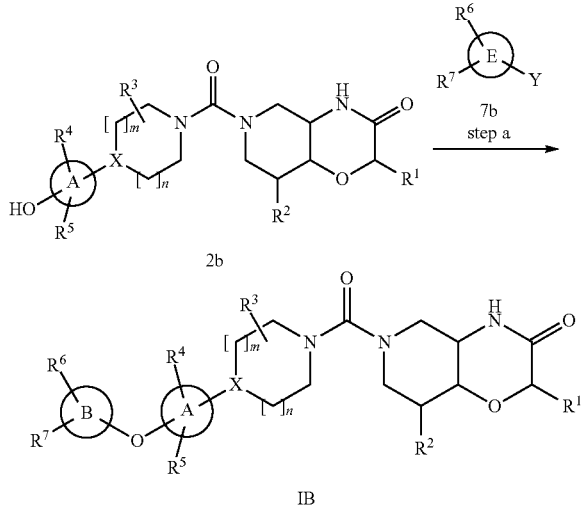

Accordingly, intermediates 2b (obtainable e.g. by the general procedure outlined in Scheme 3), can be transformed to compound IB, by applying nucleophilic aromatic substitution reaction. Treatment of hydroxy intermediates 2b with a suitable heteroaryl compound 7b, wherein Y is a suitable halogen such as fluorine, chlorine or bromine, preferably fluorine or chlorine, wherein R$^6$ and R$^7$ are described herein, such as 2-chloro-pyrimidine, 2-chloro-4-methylpyrimidine, 3-chloropyridazine, 3,4-dichloropyridazine, 2-chloro-4-methoxypyrimidine, 2-chloro-4-trifluoromethyl)pyrimidine, 3-fluoro-4-methylpyridine, 3,5-difluoropyridine, 3-chloro-5-fluoro-pyridine, 3-fluoropyridine, 2-fluorobenzonitrile, 2-fluoro-6-methylpyridine, 4-bromo-2-chloro-pyrimidine, 2-chloro-4-cyclopropylpyrimidine, 4-chloro-3-fluoropyridine and 4-chloro-2-(methylsulfonyl)pyrimidine using a suitable base such as K$_2$CO$_3$ or Cs$_2$CO$_3$ in an appropriate solvent such as DMSO, DMF or NMP at temperatures ranging from 0° C. up to 200° C., optionally applying microwave heating, yield compounds of formula IB (step a).

Alternatively, compounds of formula IB wherein A, B, R$^1$ to R$^7$, m, n and X and are as described herein and L$^1$ is oxygen, may be synthesized according to the general procedure outlined in Scheme 1c.

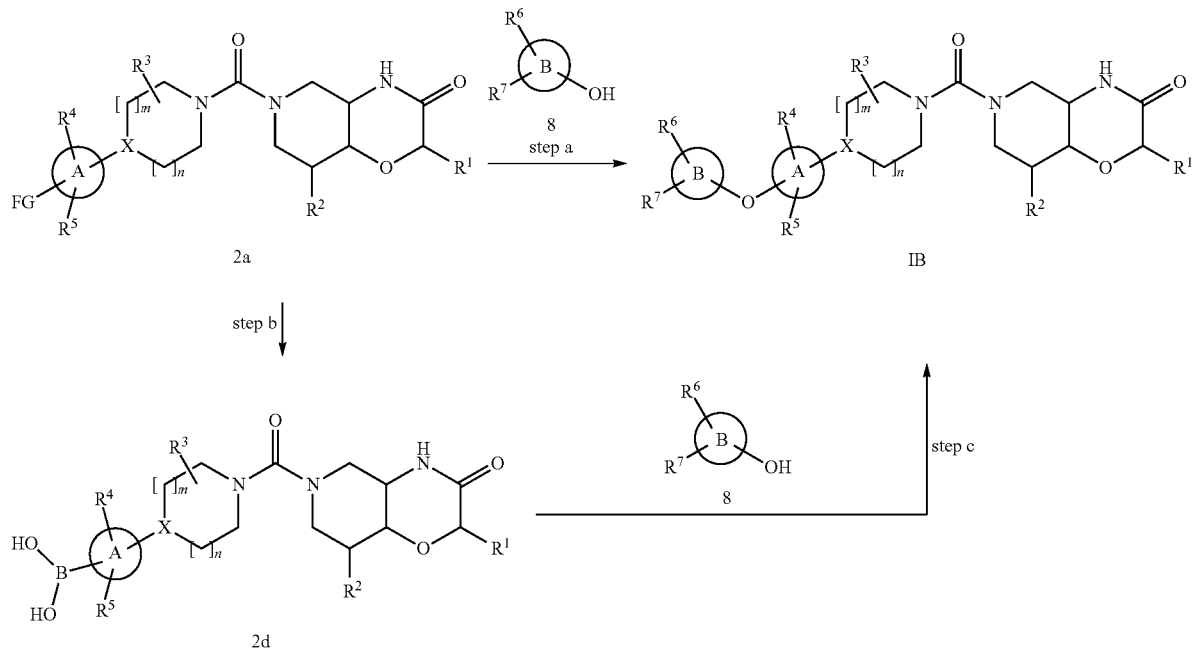

Scheme 1c

Accordingly, intermediates of type 2a (obtainable e.g. by the general procedure outlined in Scheme 4), wherein FG is a suitable halogen such as chlorine or bromine, preferably bromine, can be transformed to compound IB, by applying Buchwald-Hartwig cross-coupling reaction. Treatment of intermediates 2a with a suitable phenol compound 8, wherein R$^6$ and R$^7$ are described herein, such as phenol, using a suitable catalyst system such as Pd(OAc)$_2$ and 2-di-tert-butylphosphino-2',4',6'-triisopropylbiphenyl in the presence of a base such as K$_3$PO$_4$ in an appropriate solvent such as toluene at temperatures ranging from room temperature up to the boiling point of the solvent, optionally applying microwave heating, yield compounds of formula IB (step a).

Alternatively, the bromine in intermediates 2a can be exchanged to a boronic acid group to give intermediates 2d (obtainable e.g. by the general procedure outlined in Scheme 4) (step b).

Intermediates 2d can be then transformed to compound IB, by applying Chan-Lam cross coupling reaction. Treatment of boronic acid intermediates 2d with a suitable phenol compound 8, wherein R$^6$ and R$^7$ are described herein, such as 2-fluorophenol, 3-fluorophenol, 4-fluorophenol, 2,4-difluorophenol, 2-chlorophenol, 3-chlorophenol, 4-chlorophenol, 2-methylphenol and 3-trifluoromethylphenol, in presence of TEA, Cu(OAc)$_2$ and molecular sieves in a solvent like DCM, DCE or CH$_3$CN at room temperature, yields compounds of formula IB (step c).

Intermediates 1 may be synthesized as depicted for example in Scheme 2 and/or in analogy to methods described in literature.

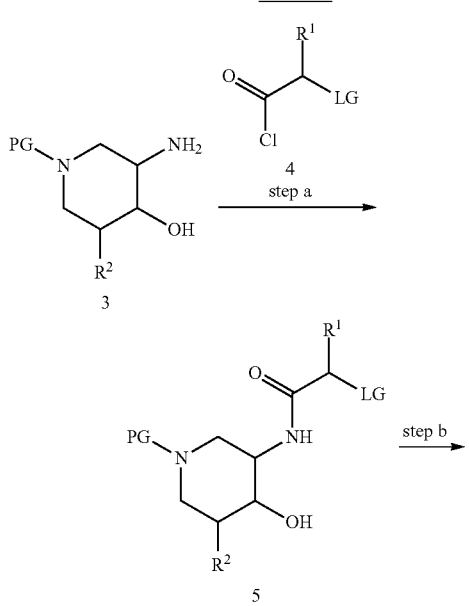

Scheme 2

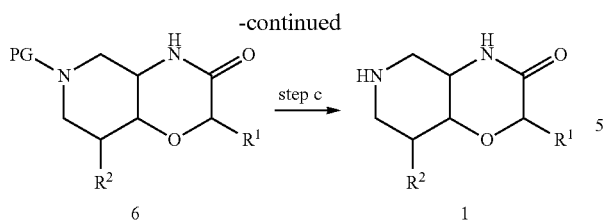

Thus, 3-aminopiperidin-4-ol derivatives 3 in which "PG" signifies a suitable protective group such as a Cbz or Boc protective group can be acylated for example with acyl chlorides 4 in which $R^1$ is as defined herein and "LG" signifies a suitable leaving group (e.g., Cl or Br), using a suitable base such as sodium or potassium carbonate, sodium hydroxide or sodium acetate in an appropriate solvent such as THF, water, acetone or mixtures thereof, to provide intermediates 5 (step a). Intermediates 4 are either commercially available or can be prepared according to literature methods in achiral ($R^1$=H) racemic ($R^1$ not H) or enantiomerically pure form ($R^1$ not H).

Intermediates 5 can be cyclized to intermediates 6 using methods well known in the art, for example by treatment of 5 with sodium hydride in THF or potassium tert-butoxide in IPA and water (step b). Reactions of that type are described in literature (e.g. Z. Rafinski et al., *J. Org. Chem.* 2015, 80, 7468; S. Dugar et al., *Synthesis* 2015, 47(5), 712; WO2005/066187). Removal of the protective group in intermediates 6, applying methods known in the art (e.g., a Boc group using TFA in DCM at temperatures between 0° C. and room temperature, a Cbz group using hydrogen in the presence of a suitable catalyst such as Pd or Pd(OH)$_2$ on charcoal in a suitable solvent such as MeOH, EtOH, EtOAc or mixtures thereof and as described for example in "Protective Groups in Organic Chemistry" by T. W. Greene and P. G. M. Wuts, 4th Ed., 2006, Wiley N.Y.), furnishes intermediates 1 (step c).

Intermediates 1 can be obtained as mixtures of diastereomers and enantiomers, respectively, or as single stereoisomers depending on whether racemic mixtures or enantiomerically pure forms of cis- or trans-3-aminopiperidin-4-ol derivatives 3 are employed in their syntheses. Intermediates 3 are commercially available and their synthesis has also been described in literature (e.g. WO2005/066187; WO2011/0059118; WO2016/185279). Optically pure cis-configured intermediates 1B and 1C can be obtained for example according to Scheme 3 by chiral separation of commercially available rac-(4aR,8aS)-4a,5,6,7,8,8a-hexahydro-4H-pyrido[4,3-b][1,4]oxazin-3-one (1A) (optionally in form of a salt such as, e.g. a hydrochloride salt) using methods known in the art, e.g. by diastereomeric salt crystallization or by chiral chromatography (step a).

In some embodiments, intermediates 2 are intermediates of type 2b. Intermediates 2b in which A is aryl, m=n=0, $R^1$, $R^2$, $R^3$, $R^4$, $R^5$ and $R^8$ are as described herein, can be prepared by methods well known by a person skilled in the art and as exemplified by the general synthetic procedure outlined in Scheme 3.

Scheme 3

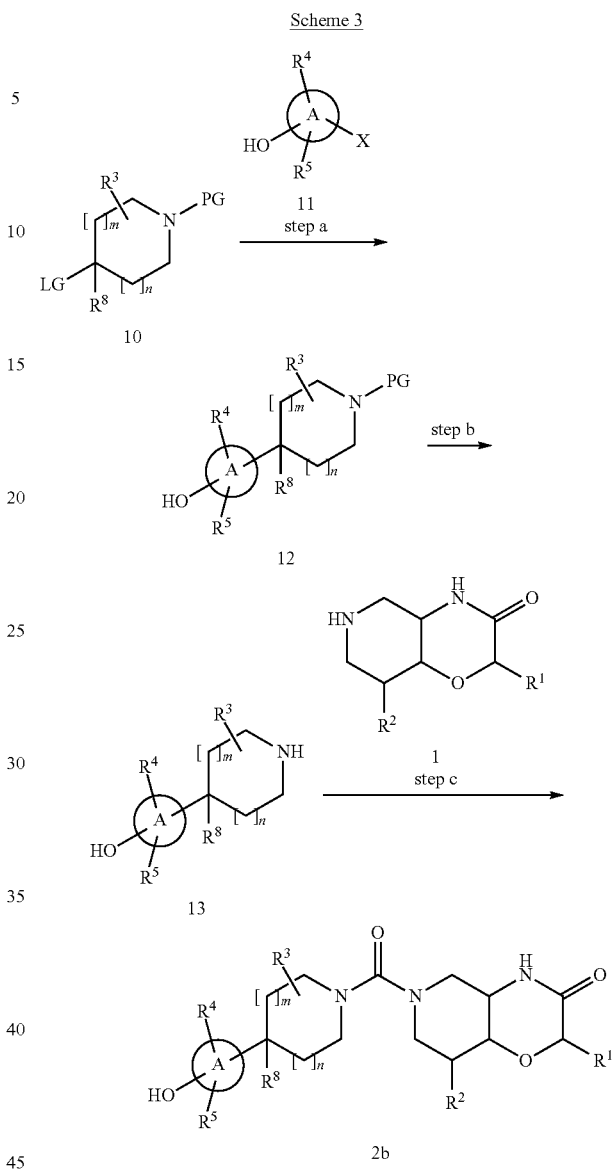

Protected amines 10, either commercially available or prepared by methods known in the art, wherein LG is a suitable leaving group such as bromine or iodine, preferably bromine, m, n and $R^3$ are as described herein and PG is a suitable protecting group such as, e.g. a Boc, Cbz or Bn, can be subjected to a cross-electrophile coupling with arylbromides 11, wherein X is bromine, $R^4$ and $R^5$ are as described herein, such as 4-bromophenol under irradiation with a 420 nm blue light lamp using an appropriate photo catalyst such as [Ir{dF(CF$_3$)ppy}2(dtbpy)]PF$_6$ ([4,4'-bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate), a Nickel catalyst like NiCl$_2$ glyme (dichloro(dimethoxyethane)nickel), 4,4'-di-tert-butyl-2,2'-dipyridyl and tris(trimethylsilyl)silane, in the presence of a suitable base such as anhydrous sodium carbonate in a solvent like DME. Reactions of this type are described in literature, e.g. *J Am. Chem. Soc.* 2016, 138, 8084. (step a). Removal of the protective group from intermediates 12 applying methods well known in the art and as described under Scheme 2, step c, furnishes intermediates 13 (step b). Amines 13 can be then coupled with intermediates 1 applying for example the conditions outlined under Scheme 1, step a, to give intermediates 2b (step c).

In some embodiments, intermediates 2 are intermediates of type 2a, 2c or 2d. Intermediates 2a, 2c and 2d in which A is aryl, m=n=0, $R^1$, $R^2$, $R^3$, $R^4$ $R^5$ and $R^8$ are as described herein, can be prepared by methods well known by a person skilled in the art and as exemplified by the general synthetic procedure outlined in Scheme 4.

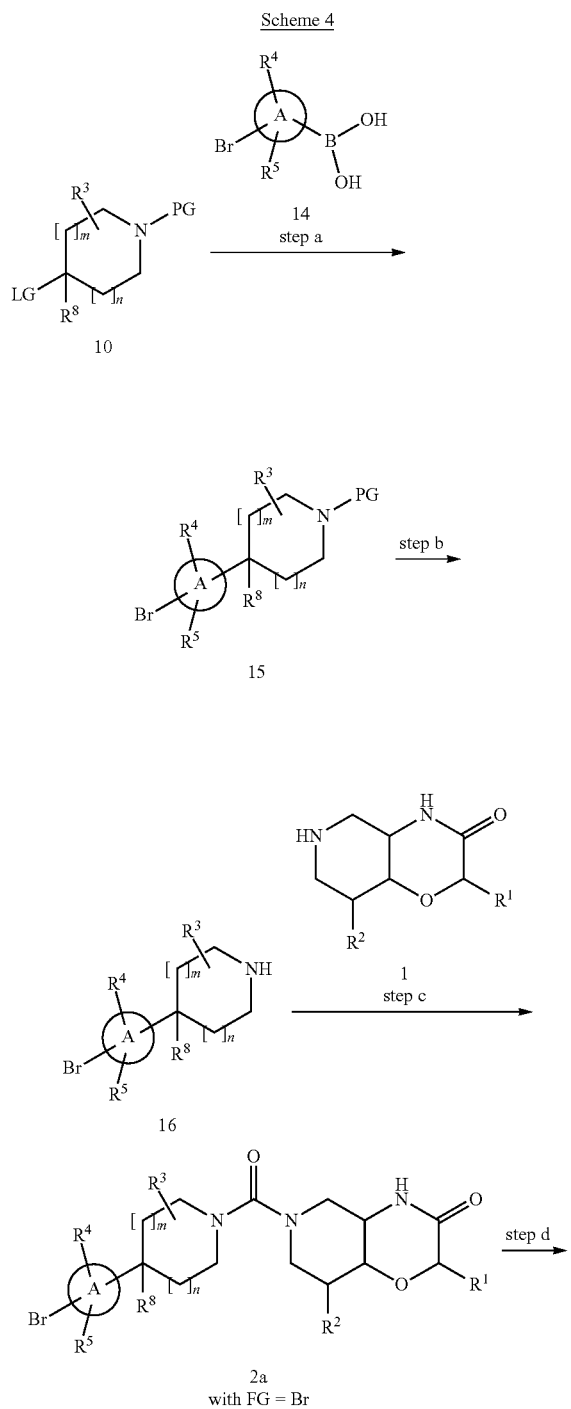

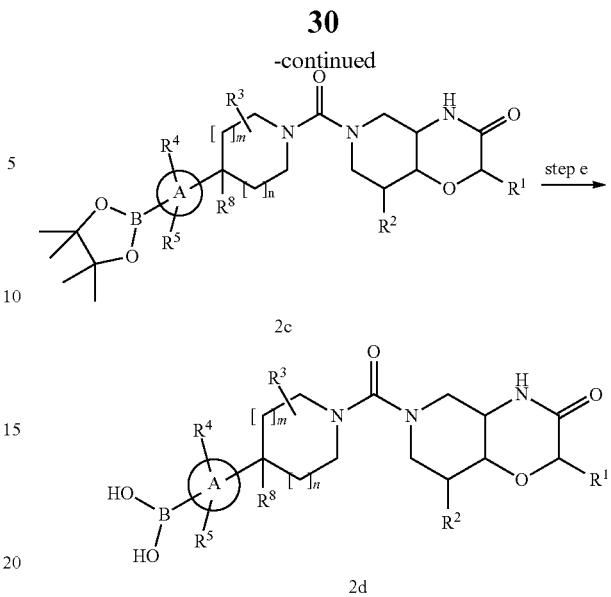

Protected amines 10, either commercially available or prepared by methods known in the art, wherein LG is a suitable leaving group such as such bromine or iodine, preferably iodine, m, n and $R^3$ are as described herein and PG is a suitable protecting group such as, e.g. a Boc, Cbz or Bn, can be subjected to Suzuki-Miyaura cross coupling reaction with arylboronic acids 14, such as 4-bromophenyl-boronic acid, using a suitable Nickel catalyst such as nickel (II) iodide in the presence of rac-(1R,2R)-2-aminocyclo-hexan-1-ol and a suitable base such as sodium bis (trimethylsilyl)amide in an appropriate solvent like iPrOH, dioxane, THF or DME, preferably iPrOH at temperatures between room temperature and the boiling point of the solvent, optionally applying microwave heating, to yield intermediates 15. Reactions of this type are described in literature, e.g. *ChemistrySelect.* 2017, 2, 8841 (step a). Removal of the protective group from intermediates 15 applying methods well known in the art and as described under Scheme 2, step c, furnishes intermediates 16 (step b). Amines 16 can be then coupled with intermediates 1 applying for example the conditions outlined under Scheme 1, step a, to give intermediates 2a, in which FG is bromine (step c). The bromo substituent in intermediates 2a can be converted into a boronic acid or boronic ester (e.g. pinacol ester) according to literature procedures as described for example in "Boronic Acids—Preparation and Applications in Organic Synthesis and Medicine" by Dennis G. Hall (ed.) 1st Ed., 2005, John Wiley & Sons, New York) using a suitable catalyst such as $PdC_2(dppf)·CH_2Cl_2$ in the presence of bis(pinacolato)diboron and a suitable base such as $Na_2CO_3$, $NaHCO_3$, KF, KOAc or TEA in an appropriate solvent like dioxane, THF, DME, water or DMF, or mixtures thereof, preferably dioxane at temperatures between room temperature and the boiling point of the solvent, or mixtures thereof, optionally applying microwave heating, to yield intermediates 2c (step d). Finally, hydrolysis of the pinacolyl ester in intermediates 2c can be achieved by methods known in literature (e.g. *Tetrahedron letters* 2005, 46, 7899) or using $NaIO_4$ in presence of $NH_4OAc$ in a mixture of water and acetone at around room temperature to give intermediates 2d (step e).

Compounds 31, 32a and 32b in which $R^1$ to $R^7$, $R^8$, m and n are as described herein, $R^{6a}$ is $C_{1-6}$-alkyl, $L^1$ is a covalent bond, A is phenyl and B is a 1-($C_{1-6}$-alkyl)-substituted pyrazole 3-yl or pyrazole 5-yl, can be prepared by methods well known by a person skilled in the art and as exemplified by the general synthetic procedure outlined in Scheme 5.

Scheme 5

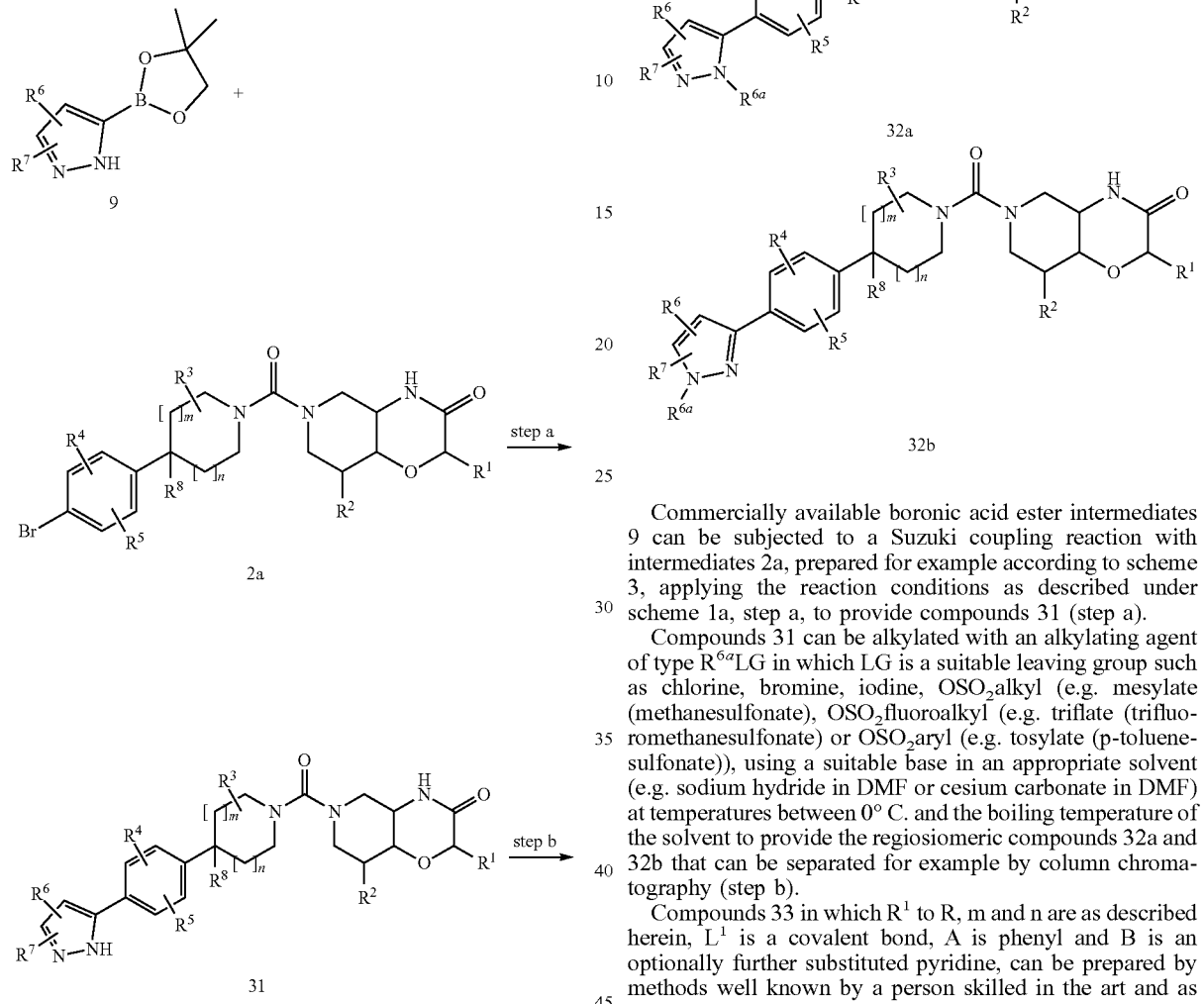

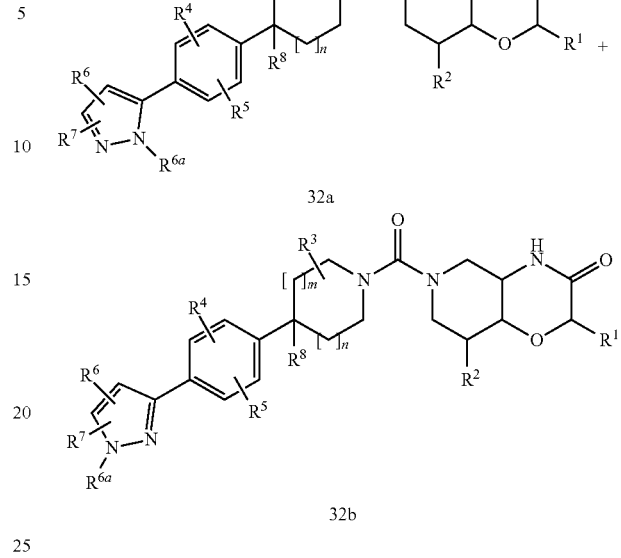

Commercially available boronic acid ester intermediates 9 can be subjected to a Suzuki coupling reaction with intermediates 2a, prepared for example according to scheme 3, applying the reaction conditions as described under scheme 1a, step a, to provide compounds 31 (step a).

Compounds 31 can be alkylated with an alkylating agent of type $R^{6a}LG$ in which LG is a suitable leaving group such as chlorine, bromine, iodine, $OSO_2$alkyl (e.g. mesylate (methanesulfonate), $OSO_2$fluoroalkyl (e.g. triflate (trifluoromethanesulfonate) or $OSO_2$aryl (e.g. tosylate (p-toluenesulfonate)), using a suitable base in an appropriate solvent (e.g. sodium hydride in DMF or cesium carbonate in DMF) at temperatures between 0° C. and the boiling temperature of the solvent to provide the regiosiomeric compounds 32a and 32b that can be separated for example by column chromatography (step b).

Compounds 33 in which $R^1$ to R, m and n are as described herein, $L^1$ is a covalent bond, A is phenyl and B is an optionally further substituted pyridine, can be prepared by methods well known by a person skilled in the art and as exemplified by the general synthetic procedure outlined in Scheme 6.

Scheme 6

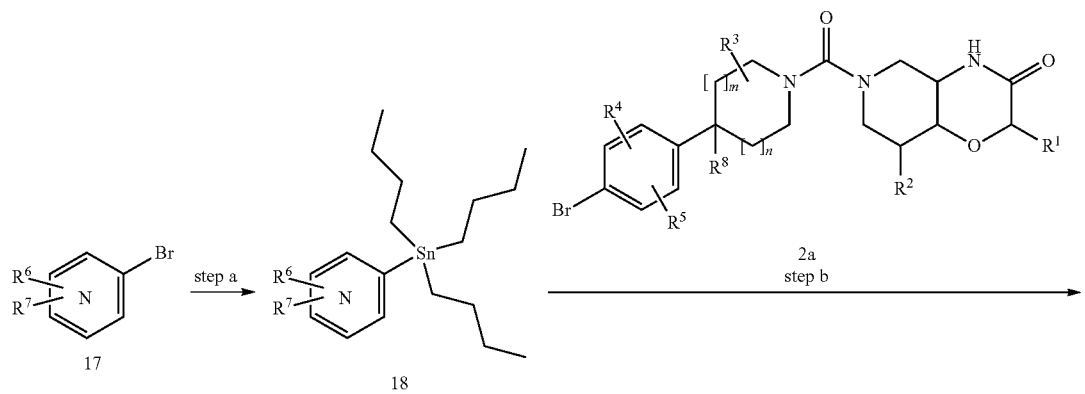

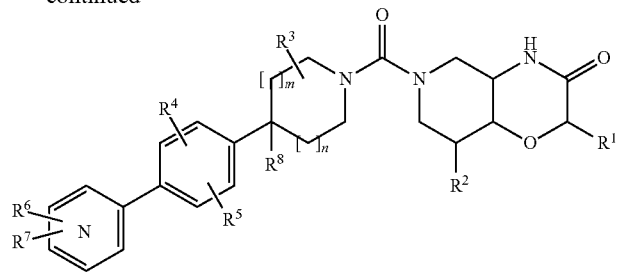

33

The bromine in commercially available 2-bromo-3-chloro-pyridine 17 can be converted into a tri-n-butyltin group by methods known in the art, for example by first carrying out a bromo lithium exchange reaction with n-BuLi in a suitable solvent such as toluene in a temperature range from, e.g. −78° C. to RT and reacting the intermediate lithium species with tri-N-butyltin chloride to provide intermediates 18 (step a).

Intermediates 18 can be reacted with intermediates 2a using a suitable catalyst and solvent such as, e.g. tetrakis(triphenylphosphine)-palladium(0) in DMF at temperatures between room temperature and the boiling point of the solvent or solvent mixture to provide compounds 33 (step a). Stille reactions of that type are well known in the art and described in literature, e.g. Org. React. 1997, 50, 1-652, ACS Catal. 2015, 5, 3040-3053.

In some embodiments, intermediates 2 are intermediates of type 2e. Intermediates of type 2e in which $R^3$, $R^4$, $R^5$, $R^8$, m and n are defined as herein, $R^{6a}$ is $C_{1-6}$-alkyl, $L^1$ is a covalent bond, A is phenyl and B is a 1-alkyl-substituted triazole 5-yl can be prepared by methods well known by a person skilled in the art and as exemplified by the general synthetic procedure outlined in Scheme 7.

Scheme 7

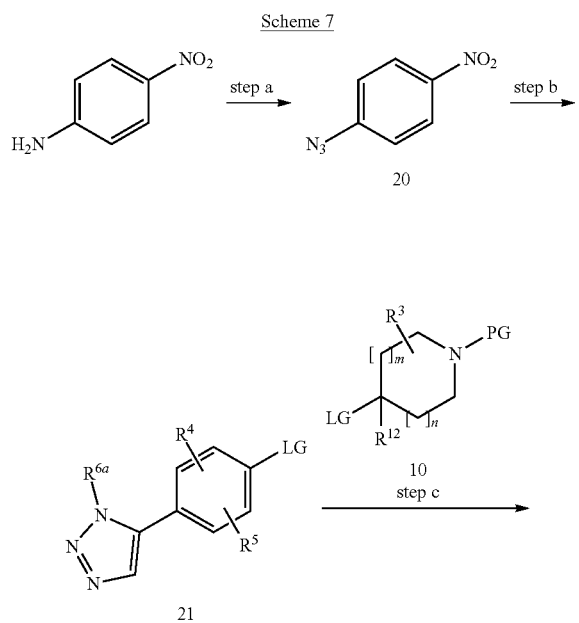

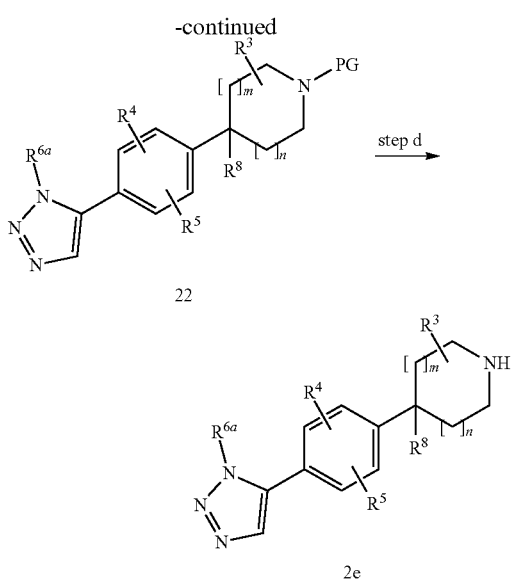

Commercially available 4-nitroaniline can be converted into intermediate 20 by methods known in the art, for example using tert-butyl nitrite and trimethylsilylazide in an appropriate solvent such as ACN (step a).

Reaction of intermediates 20 with an acetophenone (e.g., 4'-bromoacetophenone) and amines of type $R^{6b}$—$NH_2$ in a suitable acid and solvent system such as AcOH in toluene, optionally using molecular sieves preferably at elevated temperatures furnishes triazole intermediates 21, wherein LG is a suitable leaving group, e.g. a halogen, in particular bromo (step b). Reactions of this type have been described in literature, e.g. Chem. Commun., 2016, 52, 2885.

Intermediates 21 can be subjected to a cross-electrophile coupling reaction with commercially available intermediate 10, wherein LG is a suitable leaving group such as bromo or iodo, preferably bromo, m, n and $R^3$ are as described herein and PG is a suitable protecting group, such as Boc, applying for example the reaction conditions described under scheme 1a, step a, to provide intermediates 22 (step c).

Removal of the protecting group using for example TFA in DCM at temperatures between 0° C. and room temperature, yields intermediates 2e (step d).

In some embodiments, intermediates 2 are intermediates of type 2f. Intermediates of type 2f in which $R^3$, $R^4$, $R^5$, $R^8$, m and n are as defined herein, $R^{6a}$ is $C_{1-6}$-alkyl or halo-$C_{1-6}$-alkyl, $R^{6b}$ is hydrogen, $C_{1-6}$-alkyl or halo-$C_{1-6}$-alkyl, $L^1$ is a covalent bond, A is phenyl and B is pyrazole-1-yl can be prepared by methods well known by a person skilled in the art and as exemplified by the general synthetic procedure outlined in Scheme 8.

Scheme 8

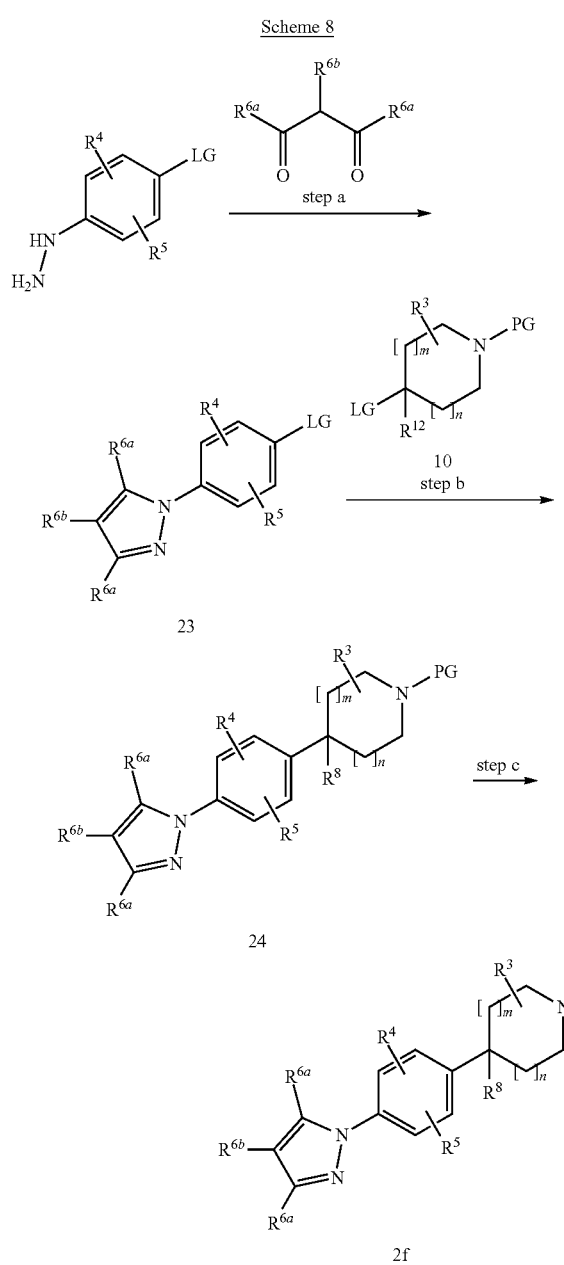

PG = Protecting group

In some embodiments, intermediates 2 are intermediates of type 2g. Intermediates of type 2g in which $R^3$, $R^4$, $R^5$, R, m and n are as defined herein, $R^{6a}$ is $C_{1-6}$-alkyl, $L^1$ is a covalent bond, A is phenyl and B is a 5-substituted-1,3,4-oxadiazol-2-yl can be prepared by methods known by a person skilled in the art and as exemplified by the general synthetic procedure outlined in Scheme 9.

Scheme 9

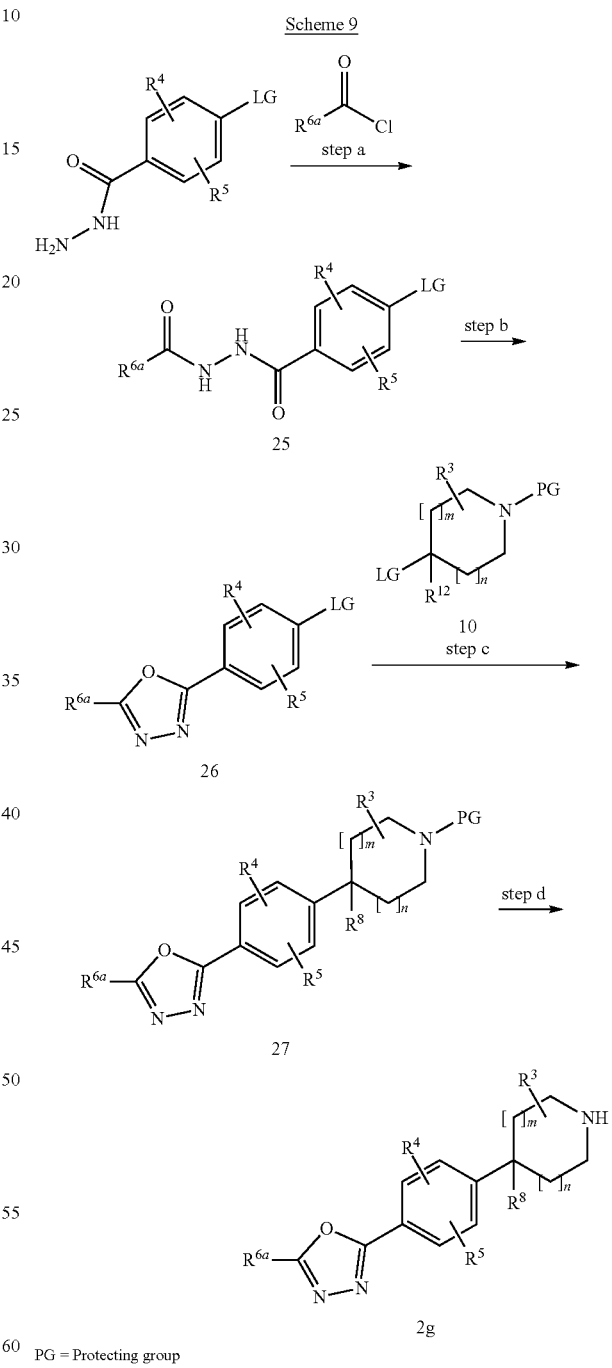

PG = Protecting group

Intermediates 23 can be prepared for example by cyclocondensation of 1,3-dicarbonyl compounds with commercially available and optionally substituted hydrazines (e.g., (4-bromophenyl)hydrazines) in the presence of copper(II) nitrate trihydrate in a suitable solvent such as ACN (step a).

Intermediates 23 can be can be subjected to a cross-electrophile coupling reaction with intermediates of type 10 in which PG signifies a suitable protecting group such as Cbz or Boc, and LG refers to a suitable leaving group, such as a halogen, in particular bromo, applying for example the reaction conditions described under scheme 1a, step a, to provide intermediates 24 (step b).

Removal of the protective group applying published procedures and as described under scheme 7, step d, furnishes intermediates 2f (step c).

Commercially available hydrazides (e.g., 4-bromobenzoic hydrazide) and acid chlorides $R^{6a}C(O)Cl$ can be reacted in the presence of a suitable base in an appropriate solvent such as DIPEA in DCM to yield intermediate 25 (step a).

Intermediates 25, in which LG refers to a suitable leaving group, such as halogen, in particular bromo, can be dehydrated for example using pTsOH in toluene preferably at elevated temperatures up to the boiling point of the solvent to provide intermediates 26 (step b).

Intermediates 26 can be can be subjected for example to a cross-electrophile coupling reaction with intermediates of type 10 applying for example the reaction conditions described under scheme 1a, step a, to provide intermediates 27 (step c).

Removal of the protective group applying published procedures and as described under scheme 7, step d furnishes intermediates 2g (step d).

In some embodiments, intermediates 2 are intermediates of type 2h. Intermediates of type 2h in which in which $R^3$, $R^4$, $R^5$, $R^8$, m and n are as defined herein, $R^{6a}$ is $C_{1-6}$-alkyl, $L^1$ is a covalent bond, A is phenyl and B is a 5-substituted-1,2,4-oxadiazol-3-yl can be prepared by methods well known by a person skilled in the art and as exemplified by the general synthetic procedure outlined in Scheme 10.

Scheme 10

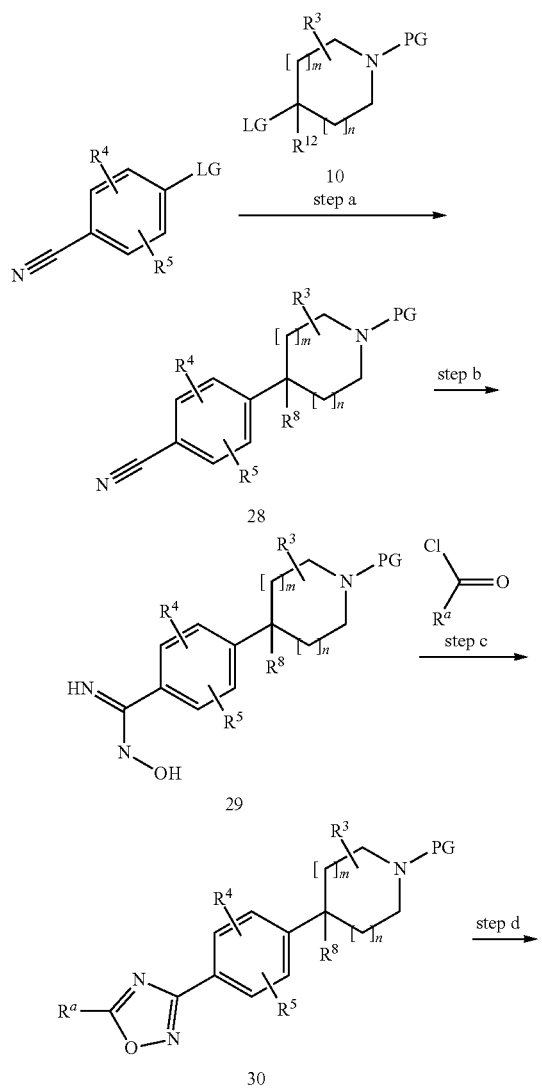

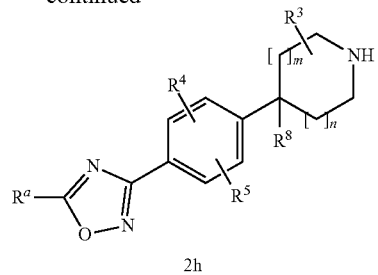

PG = Protecting group

Commercially available or prepared by methods known in the art optionally substituted benzonitriles (e.g., 4-bromobenzonitriles) can be can be subjected to a cross-electrophile coupling reaction with intermediates of type 10 applying for example the reaction conditions described under scheme 1a, step a, to provide intermediates 28 (step a).

Reaction of intermediates 28 with hydroxylamine hydrochloride in a suitable solvent or solvent mixture and using an appropriate base such as $Na_2CO_3$ in EtOH and water, preferably at elevated temperatures, gives the phenylamidoxime intermediates 29 (step b).

Intermediates 29 can then be reacted with acid chlorides $R^{6a}C(O)Cl$ in the presence of a suitable base and solvent such as DIPEA in toluene at temperatures ranging from RT to the boiling point of the solvent or solvent mixture to provide intermediates 30 (step c).

Removal of the protective group applying published procedures and as described under scheme 7, step d, furnishes intermediates 2h (step d).

In one aspect, the present invention provides a process of manufacturing the compounds of formula (I) as described herein, comprising:
reacting 4a,5,6,7,8,8a-hexahydro-4H-pyrido[4,3-b][1,4] oxazin-3-ones 1, wherein $R^1$ and $R^2$ are as defined herein,

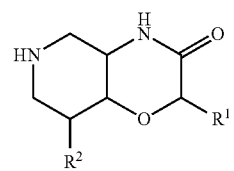

with a heterocyclic amine 2, wherein A, B, $L^1$, X, m, n, and $R^3$ to $R^7$ are as defined herein

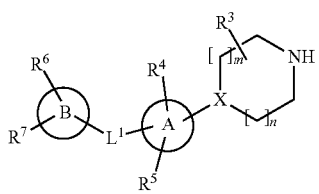

in the presence of a base and a urea forming reagent, to form said compounds of formula (I).

In one embodiment, there is provided a process according to the invention, wherein said base is sodium bicarbonate.

In one embodiment, there is provided a process according to the invention, wherein said urea forming reagent is selected from bis(trichloromethyl) carbonate, phosgene, trichloromethyl chloroformate, (4-nitrophenyl)carbonate and 1,1'-carbonyldiimidazole, preferably wherein said urea forming reagent is bis(trichloromethyl) carbonate.

In one aspect, the present invention provides a compound of formula (I) as described herein, when manufactured according to any one of the processes described herein.

MAGL Inhibitory Activity

Compounds of the present invention are MAGL inhibitors. Thus, in one aspect, the present invention provides the use of compounds of formula (I) as described herein for inhibiting MAGL in a mammal.

In a further aspect, the present invention provides compounds of formula (I) as described herein for use in a method of inhibiting MAGL in a mammal.

In a further aspect, the present invention provides the use of compounds of formula (I) as described herein for the preparation of a medicament for inhibiting MAGL in a mammal.

In a further aspect, the present invention provides a method for inhibiting MAGL in a mammal, which method comprises administering an effective amount of a compound of formula (I) as described herein to the mammal.

Compounds of formula (I) were profiled for MAGL inhibitory activity by determining the enzymatic activity by following the hydrolysis of the natural substrate 2-arachidonoylglycerol (2-AG) resulting in arachidonic acid, which can be followed by mass spectrometry. This assay is hereinafter abbreviated "2-AG assay".

The 2-AG assay was carried out in 384 well assay plates (PP, Greiner Cat #784201) in a total volume of 20 µL. Compound dilutions were made in 100% DMSO (VWR Chemicals 23500.297) in a polypropylene plate in 3-fold dilution steps to give a final concentration range in the assay from 12.5 µM to 0.8 µM. 0.25 µL compound dilutions (100% DMSO) were added to 9 µL MAGL in assay buffer (50 mM TRIS (GIBCO, 15567-027), 1 mM EDTA (Fluka, 03690-100 mL), 0.01% (v/v) Tween. After shaking, the plate was incubated for 15 min at RT. To start the reaction, 10 µL 2-arachidonoylglycerol in assay buffer was added. The final concentrations in the assay was 50 µM MAGL and 8 µM 2-arachidonoylglyerol. After shaking and 30 min incubation at RT, the reaction was quenched by the addition of 40 µL of ACN containing 4 µM of d8-arachidonic acid. The amount of arachidonic acid was traced by an online SPE system (Agilent Rapidfire) coupled to a triple quadrupole mass spectrometer (Agilent 6460). A C18 SPE cartridge (G9205A) was used in an ACN/water liquid setup. The mass spectrometer was operated in negative electrospray mode following the mass transitions 303.1→259.1 for arachidonic acid and 311.1→267.0 for d8-arachidonic acid. The activity of the compounds was calculated based on the ratio of intensities [arachidonic acid/d8-arachidonic acid].

TABLE 1

| Example | $IC_{50}$ MAGL [nM] |
|---|---|
| 1 | 0.2 |
| 2 | 0.02 |
| 3 | 75.4 |
| 4 | 2.5 |
| 5 | 23.8 |
| 6 | 132.8 |
| 7 | 0.5 |
| 8 | 4.3 |
| 9 | 0.9 |
| 10 | 2.3 |
| 11 | 42.9 |
| 12 | 23.5 |
| 13 | 12.7 |
| 14 | 13.4 |
| 15 | 0.11 |
| 16 | 0.05 |
| 17 | 0.10 |
| 18 | 0.05 |
| 19 | 0.01 |
| 20 | 0.06 |
| 21 | 0.03 |
| 22 | 0.06 |
| 23 | 0.2 |
| 24 | 0.04 |
| 25 | 4.2 |
| 26 | 3.9 |
| 27 | 0.3 |
| 28 | 6.3 |
| 29 | 90.9 |
| 30 | 0.7 |
| 31 | 91.9 |
| 32a | 0.2 |
| 32b | 6.5 |
| 33 | 2.7 |
| 34 | 22.9 |
| 35 | 17.4 |
| 36 | 0.9 |
| 37 | 2.4 |
| 38 | 8.5 |
| 39 | 6.7 |
| 40 | 73.1 |
| 41 | 24.6 |
| 42 | 153.2 |
| 43 | 19.3 |
| 44 | 67.7 |
| 45 | 133.7 |
| 46 | 17.5 |
| 47 | 1.4 |
| 48 | 31.5 |
| 49 | 2.4 |
| 50 | 4.3 |
| 51 | 123.8 |
| 52 | 1.3 |
| 53 | 12.9 |
| 54 | 10.4 |
| 55 | 10.3 |
| 56 | 15.5 |
| 57 | 17.8 |
| 58 | 1096.3 |

In one aspect, the present invention provides compounds of formula (I) and their pharmaceutically acceptable salts or esters as described herein, wherein said compounds of formula (I) and their pharmaceutically acceptable salts or esters have $IC_{50}$'s for MAGL inhibition below 25 µM, preferably below 10 µM, more preferably below 5 µM as measured in the MAGL assay described herein.

In one embodiment, compounds of formula (I) and their pharmaceutically acceptable salts or esters as described herein have $IC_{50}$ (MAGL inhibition) values between 0.000001 µM and 25 µM, particular compounds have $IC_{50}$ values between 0.000005 µM and 10 µM, further particular compounds have $IC_{50}$ values between 0.00005 µM and 5 µM, as measured in the MAGL assay described herein.

Using the Compounds of the Invention

In one aspect, the present invention provides compounds of formula (I), or pharmaceutically acceptable salts thereof, as described herein for use as therapeutically active substance.

In a further aspect, the present invention provides the use of compounds of formula (I), or pharmaceutically acceptable salts thereof, as described herein for the treatment or prophylaxis of neuroinflammation, neurodegenerative diseases, pain, cancer, mental disorders and/or inflammatory bowel disease in a mammal.

In one embodiment, the present invention provides the use of compounds of formula (I), or pharmaceutically acceptable salts thereof, as described herein for the treatment or prophylaxis of neuroinflammation and/or neurodegenerative diseases in a mammal.

In one embodiment, the present invention provides the use of compounds of formula (I), or pharmaceutically acceptable salts thereof, as described herein for the treatment or prophylaxis of neurodegenerative diseases in a mammal.

In one embodiment, the present invention provides the use of compounds of formula (I), or pharmaceutically acceptable salts thereof, as described herein for the treatment or prophylaxis of cancer in a mammal.

In one embodiment, the present invention provides the use of compounds of formula (I), or pharmaceutically acceptable salts thereof, as described herein for the treatment or prophylaxis of inflammatory bowel disease in a mammal.

In one embodiment, the present invention provides the use of compounds of formula (I), or pharmaceutically acceptable salts thereof, as described herein for the treatment or prophylaxis of pain in a mammal.

In one aspect, the present invention provides the use of compounds of formula (I), or pharmaceutically acceptable salts thereof, as described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal.

In a preferred embodiment, the present invention provides the use of compounds of formula (I), or pharmaceutically acceptable salts thereof, as described herein for the treatment or prophylaxis of multiple sclerosis, Alzheimer's disease and/or Parkinson's disease in a mammal.

In a particularly preferred embodiment, the present invention provides the use of compounds of formula (I), or pharmaceutically acceptable salts thereof, as described herein for the treatment or prophylaxis of multiple sclerosis in a mammal.

In one aspect, the present invention provides compounds of formula (I), or pharmaceutically acceptable salts thereof, as described herein for use in the treatment or prophylaxis of neuroinflammation, neurodegenerative diseases, pain, cancer, mental disorders and/or inflammatory bowel disease in a mammal.

In one embodiment, the present invention provides compounds of formula (I), or pharmaceutically acceptable salts thereof, as described herein for use in the treatment or prophylaxis of neuroinflammation and/or neurodegenerative diseases in a mammal.

In one embodiment, the present invention provides compounds of formula (I), or pharmaceutically acceptable salts thereof, as described herein for use in the treatment or prophylaxis of neurodegenerative diseases in a mammal.

In one embodiment, the present invention provides compounds of formula (I), or pharmaceutically acceptable salts thereof, as described herein for use in the treatment or prophylaxis of cancer in a mammal.

In one embodiment, the present invention provides compounds of formula (I), or pharmaceutically acceptable salts thereof, as described herein for use in the treatment or prophylaxis of inflammatory bowel disease in a mammal.

In one embodiment, the present invention provides compounds of formula (I), or pharmaceutically acceptable salts thereof, as described herein for use in the treatment or prophylaxis of pain in a mammal.

In one aspect, the present invention provides compounds of formula (I), or pharmaceutically acceptable salts thereof, as described herein for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal.

In a preferred embodiment, the present invention provides compounds of formula (I), or pharmaceutically acceptable salts thereof, as described herein for use in the treatment or prophylaxis of multiple sclerosis, Alzheimer's disease and/or Parkinson's disease in a mammal.

In a particularly preferred embodiment, the present invention provides compounds of formula (I), or pharmaceutically acceptable salts thereof, as described herein for use in the treatment or prophylaxis of multiple sclerosis in a mammal.

In one aspect, the present invention provides the use of compounds of formula (I), or pharmaceutically acceptable salts thereof, as described herein for the preparation of a medicament for the treatment or prophylaxis of neuroinflammation, neurodegenerative diseases, pain, cancer, mental disorders and/or inflammatory bowel disease in a mammal.

In one embodiment, the present invention provides the use of compounds of formula (I), or pharmaceutically acceptable salts thereof, as described herein for the preparation of a medicament for the treatment or prophylaxis of neuroinflammation and/or neurodegenerative diseases in a mammal.

In one embodiment, the present invention provides the use of compounds of formula (I), or pharmaceutically acceptable salts thereof, as described herein for the preparation of a medicament for the treatment or prophylaxis of neurodegenerative diseases in a mammal.

In one embodiment, the present invention provides the use of compounds of formula (I), or pharmaceutically acceptable salts thereof, as described herein for the preparation of a medicament for the treatment or prophylaxis of cancer in a mammal.

In one embodiment, the present invention provides the use of compounds of formula (I), or pharmaceutically acceptable salts thereof, as described herein for the preparation of a medicament for the treatment or prophylaxis of inflammatory bowel disease in a mammal.

In one embodiment, the present invention provides the use of compounds of formula (I), or pharmaceutically acceptable salts thereof, as described herein for the preparation of a medicament for the treatment or prophylaxis of pain in a mammal.

In a further aspect, the present invention provides the use of compounds of formula (I), or pharmaceutically acceptable salts thereof, as described herein for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal.

In a preferred embodiment, the present invention provides the use of compounds of formula (I), or pharmaceutically acceptable salts thereof, as described herein for the preparation of a medicament for the treatment or prophylaxis of multiple sclerosis, Alzheimer's disease and/or Parkinson's disease in a mammal.

In a particularly preferred embodiment, the present invention provides the use of compounds of formula (I), or pharmaceutically acceptable salts thereof, as described herein for the preparation of a medicament for the treatment or prophylaxis of multiple sclerosis in a mammal.

In one aspect, the present invention provides a method for the treatment or prophylaxis of neuroinflammation, neurodegenerative diseases, pain, cancer, mental disorders and/or inflammatory bowel disease in a mammal, which method comprises administering an effective amount of a compound of formula (I), or a pharmaceutically acceptable salt thereof, as described herein to the mammal.

In one embodiment, the present invention provides a method for the treatment or prophylaxis of neuroinflammation and/or neurodegenerative diseases in a mammal, which method comprises administering an effective amount of a compound of formula (I), or a pharmaceutically acceptable salt thereof, as described herein to the mammal.

In one embodiment, the present invention provides a method for the treatment or prophylaxis of neurodegenerative diseases in a mammal, which method comprises administering an effective amount of a compound of formula (I), or a pharmaceutically acceptable salt thereof, as described herein to the mammal.

In one embodiment, the present invention provides a method for the treatment or prophylaxis of cancer in a mammal, which method comprises administering an effective amount of a compound of formula (I), or a pharmaceutically acceptable salt thereof, as described herein to the mammal.

In one embodiment, the present invention provides a method for the treatment or prophylaxis of inflammatory bowel disease in a mammal, which method comprises administering an effective amount of a compound of formula (I), or a pharmaceutically acceptable salt thereof, as described herein to the mammal.

In one embodiment, the present invention provides a method for the treatment or prophylaxis of pain in a mammal, which method comprises administering an effective amount of a compound of formula (I), or a pharmaceutically acceptable salt thereof, as described herein to the mammal.

In a further aspect, the present invention provides a method for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain, spasticity associated with pain, abdominal pain, abdominal pain associated with irritable bowel syndrome and/or visceral pain in a mammal, which method comprises administering an effective amount of a compound of formula (I), or a pharmaceutically acceptable salt thereof, as described herein to the mammal.

In a preferred embodiment, the present invention provides a method for the treatment or prophylaxis of multiple sclerosis, Alzheimer's disease and/or Parkinson's disease in a mammal, which method comprises administering an effective amount of a compound of formula (I), or a pharmaceutically acceptable salt thereof, as described herein to the mammal.

In a particularly preferred embodiment, the present invention provides a method for the treatment or prophylaxis of multiple sclerosis in a mammal, which method comprises administering an effective amount of a compound of formula (I), or a pharmaceutically acceptable salt thereof, as described herein to the mammal.

Pharmaceutical Compositions and Administration

In one aspect, the present invention provides a pharmaceutical composition comprising a compound of formula (I) as described herein and a therapeutically inert carrier.

In one embodiment, there is provided a pharmaceutical composition according to Example 47 or 48.

The compounds of formula (I) and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

Method A1

Example 1

(4aR,8aS)-6-(3-(4-Phenoxyphenyl)azetidine-1-carbonyl)hexahydro-2H-pyrido[4,3-b][1,4]oxazin-3(4H)-one

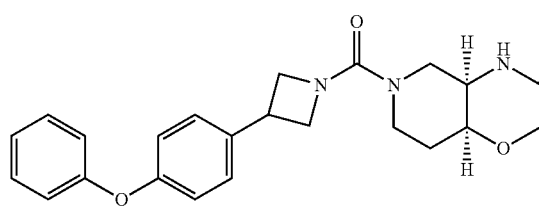

In a sealed tube, (4aR,8aS)-6-[3-(4-bromophenyl)azetidine-1-carbonyl]-4,4a,5,7,8,8a-hexahydropyrido[4,3-b][1,4]oxazin-3-one (BB4 step c, 0.04 g, 0.110 mmol), phenol (0.014, 0.152 mmol), Pd(OAc)$_2$ (0.004 g, 0.016 mmol), 2-di-tert-butylphosphino-2',4',6'-triisopropylbiphenyl (0.01 g, 0.024 mmol) and K$_3$PO$_4$ (0.043 g, 0.203 mmol) were mixed in toluene (0.68 mL). The reaction mixture was heated to 100° C. over night. The mixture was diluted with EtOAc, poured into water and the aqueous layer was extracted with EtOAc. The organic layer was washed with brine, dried over Na$_2$SO$_4$, filtered and evaporated. The residue was purified by preparative HPLC to give the title compound (0.008, 17%) as an off white foam. MS (ESI): m/z=408.2 [M+H]$^+$.

Method A2

Example 2

(4aR,8aS)-6-[3-[4-(2-Chlorophenoxy)phenyl]azetidine-1-carbonyl]-4,4a,5,7,8,8a-hexahydropyrido[4,3-b][1,4]oxazin-3-one

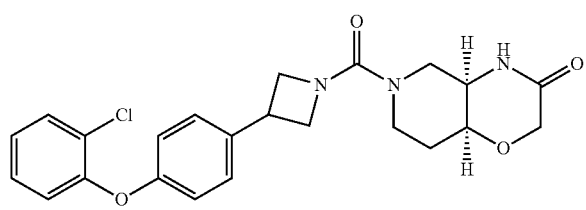

To a solution of 4-[1-[(4aR,8aS)-3-oxo-4,4a,5,7,8,8a-hexahydropyrido[4,3-b][1,4]oxazine-6-carbonyl]azetidin-3-yl]phenyl]boronic acid (BB4, 0.025 g, 0.07 mmol), 2-chlorophenol (0.027 g, 0.21 mmol) and TEA (0.043 mL, 0.42 mmol) in MeCN (2 mL) was added 4A molecular sieves (0.03 g) and cupric acetate anhydrous (0.038 g, 0.21 mmol). The reaction mixture was stirred at 30° C. under O$_2$ atmosphere for 16 hours. The mixture was quenched with NH$_4$OH (0.3 mL) and H$_2$O (2 mL), and extracted with EtOAc (3×2 mL). The combined organic layers were evaporated to dryness and the residue was purified by preparative HPLC to yield the title product (0.007 g, 23%) as off-white solid. MS (ESI): m/z=442.1 [M+H]$^+$.

Method A3

Example 3

(4aR,8aS)-6-[3-(4-Pyrimidin-2-yloxyphenyl)azetidine-1-carbonyl]-4,4a,5,7,8,8a-hexahydropyrido[4,3-b][1,4]oxazin-3-one

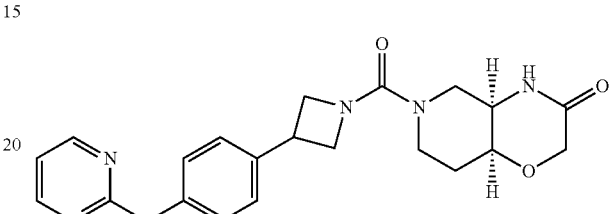

In a sealed tube, (4aR,8aS)-6-[3-(4-hydroxyphenyl)azetidine-1-carbonyl]-4,4a,5,7,8,8a-hexahydropyrido[4,3-b][1,4]oxazin-3-one (BB3, 0.05 g, 0.150 mmol), 2-chloro-pyrimidine (0.026 g, 0.230 mmol, CAS RN 1722-12-9) and potassium carbonate (0.062 g, 0.450 mmol, CAS RN 584-08-7) were mixed in DMSO (2.5 mL). The reaction mixture was then heated to 80° C. for 12 hours. The mixture was diluted with EtOAc, poured into water and the aqueous layer was extracted with EtOAc. The organic layer was washed with brine, dried over Na$_2$SO$_4$, filtered and evaporated. The residue was purified by preparative HPLC to yield the title product (0.039 g, 63%) as white solid. MS (ESI): m/z=410.4 [M+H]$^+$.

Method A4

Example 4

(4aR,8aS)-6-[3-[4-[(2-Methyl-3-pyridyl)oxy]phenyl]azetidine-1-carbonyl]-4,4a,5,7,8,8a-hexahydropyrido[4,3-b][1,4]oxazin-3-one

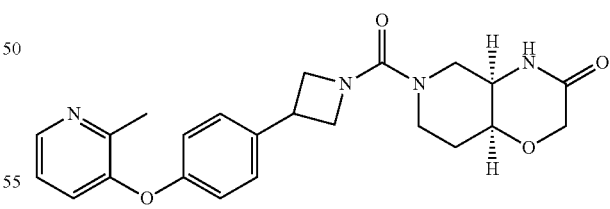

In a sealed tube, (4aR,8aS)-6-[3-(4-hydroxyphenyl)azetidine-1-carbonyl]-4,4a,5,7,8,8a-hexahydropyrido[4,3-b][1,4]oxazin-3-one (BB3, 0.050 g, 0.150 mmol), 3-fluoro-2-methyl-pyridine (0.046 g, 0.410 mmol) and Cs$_2$CO$_3$ (0.197 g, 0.6 mmol) were mixed in NMP (2 mL). The reaction mixture was then heated under microwave irradiation at 200° C. for 1 hour. The mixture was diluted with EtOAc, poured into water and the aqueous layer was extracted with EtOAc. The organic layer was washed with brine, dried over Na$_2$SO$_4$, filtered and evaporated. The residue was purified by preparative HPLC to give the desired product (0.007 g, 11%) as white solid. MS (ESI): m/z=423.1 [M+H]+.
Method B1

Example 30

(4aR,8aS)-6-[3-[4-[(3,6-Dimethyl-2-pyridyl)oxy]phenyl]azetidine-1-carbonyl]-4,4a,5,7,8,8a-hexahydropyrido[4,3-b][1,4]oxazin-3-one

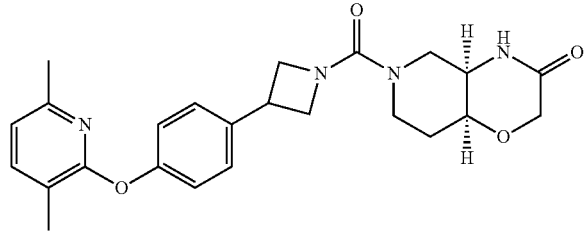 [SMILES: Cc1ccc(C)c(Oc2ccc(C3CN(C(=O)N4CC[C@@H]5OCC(=O)N[C@@H]5C4)C3)cc2)n1]

To a solution of methylboronic acid (0.014 g, 0.24 mmol), K$_2$CO$_3$ (0.066 g, 0.48 mmol) and (4aR,8aS)-6-[3-[4-[(3-bromo-6-methyl-2-pyridyl)oxy]phenyl]azetidine-1-carbonyl]-4,4a,5,7,8,8a-hexahydropyrido[4,3-b][1,4]oxazin-3-one (0.06 g, 0.12 mmol) in dioxane (2 mL) and water (0.5 mL) was added Pd(dppf)Cl$_2$ (0.008 g, 0.01 mmol) and the reaction mixture was heated to 100° C. for 12 hours. The mixture was filtered, the filtrate diluted with water (10 mL) and extracted with EtOAc (3×5 mL). The combined organic phase was washed with brine, dried over Na$_2$SO$_4$, filtered and evaporated to dryness. The residue was purified by preparative HPLC to give title product (0.009 g, 16%) as off-white solid. MS (ESI): m/z=437.2 [M+H]+.

Step a) (4aR,8aS)-6-[3-[4-[(3-Bromo-6-methyl-2-pyridyl)oxy]phenyl]azetidine-1-carbonyl]-4,4a,5,7,8,8a-hexahydropyrido[4,3-b][1,4]oxazin-3-one

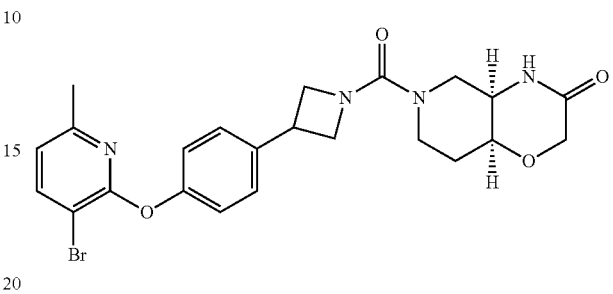

To a solution of (4aR,8aS)-6-[3-(4-hydroxyphenyl)azetidine-1-carbonyl]-4,4a,5,7,8,8a-hexahydropyrido[4,3-b][1,4]oxazin-3-one (BB3, 0.1 g, 0.3 mmol), Cs$_2$CO$_3$ (0.394 g, 1.21 mmol) in DMSO (5 mL) was added 3-bromo-2-fluoro-6-methyl-pyridine (0.086 g, 0.45 mmol) and the reaction mixture was heated to 50° C. for 12 hours. The mixture was filtered and the filtrate purified by preparative HPLC to give the title product (0.08 g, 53%) as colorless foam. MS (ESI): m/z=503.2 [M+2+H]+.

The following examples listed in Table 2 were prepared in analogy to the reaction methods described herein by using the indicated intermediates and commercial compounds

TABLE 2

| Ex. | Systematic Name/Structure | Building block | MS, m/z | Method |
|---|---|---|---|---|
| 5 | (+)-(4aR,8aS)-6-[3-[4-(4-Methylpyrimidin-2-yl)oxyphenyl]azetidine-1-carbonyl]-4,4a,5,7,8,8a-hexahydropyrido[4,3-b][1,4]oxazin-3-one<br />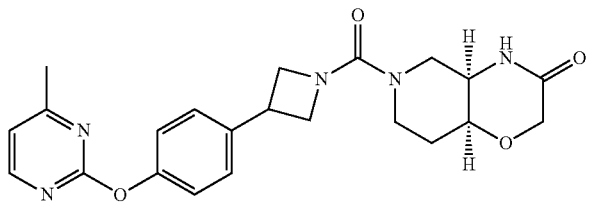 | BB3 and 2-Chloro-4-methylpyrimidine CAS RN 13036-57-2 | 424.4 [M + H]+ | A3 |
| 6 | (+)-(4aR,8aS)-6-[3-(4-Pyridazin-3-yloxyphenyl)azetidine-1-carbonyl]-4,4a,5,7,8,8a-hexahydropyrido[4,3-b][1,4]oxazin-3-one<br />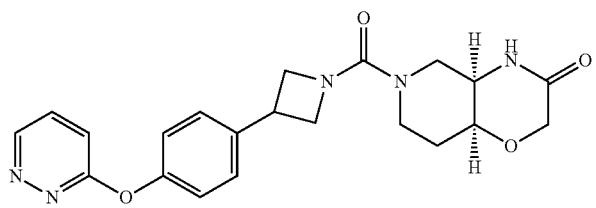 [SMILES: O=C1CO[C@H]2CCN(C(=O)N3CC(c4ccc(Oc5cccnn5)cc4)C3)C[C@H]2N1] | BB3 and 3-Chloropyridazine hydrochloride CAS RN 1120-95-2 | 410.1 [M + H]+ | A3 |

TABLE 2-continued

| Ex. | Systematic Name/Structure | Building block | MS, m/z | Method |
|---|---|---|---|---|
| 7 | (+)-(4aR,8aS)-6-[3-[4-[(4-Methyl-3-pyridyl)oxy]phenyl]azetidine-1-carbonyl]-4,4a,5,7,8,8a-hexahydropyrido[4,3-b][1,4]oxazin-3-one | BB3 and 3-Fluoro-4-methylpyridine | 423.1 [M + H]+ | A4 |
| 8 | (+)-(4aR,8aS)-6-[3-[4-[(5-Fluoro-3-pyridyl)oxy]phenyl]azetidine-1-carbonyl]-4,4a,5,7,8,8a-hexahydropyrido[4,3-b][1,4]oxazin-3-one | BB3 and 3,5-Difluoropyridine | 427.1 [M + H]+ | A4 |
| 9 | (+)-(4aR,8aS)-6-[3-[4-[(5-Chloro-3-pyridyl)oxy]phenyl]azetidine-1-carbonyl]-4,4a,5,7,8,8a-hexahydropyrido[4,3-b][1,4]oxazin-3-one | BB3 and 3-Chloro-5-fluoro-pyridine | 443.1 [M + H]+ | A4 |
| 10 | (+)-(4aR,8aS)-6-[3-[4-(3-Pyridyloxy)phenyl]azetidine-1-carbonyl]-4,4a,5,7,8,8a-hexahydropyrido[4,3-b][1,4]oxazin-3-one | BB3 and 3-Fluoropyridine | 409.1 [M + H]+ | A4 |
| 11 | (+)-(4aR,8aS)-6-[3-[4-(4-Methylpyridazin-3-yl)oxyphenyl]azetidine-1-carbonyl]-4,4a,5,7,8,8a-hexahydropyrido[4,3-b][1,4]oxazin-3-one | BB3 and 3-Chloro-4-methyl-pyridazine CAS RN 68206-04-2 | 424.5 [M + H]+ | A3* *heated to 130° C. |

TABLE 2-continued

| Ex. | Systematic Name/Structure | Building block | MS, m/z | Method |
|---|---|---|---|---|
| 12 | (+)-(4aR,8aS)-6-[3-[4-(3-Chloropyridazin-4-yl)oxyphenyl]azetidine-1-carbonyl]-4,4a,5,7,8,8a-hexahydropyrido[4,3-b][1,4]oxazin-3-one | BB3 and 3,4-Dichloropyridazine CAS RN 1677-80-1 | 444.4 [M + H]+ | A3 |
| 13 | (+)-(4aR,8aS)-6-[3-[4-(4-Methoxypyrimidin-2-yl)oxyphenyl]azetidine-1-carbonyl]-4,4a,5,7,8,8a-hexahydropyrido[4,3-b][1,4]oxazin-3-one | BB3 and 2-Chloro-4-methoxypyrimidine CAS RN 22536-63-6 | 440.4 [M + H]+ | A3 |
| 14 | (+)-(4aR,8aS)-6-[3-[4-[4-(Trifluoromethyl)pyrimidin-2-yl]oxyphenyl]azetidine-1-carbonyl]-4,4a,5,7,8,8a-hexahydropyrido[4,3-b][1,4]oxazin-3-one | BB3 and 2-Chloro-4-trifluoromethyl)pyrimidine CAS RN 33034-67-2 | 478.3 [M + H]+ | A3 |
| 15 | (+)-(4aR,8aS)-6-[3-[4-(3-Fluorophenoxy)phenyl]azetidine-1-carbonyl]-4,4a,5,7,8,8a-hexahydropyrido[4,3-b][1,4]oxazin-3-one | BB4 and 3-Fluorophenol | 426.2 [M + H]+ | A2 |

TABLE 2-continued

| Ex. | Systematic Name/Structure | Building block | MS, m/z | Method |
|---|---|---|---|---|
| 16 | (+)-(4aR,8aS)-6-[3-[4-(4-Fluorophenoxy)phenyl]azetidine-1-carbonyl]-4,4a,5,7,8,8a-hexahydropyrido[4,3-b][1,4]oxazin-3-one | BB4 and 4-Fluorophenol | 426.1 [M + H]+ | A2 |
| 17 | (+)-(4aR,8aS)-6-[3-[4-(2,4-Difluorophenoxy)phenyl]azetidine-1-carbonyl]-4,4a,5,7,8,8a-hexahydropyrido[4,3-b][1,4]oxazin-3-one | BB4 and 2,4-Difluorophenol | 444.1 [M + H]+ | A2 |
| 18 | (+)-(4aR,8aS)-6-[3-[4-(2-fluorophenoxy)phenyl]azetidine-1-carbonyl]-4,4a,5,7,8,8a-hexahydropyrido[4,3-b][1,4]oxazin-3-one | BB4 and 2-Fluorophenol | 442.1 [M + H]+ | A2 |
| 19 | (+)-(4aR,8aS)-6-[3-[4-(4-Chlorophenoxy)phenyl]azetidine-1-carbonyl]-4,4a,5,7,8,8a-hexahydropyrido[4,3-b][1,4]oxazin-3-one | BB4 and 4-Chlorophenol | 426.1 [M + H]+ | A2 |
| 20 | (+)-(4aR,8aS)-6-[3-[4-(3-Chlorophenoxy)phenyl]azetidine-1-carbonyl]-4,4a,5,7,8,8a-hexahydropyrido[4,3-b][1,4]oxazin-3-one | BB4 and 3-Clorophenol | 442.1 [M + H]+ | A2 |

TABLE 2-continued

| Ex. | Systematic Name/Structure | Building block | MS, m/z | Method |
|---|---|---|---|---|
| 21 | (+)-(4aR,8aS)-6-[3-[4-(2-Methylphenoxy)phenyl]azetidine-1-carbonyl]-4,4a,5,7,8,8a-hexahydropyrido[4,3-b][1,4]oxazin-3-one | BB4 and 2-Methylphenol | 422.2 [M + H]+ | A2 |
| 22 | (+)-(4aR,8aS)-6-[3-[4-[3-(Trifluoromethyl)phenoxy]phenyl]azetidine-1-carbonyl]-4,4a,5,7,8,8a-hexahydropyrido[4,3-b][1,4]oxazin-3-one | BB4 and 3-Trifluoromethylphenol | 476.2 [M + H]+ | A2 |
| 23 | (+)-2-[4-[1-[(4aR,8aS)-3-Oxo-4,4a,5,7,8,8a-hexahydropyrido[4,3-b][1,4]oxazine-6-carbonyl]azetidin-3-yl]phenoxy]benzonitrile | BB3 and 2-Fluorobenzonitrile | 433.2 [M + H]+ | A4* *stirred at 25° C. no MW |
| 24 | (+)-(4aR,8aS)-6-[3-[4-(2-Chloropyrimidin-4-yl)oxyphenyl]azetidine-1-carbonyl]-4,4a,5,7,8,8a-hexahydropyrido[4,3-b][1,4]oxazin-3-one | BB3 and 4-Bromo-2-chloro-pyrimidine CAS RN 885702-34-1 | 444.2 [M + H]+ | A3* *stirred at 25° C. in DMF |

TABLE 2-continued

| Ex. | Systematic Name/Structure | Building block | MS, m/z | Method |
|---|---|---|---|---|
| 25 | (+)-(4aR,8aS)-6-[3-[4-(4-Cyclopropylpyrimidin-2-yl)oxyphenyl]azetidine-1-carbonyl]-4,4a,5,7,8,8a-hexahydropyrido[4,3-b][1,4]oxazin-3-one | BB3 and 2-Chloro-4-cyclopropylpyrimidine CAS RN 954237-31-1 | 450.4 [M + H]+ | A3* *heated to 50° C. in DMF |
| 26 | (+)-(4aR,8aS)-6-[3-[4-[(6-Methyl-2-pyridyl)oxy]phenyl]azetidine-1-carbonyl]-4,4a,5,7,8,8a-hexahydropyrido[4,3-b][1,4]oxazin-3-one | BB3 and 2-Fluoro-6-methylpyridine | 423.2 [M + H]+ | B1 step a) |
| 27 | (+)-(4aR,8aS)-6-[3-[4-[(4-chloro-3-pyridyl)oxy]phenyl]azetidine-1-carbonyl]-4,4a,5,7,8,8a-hexahydropyrido[4,3-b][1,4]oxazin-3-one | BB3 and 4-Chloro-3-fluoropyridine | 443.1 [M + H]+ | A4* *heated to 100° C. |
| 28 | (+)-(4aR,8aS)-6-[3-[4-[(3-Fluoro-4-pyridyl)oxy]phenyl]azetidine-1-carbonyl]-4,4a,5,7,8,8a-hexahydropyrido[4,3-b][1,4]oxazin-3-one | BB3 and 4-Chloro-3-fluoropyridine | 427.1 [M + H]+ | A4* *heated to 100° C. |

TABLE 2-continued

| Ex. | Systematic Name/Structure | Building block | MS, m/z | Method |
| --- | --- | --- | --- | --- |
| 29 | (+)-(4aR,8aS)-6-[3-[4-(2-Methylsulfonylpyrimidin-4-yl)oxyphenyl]azetidine-1-carbonyl]-4,4a,5,7,8,8a-hexahydropyrido[4,3-b][1,4]oxazin-3-one | BB3 and 4-Chloro-2-(methylsulfonyl)pyrimidine CAS RN 97229-11-3 | 488.1 [M + H]+ | A3* *stirred at 0° C. in DMF |

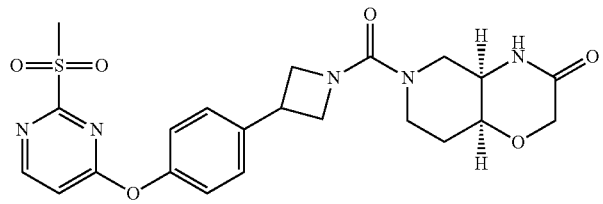 [SMILES: CS(=O)(=O)c1nccc(Oc2ccc(C3CN(C(=O)N4CC[C@@H]5OCC(=O)N[C@@H]5C4)C3)cc2)n1]

Example 31

(4aR,8aS)-6-[3-[4-(1H-Pyrazol-5-yl)phenyl]azetidine-1-carbonyl]-4,4a,5,7,8,8a-hexahydropyrido[4,3-b][1,4]oxazin-3-one

Examples 32a and 32b (4aR,8aS)-6-[3-[4-[2-(2,2-Dimethylpropyl)pyrazol-3-yl]phenyl]azetidine-1-carbonyl]-4,4a,5,7,8,8a-hexahydropyrido[4,3-b][1,4]oxazin-3-one, and (4aR,8aS)-6-[3-[4-[1-(2,2-Dimethylpropyl)pyrazol-3-yl]phenyl]azetidine-1-carbonyl]-4,4a,5,7,8,8a-hexahydropyrido[4,3-b][1,4]oxazin-3-one

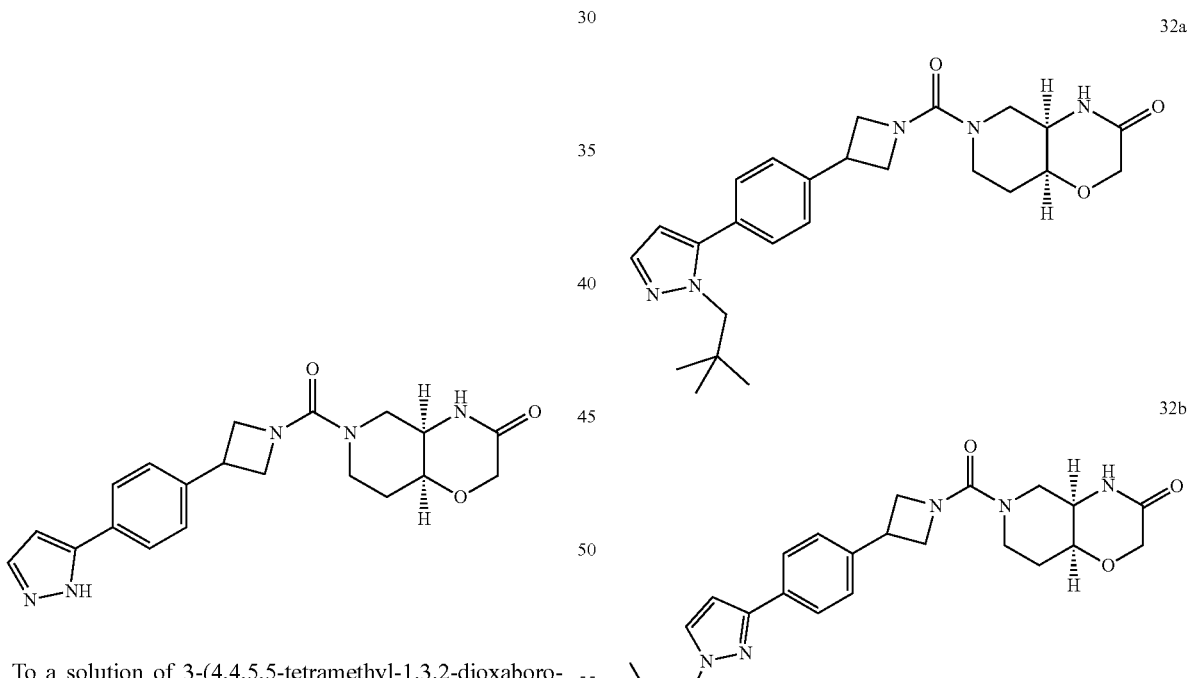

To a solution of 3-(4,4,5,5-tetramethyl-1,3,2-dioxaborolan-2-yl)-1H-pyrazole (147.7 mg, 0.760 mmol; CAS RN 269410-08-4), (4aR,8aS)-6-[3-(4-bromophenyl)azetidine-1-carbonyl]-4,4a,5,7,8,8a-hexahydropyrido[4,3-b][1,4]oxazin-3-one (BB4 step c, 200.0 mg, 0.510 mmol) and K₂CO₃ (140.22 mg, 1.01 mmol) in 1,4-dioxane (10 mL) and water (2 mL) was added Pd(dppf)Cl₂ (66.12 mg, 0.100 mmol, CAS RN 12150-46-8) and the mixture was stirred at 90° C. for 12 h. The mixture was filtered and the filtrate evaporated. The residue was purified by prep-HPLC (0.225% v/v FA in water and ACN) to give the desired product (6.5 mg, 0.020 mmol, 3.3%) as an off-white solid. MS (ESI): m/z=382.4 [M+H]+.

The solution of (4aR,8aS)-6-[3-[4-(1H-pyrazol-5-yl)phenyl]azetidine-1-carbonyl]-4,4a,5,7,8,8a-hexahydropyrido[4,3-b][1,4]oxazin-3-one (example 31, 140.0 mg, 0.370 mmol), 1-bromo-2,2-dimethylpropane (110.88 mg, 0.730 mmol) and Cs₂CO₃ (239.18 mg, 0.730 mmol) in DMF (2.6 mL) was stirred at 80° C. for 12 h. The mixture was diluted with water and extracted three times with EtOAc (10 mL each). The combined organic layers were dried over Na₂SO₄, filtered and evaporated. The residue was purified and the regioisomers separated by prep-HPLC (0.225% v/v FA in water and ACN) to give the ex. HR1 (2.5 mg, 0.010 mmol, 2.6%) and ex. HR2 (31.4 mg, 0.070 mmol, 32.5%) each as a light yellow solid. MS (ESI): m/z=452.3 [M+H]+ for both regiosisomers.

Example 33

(4aR,8aS)-6-[3-[4-(3-Chloro-2-pyridyl)phenyl]azetidine-1-carbonyl]-4,4a,5,7,8,8a-hexahydropyrido[4,3-b][1,4]oxazin-3-one

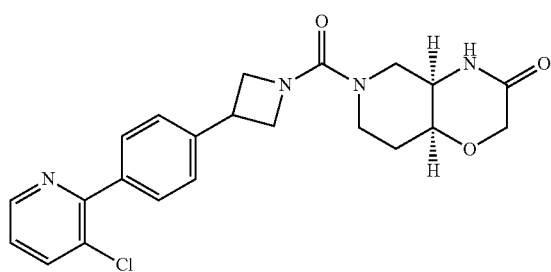 [SMILES: O=C1CO[C@H]2CCN(C(=O)N3CC(c4ccc(-c5ncccc5Cl)cc4)C3)C[C@H]2N1]

To a solution of tributyl-(3-chloro-2-pyridyl)stannane (122.5 mg, 0.300 mmol, CAS RN 206357-78-0) and (4aR,8aS)-6-[3-(4-bromophenyl)azetidine-1-carbonyl]-4,4a,5,7,8,8a-hexahydropyrido[4,3-b][1,4]oxazin-3-one (BB4 step c, 100.0 mg, 0.250 mmol) in DMF (5 mL) was added Pd(PPh3)4 (58.64 mg, 0.050 mmol) and the mixture was stirred at 100° C. under N2 atmosphere for 12 h. The mixture was poured into water (20 mL) and extracted three times with EtOAc (5 mL each). The combined organic layers were washed with brine and dried over Na2SO4, filtered and the filtrate evaporated. The residue was purified by reverse flash column chromatography (0.1% v/v FA in water and ACN) followed by prep-HPLC (0.225% v/v FA in water and ACN) to yield the desired compound as a white solid (2.8 mg, 99.4% purity, 2.6%). MS (ESI): m/z=427.2 [M+H]+.

Step a) Tributyl-(3-chloro-2-pyridyl)stannane

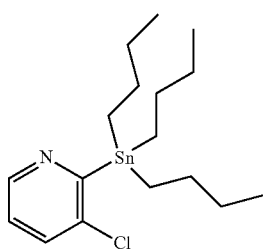 [SMILES: CCC[CH2][Sn]([CH2]CCC)([CH2]CCC)[c]1ncccc1Cl]

To a solution of 2-bromo-3-chloropyridine (576.0 mg, 2.99 mmol, CAS RN 96424-68-9) in toluene (20 mL) under N2 was added n-BuLi in hexane (2.5M, 1.32 mL, 3.29 mmol) dropwise at −78° C. The reaction mixture was stirred at −78° C. for 2 h, followed by the addition of tributyltin chloride (1071.73 mg, 3.29 mmol). The reaction mixture was stirred for another 2 h at −78° C., then warmed to RT and stirred for another 12 h. The reaction was quenched with saturated aq. NH4Cl solution (50 mL). The mixture was extracted three times with EtOAc (30 mL each), and the combined organic layers were washed with brine, dried over Na2SO4, and filtered. The filtrate was concentrated in vacuo to afford the desired product (1100 mg, 2.73 mmol, 91.3%) as light yellow oil which was used in the next step without further purification. MS (ESI): m/z=404.1 [M+H]+.

Example 34

(4aR,8aS)-6-[3-[4-(2,4-Dimethyloxazol-5-yl)phenyl]azetidine-1-carbonyl]-4,4a,5,7,8,8a-hexahydropyrido[4,3-b][1,4]oxazin-3-one

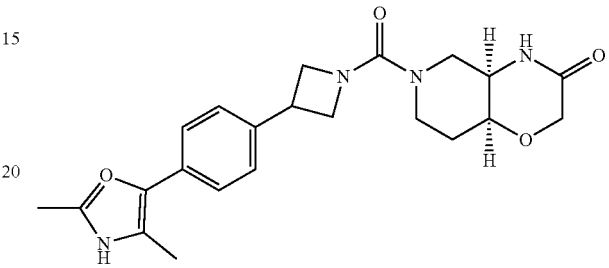

To a solution of (4aR,8aS)-6-[3-[4-(4,4,5,5-tetramethyl-1,3,2-dioxaborolan-2-yl)phenyl]azetidine-1-carbonyl]-4,4a,5,7,8,8a-hexahydropyrido[4,3-b][1,4]oxazin-3-one (BB4 step d, 80.0 mg, 0.180 mmol), Na2CO3 (38.42 mg, 0.360 mmol) and 5-bromo-2,4-dimethyl-oxazole (31.91 mg, 0.180 mmol, CAS RN 187399-73-1) in 1,4-dioxane (4 mL) and water (1 mL) was added [1,1'-bis(diphenylphosphino)ferrocene]dichloropalladium(II) (13.3 mg, 0.020 mmol) and the mixture was stirred at 100° C. under nitrogen atmosphere for 12 h. The mixture was poured into water (20 mL) and extracted three times with EtOAc (10 mL each). The combined organic layers were washed with brine and dried over Na2SO4, filtered and the filtrate concentrated. The residue was purified by prep-HPLC (0.5% ammonia in water and ACN) to furnish the desired compound as a pink solid (23.7 mg, 0.060 mmol, 30.6%). MS (ESI): m/z=411.2 [M+H]+.

Example 35

(4aR,8aS)-6-[3-[4-(3,5-Dimethylpyrazol-1-yl)phenyl]azetidine-1-carbonyl]-4,4a,5,7,8,8a-hexahydropyrido[4,3-b][1,4]oxazin-3-one

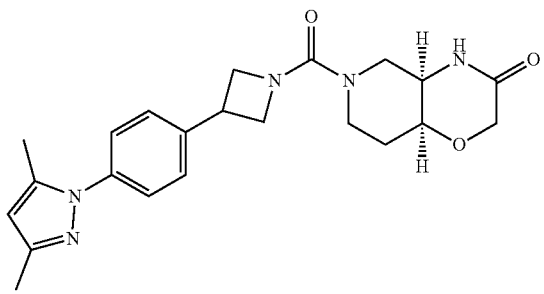 [SMILES: Cc1cc(C)n(-c2ccc(C3CN(C(=O)N4CC[C@@H]5OCC(=O)N[C@@H]5C4)C3)cc2)n1]

To a solution of 1-[4-(azetidin-3-yl)phenyl]-3,5-dimethylpyrazole (trifluoroacetic acid salt) (150.0 mg, 0.440 mmol) in ACN (5 mL) was added DIPEA (340.14 mg, 2.64 mmol) followed by (4-nitrophenyl) (4aR,8aS)-3-oxo-4,4a,5,7,8,8a-hexahydropyrido[4,3-b][1,4]oxazine-6-carboxylate (169.43 mg, 0.530 mmol, BB2a) and the reaction mixture was stirred at 80° C. for 12 h. The solution was concentrated, and the residue was purified by prep-HPLC (0.225% v/v TFA in water and ACN) to give the desired product as a light yellow solid (53.9 mg, 0.130 mmol, 27.7%, purity 92.4%). MS (ESI): m/z=410.0 [M+H]+.

Step a) 1-(4-Bromophenyl)-3,5-dimethyl-pyrazole

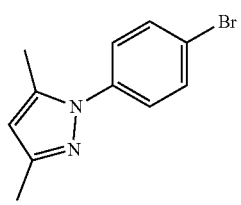

A solution of (4-bromophenyl)hydrazine (500.0 mg, 2.67 mmol, CAS RN 41931-18-4) and acetylacetone (294.41 mg, 2.94 mmol, CAS RN 123-54-6), copper(II) nitrate trihydrate (128.31 mg, 0.530 mmol, CAS RN 10031-43-3) in ACN (12 mL) was stirred at 20° C. for 2 h. The mixture was diluted with EtOAc (20 mL) and washed with water and then brine, the organic phase was dried over Na$_2$SO$_4$ and concentrated. The residue was purified by silica gel column chromatography (PE:EtOAc=20:1) to give the desired product as a light yellow oil (400 mg, 1.59 mmol, 71.2%). MS (ESI): m/z=251.0 [M+H]+.

Step b) tert-Butyl 3-[4-(3,5-dimethylpyrazol-1-yl)phenyl]azetidine-1-carboxylate

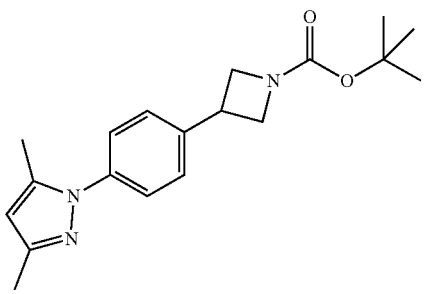 [SMILES: Cc1cc(C)n(-c2ccc(C3CN(C(=O)OC(C)(C)C)C3)cc2)n1]

To a 40 mL vial equipped with a stirring bar was added tert-butyl 3-bromoazetidine-1-carboxylate (329.08 mg, 1.39 mmol, CAS RN 1064194-10-0), 1-(4-bromophenyl)-3,5-dimethyl-pyrazole (350.0 mg, 1.39 mmol, CAS RN 62546-27-4), Ir[dF(CF$_3$)ppy]$_2$(dtbbpy)PF$_6$ (7.81 mg, 0.010 mmol), NiCl$_2$·glyme (1.84 mg, 0.010 mmol), 4-tert-butyl-2-(4-tert-butyl-2-pyridyl)pyridine (2.24 mg, 0.010 mmol), bis(trimethylsilyl)silyl-trimethyl-silane (346.57 mg, 1.39 mmol), Na$_2$CO$_3$ (295.45 mg, 2.79 mmol) and then DME (10 mL). The vial was sealed and placed under nitrogen. The reaction mixture was stirred and irradiated with a 34 W blue LED lamp (7 cm distance), with cooling fan to keep the reaction temperature at 25° C. for 14 h. The mixture was filtered and the filtrate was concentrated. The residue was purified by reversed flash column chromatography (0.1% v/v FA in water and ACN) to give the desired product as a yellow oil (300 mg, 0.920 mmol, 65.7%). MS (ESI): m/z=328.1 [M+H]+.

Step c) 1-[4-(Azetidin-3-yl)phenyl]-3,5-dimethyl-pyrazole, trifluoroacetic acid salt

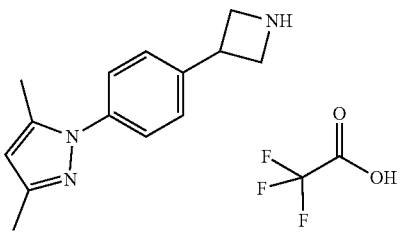 [SMILES: Cc1cc(C)n(-c2ccc(C3CNC3)cc2)n1 ; O=C(O)C(F)(F)F]

To a solution of tert-butyl 3-[4-(3,5-dimethylpyrazol-1-yl)phenyl]azetidine-1-carboxylate (150.0 mg, 0.460 mmol) in DCM (5 mL) was added TFA (1.0 mL). The mixture was stirred at 20° C. for 3 h and then concentrated to give the crude desired product (150 mg, 0.440 mmol, 95.9%) as a yellow oil. MS (ESI): m/z=228.1 [M+H]+.

Example 36

(4aR, 8aS)-6-[3-[4-[3-(2,2-Dimethylpropyl)triazol-4-yl]phenyl]azetidine-1-carbonyl]-4,4a,5,7,8,8a-hexahydropyrido[4,3-b][1,4]oxazin-3-one

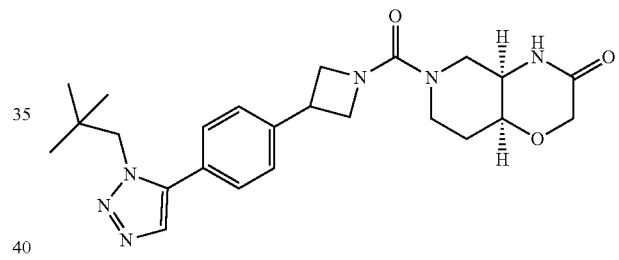

A mixture of (4-nitrophenyl) (4aR,8aS)-3-oxo-4,4a,5,7,8,8a-hexahydropyrido[4,3-b][1,4]oxazine-6-carboxylate (66.2 mg, 0.210 mmol, BB2a), DIPEA (241.9 mg, 1.87 mmol) and 5-[4-(azetidin-3-yl)phenyl]-1-(2,2-dimethylpropyl)triazole trifluroacetic acid salt (72.0 mg, 0.190 mmol) in ACN (3 mL) was stirred at 80° C. for 12 h. The mixture was concentrated under reduced pressure and the residue was purified by prep-HPLC (0.025% FA in water and ACN) to give the desired compound as a light yellow solid (18 mg, 0.040 mmol, 20.5%). MS (ESI): m/z=453.0 [M+H]+.

Step a) 1-Azido-4-nitro-benzene

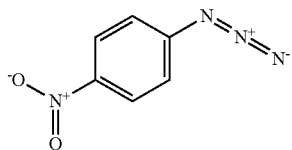

4-Nitroaniline (2000.0 mg, 14.48 mmol) was dissolved in ACN (20 mL), and the mixture was cooled to 0° C. in an ice-salt bath. To the stirred solution was added tert-butyl nitrite (1791.8 mg, 17.38 mmol) and the mixture was stirred for 10 min. Then azidotrimethylsilane (2.88 mL, 21.72 mmol) was added dropwise, and the resulting brown solution was stirred at 25° C. for 2 h. The reaction mixture was poured into water (100 mL) and extracted three times with EtOAc (100 mL each) and the organic layer was evaporated under reduced pressure. The residue was purified by silica gel column chromatography (100% PE) to give 1-azido-4-nitro-benzene (2100 mg, 12.64 mmol, 87.3) as yellow solid.

Step b)
5-(4-Bromophenyl)-1-(2,2-dimethylpropyl)triazole

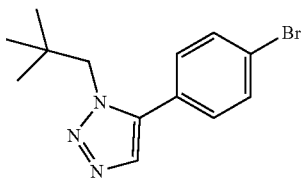 [SMILES: CC(C)(C)Cn1nncc1-c1ccc(Br)cc1]

To the solution of 4'-bromoacetophenone (1940.4 mg, 9.75 mmol), neopentylamine (1104.6 mg, 12.67 mmol), 1-azido-4-nitro-benzene (1600.0 mg, 9.75 mmol), AcOH (175.6 mg, 2.92 mmol) in toluene (64 mL) were added molecular sieves (4A, 500 mg) and the reaction was stirred at 100° C. for 16 h. The reaction mixture was filtered and the filtrate was evaporated under reduced pressure. The residue was by column chromatography (PE:EA=3:1) to give the desired compound as a yellow gum (997 mg, 3.39 mmol, 34.8%).

Step c) tert-Butyl 3-[4-[3-(2, 2-dimethylpropyl) triazol-4-yl] phenyl] azetidine-1-carboxylate

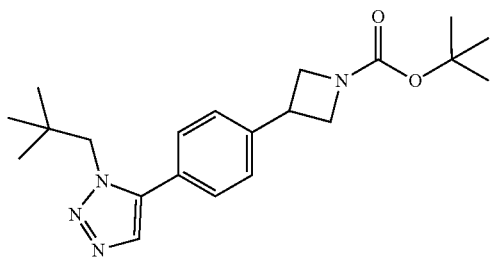 [SMILES: CC(C)(C)Cn1nncc1-c1ccc(C2CN(C(=O)OC(C)(C)C)C2)cc1]

The title compound was prepared in analogy to example 35, step b), from 5-(4-bromophenyl)-1-(2,2-dimethylpropyl) triazole and tert-butyl 3-bromoazetidine-1-carboxylate. Yellow gum (75.9%). MS (ESI): m/z=371.0 [M+H]$^+$.

Step d) 5-[4-(Azetidin-3-yl) phenyl]-1-(2, 2-dimethylpropyl)triazole trifluoroacetic acid salt

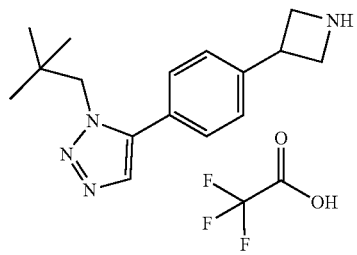

To a solution of tert-butyl 3-[4-[3-(2,2-dimethylpropyl) triazol-4-yl]phenyl]azetidine-1-carboxylate (70.0 mg, 0.190 mmol) in DCM (2 mL) was added TFA (0.5 mL). The mixture was stirred at 20° C. for 12 h and then evaporated under reduced pressure to give the crude desired compound as a yellow oil (72 mg, 0.190 mmol, 99.1%). MS (ESI): m/z=270.9 [M+H]$^+$.

Example 37

(4aR,8aS)-6-[3-[4-[5-(2,2-Dimethylpropyl)-1,2,4-oxadiazol-3-yl]phenyl]azetidine-1-carbonyl]-4,4a,5,7,8,8a-hexahydropyrido[4,3-b][1,4]oxazin-3-one

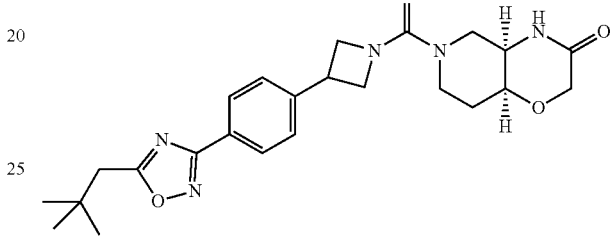

To a solution of 3-[4-(azetidin-3-yl)phenyl]-5-(2,2-dimethylpropyl)-1,2,4-oxadiazole, trifluoroacetic acid salt (150.0 mg, 0.390 mmol) in ACN (4 mL) was added DIPEA (301.3 mg, 2.34 mmol) and (4-nitrophenyl) (4aR,8aS)-3-oxo-4,4a,5,7,8,8a-hexahydropyrido[4,3-b][1,4]oxazine-6-carboxylate (150.07 mg, 0.470 mmol, BB2a) and the reaction was stirred at 80° C. for 12 h. The reaction mixture was evaporated and the residue was purified by prep-HPLC (0.225% v/v FA in water and ACN) to give the desired product as a light yellow solid (54.4 mg, 0.120 mmol, 30.4%). MS (ESI): m/z=454.4 [M+H]$^+$.

Step a) tert-Butyl 3-(4-Cyanophenyl)azetidine-1-carboxylate

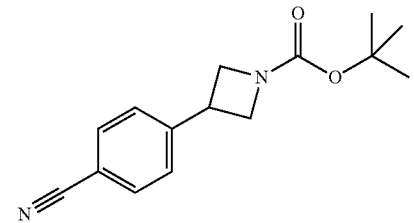 [SMILES: CC(C)(C)OC(=O)N1CC(c2ccc(C#N)cc2)C1]

The title compound was prepared in analogy to example 35, step b), from 4-bromobenzonitrile and tert-butyl 3-bromoazetidine-1-carboxylate. Light brown oil (1976 mg, 7.65 mmol, 69.6%). MS (ESI): m/z=203.6 [M-56+H]$^+$.

Step b) tert-Butyl 3-[4-(N-hydroxycarbamimidoyl)phenyl]azetidine-1-carboxylate

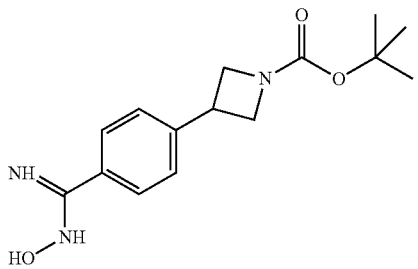 [SMILES: CC(C)(C)OC(=O)N1CC(c2ccc(C(=N)NO)cc2)C1]

A solution of hydroxylamine hydrochloride (349.7 mg, 5.03 mmol) in EtOH (8 mL) was added Na$_2$CO$_3$ (266.7 mg, 2.52 mmol) in water (2 mL) and the mixture was stirred at 20° C. for 25 min. Then tert-butyl 3-(4-cyanophenyl)azetidine-1-carboxylate (1000.0 mg, 3.87 mmol) was added and the mixture was stirred at 95° C. for 12 h. The mixture was diluted with water, concentrated under vacuum to remove the EtOH, the residue was partitioned between EtOAc (100 mL) and water (100 mL) and was extracted three times with water. The organic layer was washed with saturated NaCl solution (50 mL), dried over Na$_2$SO$_4$ and evaporated to give the desired product as a light yellow oil (773 mg, 2.65 mmol, 68.5%). MS (ESI): m/z=292.5 [M+H]$^+$.

Step c) tert-Butyl 3-[4-[5-(2,2-Dimethylpropyl)-1,2,4-oxadiazol-3-yl]phenyl]azetidine-1-carboxylate

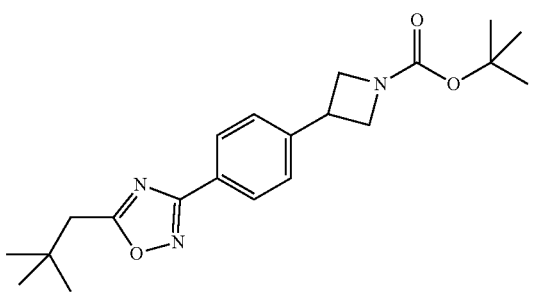 [SMILES: CC(C)(C)Cc1nc(-c2ccc(C3CN(C(=O)OC(C)(C)C)C3)cc2)no1]

To a solution of tert-butyl 3-[4-(N-hydroxycarbamimidoyl)phenyl]azetidine-1-carboxylate (770.0 mg, 2.64 mmol) and DIPEA (1.41 mL, 7.93 mmol) in toluene (6 mL) was added 3,3-dimethylbutyryl chloride (426.9 mg, 3.17 mmol) at 0° C., the mixture was stirred at 25° C. for 10 min. and then warmed up to 80° C. and stirred for 12 h. The mixture was evaporated and the residue was purified by silica gel column chromatography (PE:EA=10:1) to give the desired product (620 mg, 1.67 mmol, 63.2%) as a light brown oil. MS (ESI): m/z=316.5 [M-56+H]$^+$.

Step d) 3-[4-(Azetidin-3-yl)phenyl]-5-(2,2-dimethylpropyl)-1,2,4-oxadiazole (trifluoroacetic acid salt)

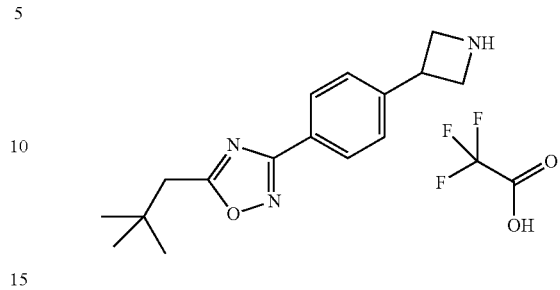

To a solution of tert-butyl 3-[4-[5-(2,2-dimethylpropyl)-1,2,4-oxadiazol-3-yl]phenyl]azetidine-1-carboxylate (300.0 mg, 0.810 mmol) in DCM (3 mL) was added TFA (0.6 mL, 7.79 mmol) and the mixture was stirred at 20° C. for 12 h. The mixture was evaporated to yield the crude desired product as a light yellow oil (300 mg, 0.780 mmol, 96.4%). MS (ESI): m/z=272.6 [M+H]$^+$.

Example 38

(4aR,8aS)-6-[3-[4-[5-(2,2-Dimethylpropyl)-1,3,4-oxadiazol-2-yl]phenyl]azetidine-1-carbonyl]-4,4a,5,7,8,8a-hexahydropyrido[4,3-b][1,4]oxazin-3-one

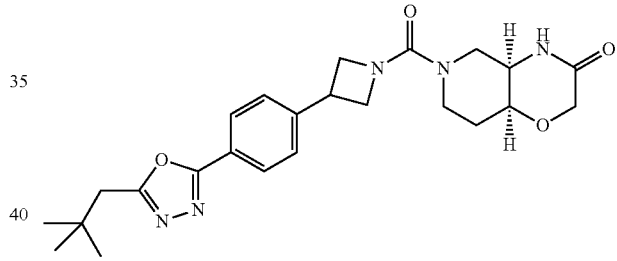

To a solution of 2-[4-(azetidin-3-yl)phenyl]-5-(2,2-dimethylpropyl)-1,3,4-oxadiazole trifluoroacetic acid salt (100.0 mg, 0.260 mmol) in ACN (2.5 mL) was added DIPEA (200.8 mg, 1.56 mmol) and (4-nitrophenyl) (4aR,8aS)-3-oxo-4,4a,5,7,8,8a-hexahydropyrido[4,3-b][1,4]oxazine-6-carboxylate (100.04 mg, 0.310 mmol, BB2a) and the reaction was stirred at 80° C. for 12 h. The reaction mixture was evaporated and the residue was purified by prep-HPLC (0.225% v/v FA in water and ACN) to give the desired product (48.3 mg, 0.110 mmol, 40.6%) as a light yellow solid. MS (ESI): m/z=454.3 [M+H]$^+$.

Step a) 4-Bromo-N'-(3,3-dimethylbutanoyl)benzoic hydrazide

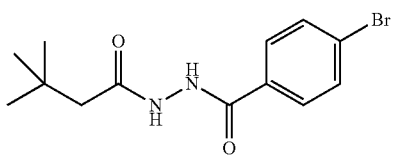 [SMILES: CC(C)(C)CC(=O)NNC(=O)c1ccc(Br)cc1]

To a solution of 4-bromobenzoic hydrazide (5.0 g, 23.25 mmol, CAS RN 5933-32-4) and DIPEA (12.4 mL, 69.75 mmol, CAS RN 7087-68-5) in DCM (50 mL) was added 3,3-dimethylbutyryl chloride (3.76 g, 27.9 mmol, CAS RN 122-94-1) at 0° C. and the mixture was allowed to warm to 20° C. After stirring for 12 h the mixture was diluted by water, extracted three times with EtOAc (200 mL each) and the combined organic layers were washed three times with water (100 mL each). The combined organic layers were dried over Na$_2$SO$_4$, filtered and evaporated to give the desired product as a light yellow solid (7 g, 22.4 mmol, 96.1%). MS (ESI): m/z=315.4 [M+H]$^+$.

Step b) 2-(4-Bromophenyl)-5-(2,2-dimethylpropyl)-1,3,4-oxadiazole

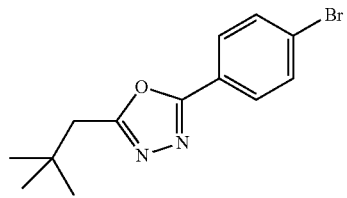 [SMILES: CC(C)(C)Cc1nnc(-c2ccc(Br)cc2)o1]

To a solution of 4-bromo-N'-(3,3-dimethylbutanoyl)benzoic hydrazide (5000.0 mg, 16.0 mmol) in toluene (102 mL) was added TsOH (5498.3 mg, 31.9 mmol) and the mixture was stirred at 110° C. for 12 h. The mixture was concentrated and the residue was purified by silica gel chromatography eluting with PE:EtOAc (10:1) to give the desired product as a light yellow solid (1000 mg, 3.4 mmol, 21.2%). MS (ESI): m/z=295.4 [M+H]$^+$.

Step c) tert-Butyl 3-[4-[5-(2,2-dimethylpropyl)-1,3,4-oxadiazol-2-yl]phenyl]azetidine-1-carboxylate

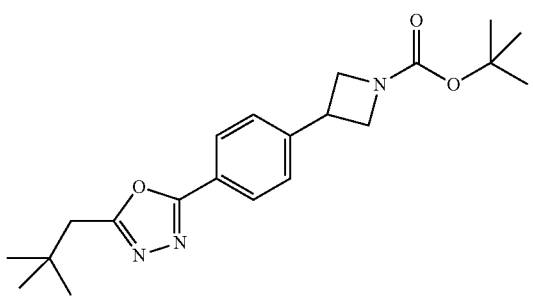 [SMILES: CC(C)(C)Cc1nnc(-c2ccc(C3CN(C(=O)OC(C)(C)C)C3)cc2)o1]

The title compound was prepared in analogy to example 35, step b), from 2-(4-Bromophenyl)-5-(2,2-dimethylpropyl)-1,3,4-oxadiazole and tert-butyl 3-bromoazetidine-1-carboxylate. Light brown oil. MS (ESI): m/z=372.5 [M+H]$^+$.

Step d) 2-[4-(Azetidin-3-yl)phenyl]-5-(2,2-dimethylpropyl)-1,3,4-oxadiazole (trifluoroacetic acid salt)

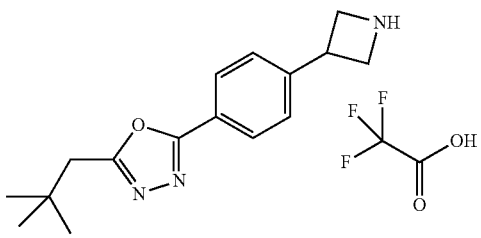

To a solution of tert-butyl 3-[4-[5-(2,2-dimethylpropyl)-1,3,4-oxadiazol-2-yl]phenyl]azetidine-1-carboxylate (200.0 mg, 0.540 mmol) in DCM (2 mL) was added TFA (0.4 mL) and the mixture was stirred at 20° C. for 12 h. The mixture was evaporated to give the crude desired product as a light brown oil (201 mg, 0.520 mmol, 96.9%). MS (ESI): m/z=272.6 [M+H]$^+$.

Example 39

(4aR,8aS)-6-[3-[4-[2-(2-Fluoroethyl)pyrazol-3-yl]phenyl]azetidine-1-carbonyl]-4,4a,5,7,8,8a-hexahydropyrido[4,3-b][1,4]oxazin-3-one

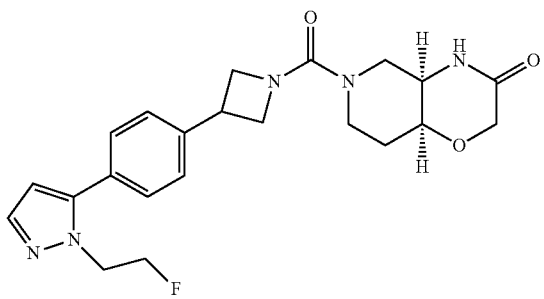 [SMILES: O=C1CO[C@H]2CCN(C(=O)N3CC(c4ccc(-c5ccnn5CCF)cc4)C3)C[C@H]2N1]

To a solution of 5-[4-(azetidin-3-yl)phenyl]-1-(2-fluoroethyl)pyrazole (110 mg, 0.380 mmol) and (4-nitrophenyl) (4aR,8aS)-3-oxo-4,4a,5,7,8,8a-hexahydropyrido[4,3-b][1,4]oxazine-6-carboxylate (124 mg, 0.390 mmol, BB2a) in MeCN (6 mL) was added N,N-diisopropylethylamine (0.2 mL, 1.15 mmol) with stirring at 60° C. The solution was stirred at 60° C. for 16 h. The solution was concentrated under vacuum to give a residue, which was purified by HPLC (TFA conditions) to give (4aR,8aS)-6-[3-[4-[2-(2-fluoroethyl)pyrazol-3-yl]phenyl]azetidine-1-carbonyl]-4,4a,5,7,8,8a-hexahydropyrido[4,3-b][1,4]oxazin-3-one (80 mg, 45%) as white solid. MS (ESI): m/z=428.4 [M+H]$^+$.

Step a) 5-(4-Bromophenyl)-1-(2-fluoroethyl)pyrazole

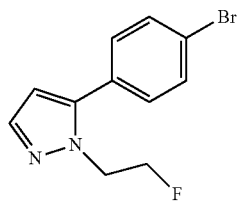 [SMILES: FCCn1nccc1-c1ccc(Br)cc1]

To a stirred solution at 20° C. of 2-fluoroethylhydrazine (330 mg, 4.23 mmol, CAS RN 126889-84-7) in DMF (20 mL) was added (E)-1-(4-bromophenyl)-3-(dimethylamino) prop-2-en-1-one (752 mg, 2.96 mmol, CAS RN 849619-11-0). The resulting mixture was stirred at 25° C. for 1 h and then at 70° C. for 5 h. The solution was concentrated under vacuum to give a residue, which was purified by flash column chromatography (petroleum ether:EtOAc 3:1) to give 5-(4-bromophenyl)-1-(2-fluoroethyl)pyrazole (450 mg, 39%) as white solid. MS (ESI): m/z=269.0/271.0 [M+H]$^+$.

Step b) tert-Butyl 3-[4-[2-(2-fluoroethyl)pyrazol-3-yl]phenyl]azetidine-1-carboxylate

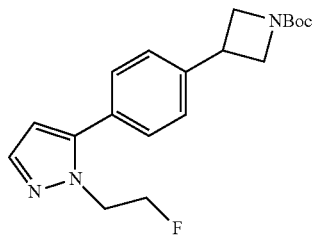 [SMILES: CC(C)(C)OC(=O)N1CC(c2ccc(-c3ccnn3CCF)cc2)C1]

tert-Butyl 3-bromoazetidine-1-carboxylate (395 mg, 1.67 mmol, CAS RN 1064194-10-0), 5-(4-bromophenyl)-1-(2-fluoroethyl)pyrazole (450 mg, 1.67 mmol), [Ir{dF(CF$_3$)ppy}$_2$(dtbpy)]PF$_6$ (19 mg, 0.020 mmol, CAS RN 870987-63-6), dichloronickel 1,2-dimethoxyethane (2.0 mg, 0.010 mmol), 4-tert-butyl-2-(4-tert-butyl-2-pyridyl)pyridine (3.0 mg, 0.010 mmol), bis(trimethylsilyl)silyltrimethyl-silane (416 mg, 1.67 mmol) and sodium carbonate (355 mg, 3.35 mmol) were mixed in DME (15 mL). The reaction mixture was stirred and irradiated with a 34 W blue LED lamp (7 cm away), with cooling fan to keep the reaction temperature at 25° C. for 14 h. The solution was poured into brine (30 mL) and extracted with EtOAc (20 mL). The organic layer was concentrated under vacuum to give a residue, which was purified by Prep-TLC (petroleum ether:EtOAc 1:1) to give tert-butyl 3-[4-[2-(2-fluoroethyl)pyrazol-3-yl]phenyl]azetidine-1-carboxylate (450 mg, 69%) as light yellow oil MS (ESI): m/z=346.1 [M+H]$^+$.

Step c) 5-[4-(Azetidin-3-yl)phenyl]-1-(2-fluoroethyl)pyrazole

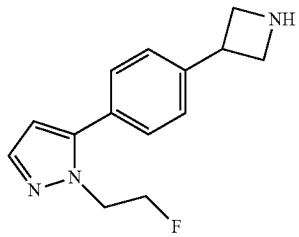 [SMILES: FCCn1nccc1-c1ccc(C2CNC2)cc1]

A solution of tert-butyl 3-[4-[2-(2-fluoroethyl)pyrazol-3-yl]phenyl]azetidine-1-carboxylate (160 mg, 0.410 mmol) in HCl in MeOH (4.0 mL, 16 mmol) was stirred at 25° C. for 4 h. The solution was concentrated under vacuum to give 5-[4-(azetidin-3-yl)phenyl]-1-(2-fluoroethyl)pyrazole (110 mg, 92%) as light yellow oil, which was used with no further purification in the next step. MS (ESI): m/z=246.1 [M+H]$^+$.

Example 40

(4aR,8aS)-6-[3-[4-[1-(2-Fluoroethyl)pyrazol-4-yl]phenyl]azetidine-1-carbonyl]-4,4a,5,7,8,8a-hexahydropyrido[4,3-b][1,4]oxazin-3-one

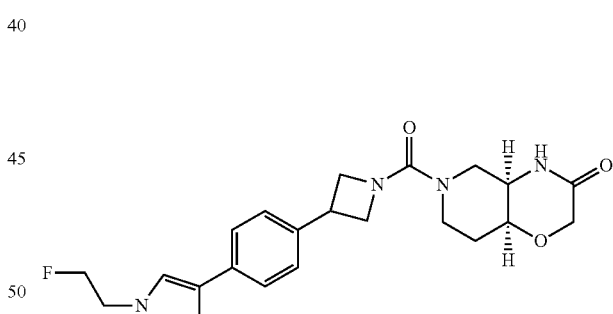

A mixture of 1-(2-fluoroethyl)-4-(4,4,5,5-tetramethyl-1,3,2-dioxaborolan-2-yl)pyrazole (58 mg, 0.24 mmol, CAS RN 1049730-39-3), (4aR,8aS)-6-(3-(4-bromophenyl)azetidine-1-carbonyl)hexahydro-2H-pyrido[4,3-b][1,4]oxazin-3(4H)-one (BB4 step c, 80 mg, 0.20 mmol), K$_2$CO$_3$ (2.0 mg, 0.02 mmol), Cs$_2$CO$_3$ (198 mg, 0.610 mmol) and [1,1'-bis(diphenylphosphino)ferrocene]dichloropalladium(II) (15 mg, 0.02 mmol) in DMSO (4 mL) and H$_2$O (0.5 mL) was stirred under nitrogen atmosphere at 80° C. for 16 h. The mixture was filtered and then purified by prep-HPLC (basic condition) to give the title compound as a grey solid (41 mg, 44%). LC-MS: 428.2 [M+H]$^+$.

Example 41

(4aR,8aS)-6-[3-[4-(4-Methyl-1,3-thiazol-2-yl)phenyl]azetidine-1-carbonyl]-4,4a,5,7,8,8a-hexahydropyrido[4,3-b][1,4]oxazin-3-one

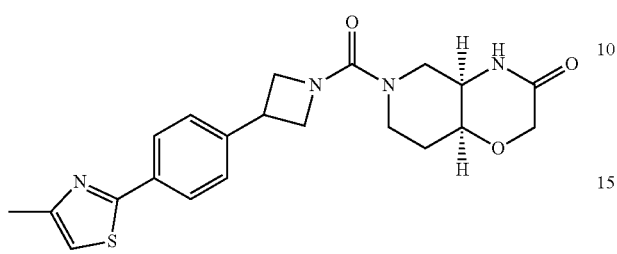

The title compound was prepared in analogy to example 31, intermediate, from 4-nitrophenyl (4aR,8aS)-3-oxohexahydro-2H-pyrido[4,3-b][1,4]oxazine-6(5H)-carboxylate and 2-(4-(azetidin-3-yl)phenyl)-4-methylthiazole 4-methylbenzenesulfonate. Colorless foam (37%). MS (ESI): m/z=413.3 [M+H]$^+$.

Step a) tert-Butyl 3-(4-(4-methylthiazol-2-yl)phenyl)azetidine-1-carboxylate

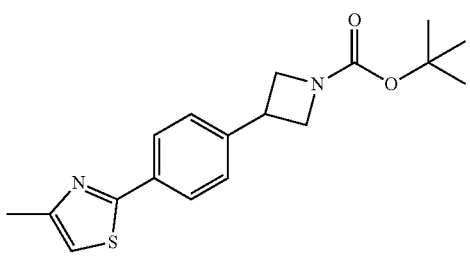 [SMILES: Cc1csc(-c2ccc(C3CN(C(=O)OC(C)(C)C)C3)cc2)n1]

The title compound was prepared in analogy to BB4, step a), from 4-methyl-2-(4-(4,4,5,5-tetramethyl-1,3,2-dioxaborolan-2-yl)phenyl)thiazole (Maybridge) and tert-butyl 3-iodoazetidine-1-carboxylate (CAS RN 254454-54-1). Colorless oil which was used in the next step without further purification. MS (ESI): m/z=331.2 [M+H]$^+$.

Step b) 2-[4-(Azetidin-3-yl)phenyl]-4-methyl-thiazole; 4-methylbenzenesulfonic acid

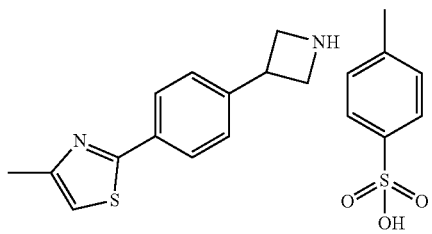

A suspension of tert-butyl 3-(4-(4-methylthiazol-2-yl)phenyl)azetidine-1-carboxylate (28 mg, 84.7 µmol) and 4-methylbenzenesulfonic acid hydrate (19.3 mg, 102 µmol) in EtOAc (0.3 mL) were stirred at reflux for 2 h. The mixture was completely evaporated to provide the desired compound which was used in the next step without further purification. MS (ESI): m/z=231.1 [M+H]$^+$.

Example 42

(4aR,8aS)-6-[3-[4-(1-Methylpyrazol-3-yl)phenyl]azetidine-1-carbonyl]-4,4a,5,7,8,8a-hexahydropyrido[4,3-b][1,4]oxazin-3-one

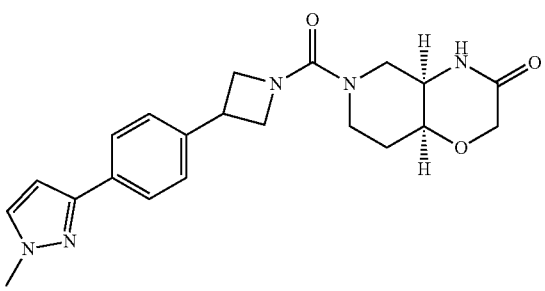 [SMILES: Cn1ccc(-c2ccc(C3CN(C(=O)N4CC[C@@H]5OCC(=O)N[C@@H]5C4)C3)cc2)n1]

(4aR,8aS)-6-(3-(4-Bromophenyl)azetidine-1-carbonyl)hexahydro-2H-pyrido[4,3-b][1,4]oxazin-3(4H)-one (16 mg, 40.6 µmol, BB4, step c) and (1-methyl-1H-pyrazol-3-yl)boronic acid (5.11 mg, 40.6 µmol, CAS RN 869973-96-6), and tetrakis(triphenylphosphine)palladium(0) (2.34 mg, 2.03 µmol) were dissolved in THF (600 µL) and water (60 µl) and the reaction stirred at 80° C. over night. The reaction mixture was extracted with EtOAc and H$_2$O, the organic layer dried over Na$_2$SO and evaporated. The crude product was purified by a prep-HPLC to give the compound as a white solid. MS (ESI): m/z=396.2 [M+H]$^+$.

Example 43

(4aR,8aS)-6-[3-[4-(6-Fluoropyridin-3-yl)phenyl]azetidine-1-carbonyl]-4,4a,5,7,8,8a-hexahydropyrido[4,3-b][1,4]oxazin-3-one

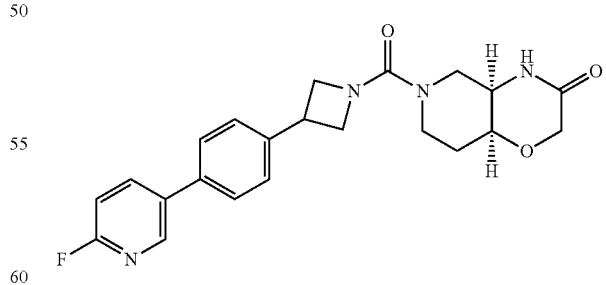

The title compound was prepared in analogy to example 42, from (4aR,8aS)-6-(3-(4-bromophenyl)azetidine-1-carbonyl)hexahydro-2H-pyrido[4,3-b][1,4]oxazin-3(4H)-one (BB4, step c) and 2-fluoropyridine-5-boronic acid (CAS RN: 351019-18-6). White solid. MS (ESI): m/z=411.2 [M+H]$^+$.

Example 44

(4aR,8aS)-6-[3-[4-(2-Fluoropyridin-4-yl)phenyl] azetidine-1-carbonyl]-4,4a,5,7,8,8a-hexahydropyrido [4,3-b][1,4]oxazin-3-one

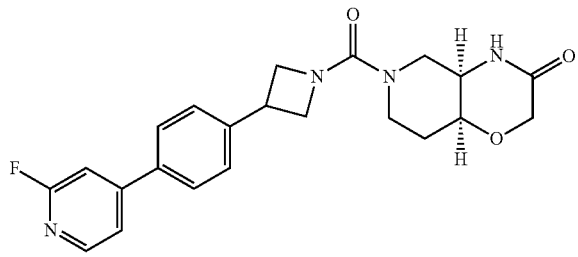 [SMILES: O=C1CO[C@H]2CCN(C(=O)N3CC(c4ccc(-c5ccnc(F)c5)cc4)C3)C[C@H]2N1]

The title compound was prepared in analogy to example 42, from (4aR,8aS)-6-(3-(4-bromophenyl)azetidine-1-carbonyl)hexahydro-2H-pyrido[4,3-b][1,4]oxazin-3(4H)-one (BB4, step c) and (2-fluoropyridin-4-yl)boronic acid (CAS RN: 401815-98-3). Yellow powder (84%). MS (ESI): m/z=411.2 [M+H]⁺.

Example 45

(4aR,8aS)-6-[3-[4-(1-Methylpyrazol-4-yl)phenyl] azetidine-1-carbonyl]-4,4a,5,7,8,8a-hexahydropyrido [4,3-b][1,4]oxazin-3-one

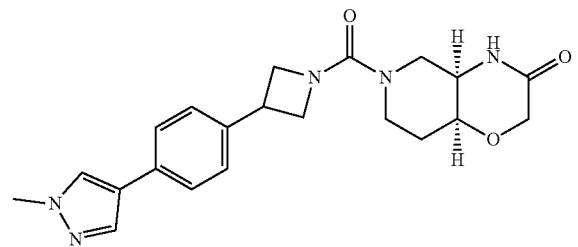 [SMILES: Cn1cc(-c2ccc(C3CN(C(=O)N4CC[C@@H]5OCC(=O)N[C@@H]5C4)C3)cc2)cn1]

The title compound was prepared in analogy to example 42, from (4aR,8aS)-6-(3-(4-bromophenyl)azetidine-1-carbonyl)hexahydro-2H-pyrido[4,3-b][1,4]oxazin-3(4H)-one (BB4, step c) and 1-methyl-1H-pyrazole-4-boronic acid (CAS RN: 763120-58-7). Light yellow powder (57%). MS (ESI): m/z=396.2 [M+H]⁺.

Example 46

(4aR,8aS)-6-[3-[4-(2-Methylpyrazol-3-yl)phenyl] azetidine-1-carbonyl]-4,4a,5,7,8,8a-hexahydropyrido [4,3-b][1,4]oxazin-3-one

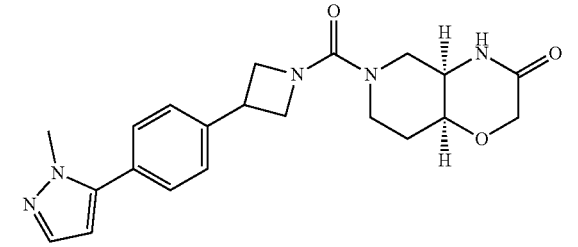 [SMILES: Cn1nccc1-c1ccc(C2CN(C(=O)N3CC[C@@H]4OCC(=O)N[C@@H]4C3)C2)cc1]

The title compound was prepared in analogy to example 31, intermediate, from 4-nitrophenyl (4aR,8aS)-3-oxohexahydro-2H-pyrido[4,3-b][1,4]oxazine-6(5H)-carboxylate and 5-(4-(azetidin-3-yl)phenyl)-1-methyl-1H-pyrazole 4-methylbenzenesulfonate. Colorless solid (25%). MS (ESI): m/z=396.2 [M+H]⁺.

Step a) tert-Butyl 3-[4-(2-methylpyrazol-3-yl)phenyl]azetidine-1-carboxylate

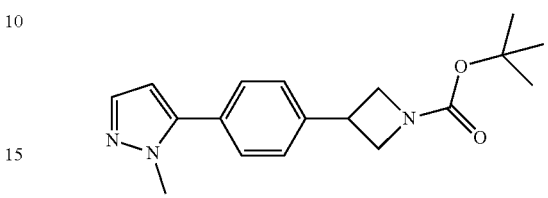

The title compound was prepared in analogy to example BB4, step a, from tert-butyl 3-iodoazetidine-1-carboxylate (CAS RN 254454-54-1) and (4-(1-methyl-H-pyrazol-5-yl)phenyl)boronic acid (ChemBridge Corp.). Colorless oil which was used in the next step without further purification. MS (ESI): m/z=314.3 [M+H]⁺.

Step b) 5-[4-(Azetidin-3-yl)phenyl]-1-methyl-pyrazole; 4-methylbenzenesulfonic acid The title compound was prepared in analogy to example 41, step b, from tert-butyl 3-[4-(2-methylpyrazol-3-yl)phenyl]azetidine-1-carboxylate. Light brown gum. MS (ESI): m/z=214.1 [M+H]⁺.

Example 47

(4aR,8aS)-6-[3-[5-(4-Fluorophenoxy)-2-pyridyl] azetidine-1-carbonyl]-4,4a,5,7,8,8a-hexahydropyrido [4,3-b][1,4]oxazin-3-one

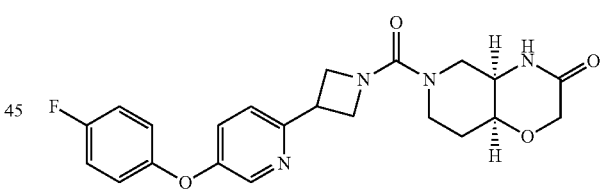

To a solution of 2-(azetidin-3-yl)-5-(4-fluorophenoxy) pyridine (50 mg, 0.17 mmol) and DIPEA (0.17 mL, 1.04 mmol) in ACN (2 mL) was added (4-nitrophenyl) (4aR, 8aS)-3-oxo-4,4a,5,7,8,8a-hexahydropyrido[4,3-b][1,4] oxazine-6-carboxylate (67 mg, 0.21 mmol, BB2a) at 25° C. The mixture was stirred at 90° C. for 12 h, concentrated under reduced pressure, purified by preparative HPLC (0.225% TFA) and lyophilized to give the title compound (22.1 mg, 0.050 mmol, 28.5% yield) as light yellow solid. MS (ESI): m/z=427.2 [M+H]⁺.

Step a) tert-Butyl 3-[5-(4-fluorophenoxy)-2-pyridyl]-3-hydroxy-azetidine-1-carboxylate 2-Bromo-5-(4-fluorophenoxy)pyridine (350 mg, 1.31 mmol, CAS RN 1643917-85-4_) was dissolved in toluene (15 mL) and cooled to −78° C. nBuLi in hexanes (0.57 mL, 1.44 mmol) was added dropwise and the mixture was stirred at −78° C. for 30 minutes under a N$_2$ atmosphere. 1-Boc-3-azetidinone (246 mg, 1.44 mmol, CAS RN 398489-26-4) in toluene (2 mL) was added. The reaction mixture was stirred at 0° C. for 4 h, quenched with saturated NH$_4$Cl (20 mL) and extracted with EtOAc (2×15 mL). The combined extracts were washed with brine (20 mL), dried over Na$_2$SO$_4$, concentrated in vacuo and purified by reverse phase flash chromatography to give the title compound (171 mg, 0.470 mmol, 36.3% yield) as white solid. MS (ESI): m/z=361.2 [M+H]$^+$.

Step b) tert-Butyl 3-chloro-3-[5-(4-fluorophenoxy)-2-pyridyl]azetidine-1-carboxylate To a solution of tert-butyl 3-[5-(4-fluorophenoxy)-2-pyridyl]-3-hydroxy-azetidine-1-carboxylate (500 mg, 1.39 mmol) in DCM (15 mL) was added thionyl chloride (990 mg, 8.32 mmol) at 0° C. The mixture was stirred at 20° C. for 12 h, poured into sat. Na$_2$CO$_3$ (15 mL) and extracted with DCM (3×10 mL). The combined organic layers were washed with brine (20 mL), dried over Na$_2$SO$_4$, concentrated in vacuo and purified by reverse phase flash chromatography (0.05% TFA) to give the title compound (230 mg, 0.610 mmol, 43.8% yield) as light yellow oil. MS (ESI): m/z=322.8 [M-C$_4$H$_8$+H]$^+$.

Step c) 2-(Azetidin-3-yl)-5-(4-fluorophenoxy)pyridine

To a solution of tert-butyl 3-chloro-3-[5-(4-fluorophenoxy)-2-pyridyl]azetidine-1-carboxylate (200 mg, 0.530 mmol) and formic acid (121 mg, 2.64 mmol) in methanol (12 mL) was added wet Pd/C (100 mg, 0.530 mmol). The mixture was stirred at 50° C. for 12 h and filtered. The filtrate was concentrated in vacuum to give a yellow residue, which was purified by reverse phase flash chromatography (0.05% TFA) to give the title compound (50 mg, 0.200 mmol, 38.8% yield) as colorless oil and tert-butyl 3-[5-(4-fluorophenoxy)-2-pyridyl]azetidine-1-carboxylate (54 mg, 0.160 mmol, 29.7% yield) as light brown oil. MS (ESI): m/z=245.2 [M+H]$^+$.

Example 48

(4aR,8aS)-6-(3-(6-(4-Fluorophenoxy)pyridin-3-yl)azetidine-1-carbonyl)hexahydro-2H-pyrido[4,3-b][1,4]oxazin-3(4H)-one

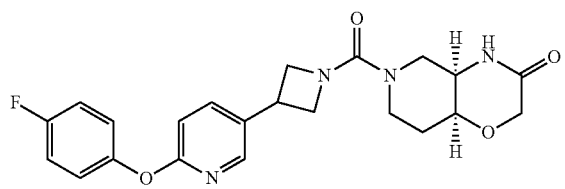 [SMILES: O=C1CO[C@H]2CCN(C(=O)N3CC(c4ccc(Oc5ccc(F)cc5)cn4)C3)C[C@H]2N1]

A solution of (4aR,8aS)-hexahydro-2H-pyrido[4,3-b][1,4]oxazin-3(4H)-one (2S,3S)-2,3-bis((4-methylbenzoyl)oxy)succinate (54.3 mg, 100 µmol) and di(1H-1,2,4-triazol-1-yl)methanone (16 mg, 100 µmol) in ACN (2 mL) and TEA (73 mg, 100 µL, 717 µmol) was shaken for 90 min at room temperature. 5-(Azetidin-3-yl)-2-(4-fluorophenoxy)pyridine 4-methylbenzenesulfonate (42 mg, 0.1 mmol) was added and the mixture was shaken for 30 min at room temperature and subsequently for 90 min at 60° C. The clear solution was filtered through a Hypersep Amino SPE Column (1 g, Part. No.: 60108-432). The column was washed with ACN (total 6 mL), the solvent was removed under reduced pressure and the residue purified by prep. HPLC to obtain the title compound (15 mg, 35.4 µmol, 35.4% yield) as colorless waxy solid. MS (ESI): m/z=427.2 [M+H]$^+$.

Step a) tert-Butyl 3-(6-phenoxypyridin-3-yl)azetidine-1-carboxylate

DME (6 mL) was added to a mixture of 5-bromo-2-(4-fluorophenoxy)pyridine (686 mg, 2.56 mmol, CAS RN 936343-65-6), tert-butyl 3-bromoazetidine-1-carboxylate (604 mg, 2.56 mmol, CAS RN 1064194-10-0), (Ir[dF(CF$_3$)ppy]$_2$(dtbpy))PF$_6$ (29 mg, 25.6 µmol, CAS RN 870987-63-6), tris(trimethylsilyl)silane (636 mg, 789 µL, 2.56 mmol) and anhydrous sodium carbonate (407 mg, 3.84 mmol). The mixture was stirred for 5 min with argon bubbling through the suspension. The reaction vessel was sealed. A separate vial was charged with Nickel(II) chloride ethylene glycol dimethyl ether complex (2.8 mg, 12.8 µmol, CAS RN 29046-78-4) and 4,4'-di-tert-butyl-2,2'-bipyridine (3.4 mg, 12.8 µmol). DME (616 µL) was added. The vial was sealed, purged with argon, sonicated for 5 min and then poured into the reaction vessel. The reaction mixture was stirred and irradiated with a 420 nm lamp under an argon atmosphere for 3 hours. The solid was filtered off, washed with ethyl acetate and the filtrate was evaporated. The crude was absorbed with isolute HM-N, dried and purified by flash chromatography to give the title compound (296 mg, 774 µmol, 30.2% yield) as light yellow waxy solid. MS (ESI): m/z=361.2 [M+H]$^+$.

Step b) 5-(Azetidin-3-yl)-2-(4-fluorophenoxy)pyridine 4-methylbenzenesulfonate

To a solution of tert-butyl 3-(6-phenoxypyridin-3-yl)azetidine-1-carboxylate (296 mg, 907 µmol) in ethyl acetate (7 mL) was added 4-methylbenzenesulfonic acid hydrate (77 mg, 407 µmol). The mixture was heated under reflux conditions for 18 h, cooled to room temperature, diluted with 3 mL diethyl ether, stirred for 1 h and filtered. The solid was washed with ether (3×1 mL) and dried under vacuum to obtain the title compound (285 mg, 684 µmol, 75.4% yield) as white crystals. MS (ESI): m/z=245.1 [M+H]$^+$.

Example 49

(4aR,8aS)-6-(3-(6-(4-(Trifluoromethoxy)phenoxy)pyridin-3-yl)azetidine-1-carbonyl)hexahydro-2H-pyrido[4,3-b][1,4]oxazin-3(4H)-one

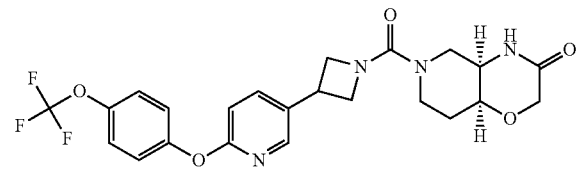 [SMILES: O=C1CO[C@H]2CCN(C(=O)N3CC(c4ccc(Oc5ccc(OC(F)(F)F)cc5)nc4)C3)C[C@H]2N1]

In analogy to the procedure described in example 48, (4aR,8aS)-hexahydro-2H-pyrido[4,3-b][1,4]oxazin-3(4H)-one (2S,3S)-2,3-bis((4-methylbenzoyl)oxy)succinate was reacted with 5-(azetidin-3-yl)-2-(4-(trifluoromethoxy)phenoxy)pyridine 4-methylbenzenesulfonate to obtain the title compound as white foam. MS (ESI): m/z=493.2 [M+H]⁺.

Step a) tert-Butyl 3-(6-(4-(trifluoromethoxy)phenoxy)pyridin-3-yl)azetidine-1-carboxylate In analogy to the procedure described in example 48 a, 5-bromo-2-(4-(trifluoromethoxy)phenoxy)pyridine (CAS RN 909849-01-0) was reacted with tert-butyl 3-bromoazetidine-1-carboxylate to give the title compound as light yellow waxy solid. MS (ESI): m/z=411.2 [M+H]⁺.

Step b) 5-(Azetidin-3-yl)-2-(4-(trifluoromethoxy)phenoxy)pyridine 4-methylbenzenesulfonate In analogy to the procedure described in example 48 b, tert-butyl 3-(6-(4-(trifluoromethoxy)phenoxy)pyridin-3-yl)azetidine-1-carboxylate was reacted with 4-methylbenzenesulfonic acid hydrate to obtain the title compound as white crystals. MS (ESI): m/z=311.1 [M+H]⁺.

Example 50

(4aR,8aS)-6-(3-(6-(4-Chlorophenoxy)pyridin-3-yl)azetidine-1-carbonyl)hexahydro-2H-pyrido[4,3-b][1,4]oxazin-3(4H)-one

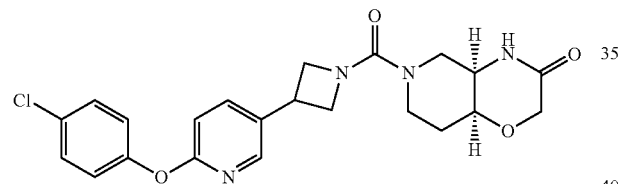

In analogy to the procedure described in example 48, (4aR,8aS)-hexahydro-2H-pyrido[4,3-b][1,4]oxazin-3(4H)-one (2S,3S)-2,3-bis((4-methylbenzoyl)oxy)succinate was reacted with 5-(azetidin-3-yl)-2-(4-chlorophenoxy)pyridine 4-methylbenzenesulfonate to obtain the title compound as white foam. MS (ESI): m/z=443.2 [M+H]⁺.

Step a) tert-Butyl 3-(6-(4-chlorophenoxy)pyridin-3-yl)azetidine-1-carboxylate

In analogy to the procedure described in example 48 a, 5-bromo-2-(4-chlorophenoxy)pyridine (CAS RN 28231-69-8) was reacted with tert-butyl 3-bromoazetidine-1-carboxylate to give the title compound as off-white solid. MS (ESI): m/z=361.2 [M+H]⁺.

Step b) 5-(Azetidin-3-yl)-2-(4-chlorophenoxy)pyridine 4-methylbenzenesulfonate

In analogy to the procedure described in example 48 b, tert-butyl 3-(6-(4-chlorophenoxy)pyridin-3-yl)azetidine-1-carboxylate was reacted with 4-methylbenzenesulfonic acid hydrate to obtain the title compound as white crystals. MS (ESI): m/z=261.1 [M+H]⁺.

Example 51

(4aR,8aS)-6-[3-[4-(3,6-Dimethylpyridazin-4-yl)oxyphenyl]azetidine-1-carbonyl]-4,4a,5,7,8,8a-hexahydropyrido[4,3-b][1,4]oxazin-3-one

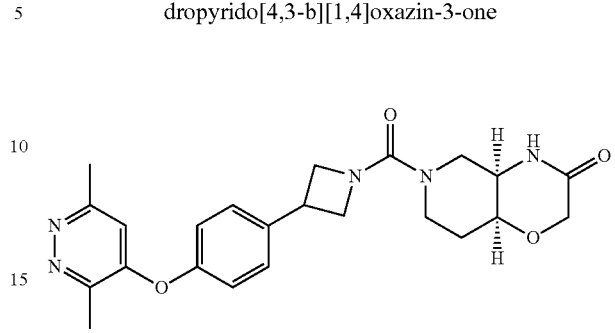

A mixture of (4aR,8aS)-6-(3-(4-hydroxyphenyl)azetidine-1-carbonyl)hexahydro-2H-pyrido[4,3-b][1,4]oxazin-3(4H)-one (50 mg, 151 μmol, BB3), 4-chloro-3,6-dimethylpyridazine (23.7 mg, 166 μmol, CAS RN 68206-05-3) and K₂C₀₃ (41.7 mg, 302 μmol) in DMSO (0.5 mL) was stirred in a sealed tube for 14 h at ambient temperature and purified by reverse phase flash chromatography to give the title compound (20 mg, 30%) as off-white solid. MS (ESI): m/z=438.3 [M+H]⁺.

Example 52

(4aR,8aS)-6-(3-(6-(2-Chlorophenoxy)pyridin-3-yl)azetidine-1-carbonyl)hexahydro-2H-pyrido[4,3-b][1,4]oxazin-3(4H)-one

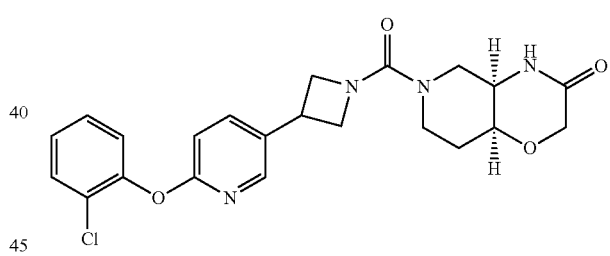

In analogy to the procedure described in example 48, (4aR,8aS)-hexahydro-2H-pyrido[4,3-b][1,4]oxazin-3(4H)-one (2S,3S)-2,3-bis((4-methylbenzoyl)oxy)succinate was reacted with 5-(azetidin-3-yl)-2-(2-chlorophenoxy)pyridine 4-methylbenzenesulfonate to obtain the title compound as off-white solid. MS (ESI): m/z=443.3 [M+H]⁺.

Step a) tert-Butyl 3-(6-(2-chlorophenoxy)pyridin-3-yl)azetidine-1-carboxylate

In analogy to the procedure described in example 48 a, 5-bromo-2-(2-chlorophenoxy)pyridine (CAS RN 1240670-82-9) was reacted with tert-butyl 3-bromoazetidine-1-carboxylate to give the title compound as yellow oil. MS (ESI): m/z=361.2 [M+H]⁺.

Step b) 5-(Azetidin-3-yl)-2-(2-chlorophenoxy)pyridine 4-methylbenzenesulfonate

In analogy to the procedure described in example 48 b, tert-butyl 3-(6-(2-chlorophenoxy)pyridin-3-yl)azetidine-1- carboxylate was reacted with 4-methylbenzenesulfonic acid hydrate to obtain the title compound as white crystals. MS (ESI): m/z=261.1 [M+H]$^+$.

Example 53

(4aR,8aS)-6-(3-(6-(3-Chlorophenoxy)pyridin-3-yl)azetidine-1-carbonyl)hexahydro-2H-pyrido[4,3-b][1,4]oxazin-3(4H)-one

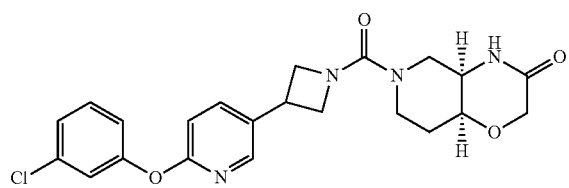 [SMILES: O=C1CO[C@H]2CCN(C(=O)N3CC(c4ccc(Oc5cccc(Cl)c5)nc4)C3)C[C@H]2N1]

In analogy to the procedure described in example 48, (4aR,8aS)-hexahydro-2H-pyrido[4,3-b][1,4]oxazin-3(4H)-one (2S,3S)-2,3-bis((4-methylbenzoyl)oxy)succinate was reacted with 5-(azetidin-3-yl)-2-(3-chlorophenoxy)pyridine 4-methylbenzenesulfonate to obtain the title compound as off-white solid. MS (ESI): m/z=443.3 [M+H]$^+$.

Step a) tert-Butyl 3-(6-(3-chlorophenoxy)pyridin-3-yl)azetidine-1-carboxylate

In analogy to the procedure described in example 48 a, 5-bromo-2-(3-chlorophenoxy)pyridine (CAS RN 1240670-82-9) was reacted with tert-butyl 3-bromoazetidine-1-carboxylate to give the title compound as off-white solid. MS (ESI): m/z=361.2 [M+H]$^+$.

Step b) 5-(Azetidin-3-yl)-2-(3-chlorophenoxy)pyridine 4-methylbenzenesulfonate

In analogy to the procedure described in example 48 b, tert-butyl 3-(6-(3-chlorophenoxy)pyridin-3-yl)azetidine-1-carboxylate was reacted with 4-methylbenzenesulfonic acid hydrate to obtain the title compound as white crystals. MS (ESI): m/z=261.2 [M+H]$^+$.

Example 54

(4aR,8aS)-6-[4-[4-(4-Fluorophenoxy)phenyl]piperidine-1-carbonyl]-4,4a,5,7,8,8a-hexahydropyrido[4,3-b][1,4]oxazin-3-one

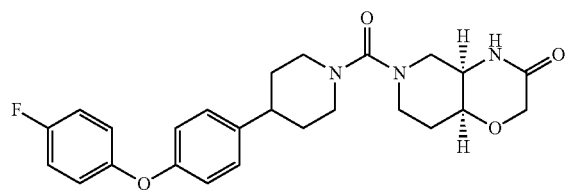 [SMILES: O=C1CO[C@H]2CCN(C(=O)N3CCC(c4ccc(Oc5ccc(F)cc5)cc4)CC3)C[C@H]2N1]

A mixture of (4-nitrophenyl) (4aR,8aS)-3-oxo-4,4a,5,7,8,8a-hexahydropyrido[4,3-b][1,4]oxazine-6-carboxylate (90.1 mg, 0.280 mmol, BB2a), DIPEA (362.1 mg, 2.8 mmol) and 4-[4-(4-fluorophenoxy)phenyl]piperidine; 2,2,2-trifluoroacetic acid (50 mg, 0.130 mmol, TFA salt of CAS RN 224449-70-1) in ACN (1 mL) was stirred at 80° C. for 12 h. The reaction mixture was brought to dryness under reduced pressure. The residue was purified by prep. HPLC (0.225% TFA) and lyophilized to give the title compound (19.6 mg, 0.040 mmol, 32.5% yield) as yellow solid. MS (ESI): m/z=454.4 [M+H]$^+$.

Example 55

(4aR,8aS)-6-[3-Hydroxy-3-(4-phenoxyphenyl)azetidine-1-carbonyl]-4,4a,5,7,8,8a-hexahydropyrido[4,3-b][1,4]oxazin-3-one

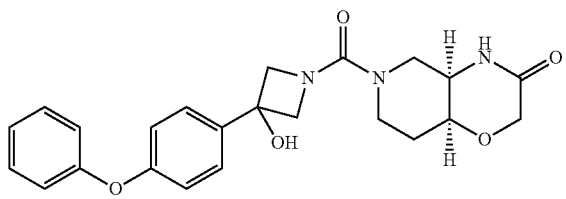

In analogy to the procedure described in example 47, (4-nitrophenyl) (4aR,8aS)-3-oxo-4,4a,5,7,8,8a-hexahydropyrido[4,3-b][1,4]oxazine-6-carboxylate was reacted with 3-(4-phenoxyphenyl)azetidin-3-ol; 2,2,2-trifluoroacetic acid (TFA salt of CAS RN 2229540-84-3) to give the title compound as white solid. MS (ESI): m/z=424.1 [M+H]$^+$.

Example 56

(4aR,8aS)-6-[3-Hydroxy-3-(5-phenoxy-2-pyridyl)azetidine-1-carbonyl]-4,4a,5,7,8,8a-hexahydropyrido[4,3-b][1,4]oxazin-3-one

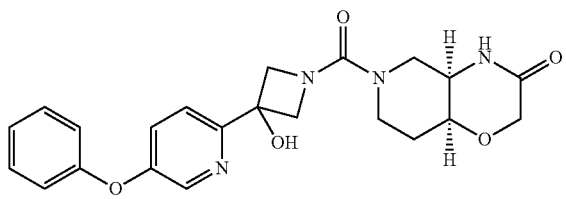 [SMILES: O=C1CO[C@H]2CCN(C(=O)N3CC(O)(c4ccc(Oc5ccccc5)cn4)C3)C[C@H]2N1]

In analogy to the procedure described in example 47, (4-nitrophenyl) (4aR,8aS)-3-oxo-4,4a,5,7,8,8a-hexahydropyrido[4,3-b][1,4]oxazine-6-carboxylate was reacted with 3-(5-phenoxy-2-pyridyl)azetidin-3-ol; 2,2,2-trifluoroacetic acid (TFA salt of CAS RN 2355937-31-2) to give the title compound as light yellow solid. MS (ESI): m/z=425.3 [M+H]$^+$.

Example 57

(4aR,8aS)-6-[4-(4-Phenoxyphenyl)piperidine-1-carbonyl]-4,4a,5,7,8,8a-hexahydropyrido[4,3-b][1,4]oxazin-3-one

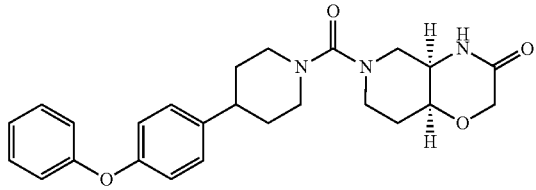 [SMILES: O=C1CO[C@H]2CCN(C(=O)N3CCC(c4ccc(Oc5ccccc5)cc4)CC3)C[C@H]2N1]

In analogy to the procedure described in example 47, (4-nitrophenyl) (4aR,8aS)-3-oxo-4,4a,5,7,8,8a-hexahydropyrido[4,3-b][1,4]oxazine-6-carboxylate was reacted with 4-(4-phenoxyphenyl)piperidine; 2,2,2-trifluoroacetic acid (CAS RN 1247029-36-2) to give the title compound as white solid. MS (ESI): m/z=436.1 [M+H]$^+$.

Example 58

(4aR,8aS)-6-[4-(4-Phenoxyphenyl)piperazine-1-carbonyl]-4,4a,5,7,8,8a-hexahydropyrido[4,3-b][1,4]oxazin-3-one

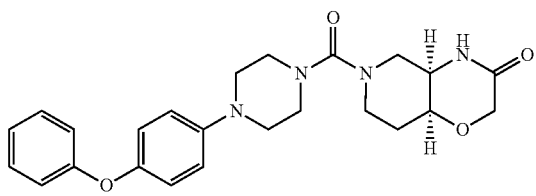 [SMILES: O=C1CO[C@H]2CCN(C(=O)N3CCN(c4ccc(Oc5ccccc5)cc4)CC3)C[C@H]2N1]

In analogy to the procedure described in example 47, (4-nitrophenyl) (4aR,8aS)-3-oxo-4,4a,5,7,8,8a-hexahydropyrido[4,3-b][1,4]oxazine-6-carboxylate was reacted with 1-(4-phenoxyphenyl)piperazine; 2,2,2-trifluoroacetic acid (TFA salt of CAS RN 62755-61-7) to give the title compound as light red solid. MS (ESI): m/z=437.3 [M+H]$^+$.

Synthesis of Building Blocks
BB1a & BB1b (+)-cis-4a,5,6,7,8,8a-Hexahydro-4H-pyrido[4,3-b][1,4]oxazin-3-one and (−)-cis-4a,5,6,7,8,8a-Hexahydro-4H-pyrido[4,3-b][1,4]oxazin-3-one BB1a(+)

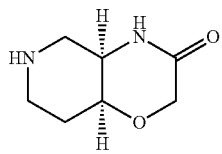

BB1b(−)

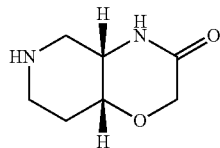

The enantiomers of rac-(4aR,8aS)-hexahydro-2H-pyrido[4,3-b][1,4]oxazin-3(4H)-one dihydrochloride (BB1, 500 mg, 2.18 mmol, ChemBridge Corporation) were separated by preparative chiral HPLC (ReprosilChiral NR column) using an isocratic mixture of EtOH (containing 0.05% of NH$_4$OAc):n-heptane (30:70).

First eluting enantiomer: (+)-cis-4a,5,6,7,8,8a-Hexahydro-4H-pyrido[4,3-b][1,4]oxazin-3-one (BB1a). Yellow solid (0.150 g; 44.0%). MS (ESI): m/z=157.1 [M+H]$^+$.

Second eluting enantiomer: (−)-cis-4a,5,6,7,8,8a-Hexahydro-4H-pyrido[4,3-b][1,4]oxazin-3-one. (BB1b). Yellow solid (0.152 g; 44.6%). MS (ESI): m/z=157.1 [M+H]$^+$.

BB2a and BB2b

4-Nitrophenyl (4aR,8aS)-3-oxohexahydro-2H-pyrido[4,3-b][1,4]oxazine-6(5H)-carboxylate (BB2a)

and 4-nitrophenyl (4aS,8aR)-3-oxohexahydro-2H-pyrido[4,3-b][1,4]oxazine-6(5H)-carboxylate (BB2b)

BB2a
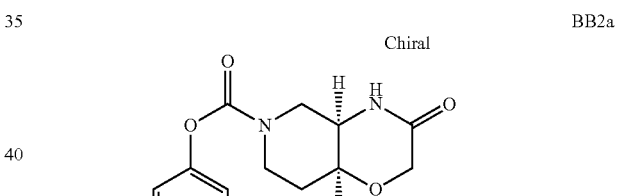

BB2b
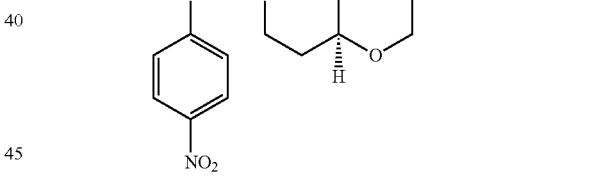

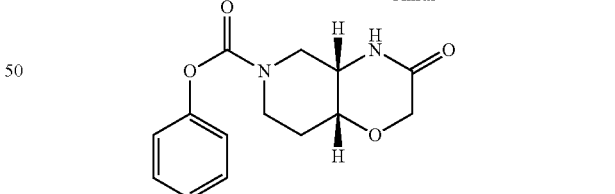

To a suspension of rac-(4aR,8aS)-hexahydro-2H-pyrido[4,3-b][1,4]oxazin-3(4H)-one; dihydrochloride salt (4.5 g, 19.6 mmol, BB1) in dry DCM (125 mL) at 0° C. was added DIPEA (6.35 g, 8.58 mL, 49.1 mmol) followed by 4-nitrophenyl carbonochloridate (4.35 g, 21.6 mmol). The reaction mixture was stirred at 0° C. for 10 min and at RT for 2 hours. The crude reaction was diluted with DCM and transferred into a separating funnel for extraction with sat. aq. Na$_2$CO$_3$ solution. The organic phase was collected and the aqueous phase was back-extracted with DCM. The combined organic phases were dried over Na₂SO₄ and evaporated down to dryness to yield 6.62 g of a crude racemic product (BB7) as a yellow solid. The crude material was directly submitted for a chiral SFC separation to yield enantiomer BB2b (2.72 g, second eluting enantiomer) as a yellow solid and enantiomer BB2a (3.25 g, first eluting enantiomer) as a light beige solid but contaminated with BB2b. A further SFC chiral separation was carried out to yield 2.71 g of BB2a. MS (ESI): m/z=322.2 [M+H]⁺ for both enantiomers.

BB3

(4aR,8aS)-6-[3-(4-Hydroxyphenyl)azetidine-1-carbonyl]-4,4a,5,7,8,8a-hexahydropyrido[4,3-b][1,4]oxazin-3-one

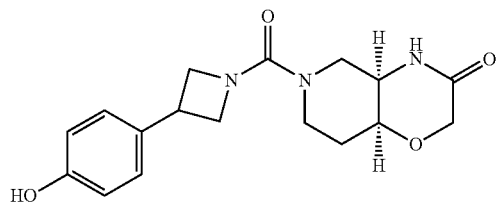 [SMILES: O=C1CO[C@H]2CCN(C(=O)N3CC(c4ccc(O)cc4)C3)C[C@H]2N1]

To a solution of (4-nitrophenyl) (4aR,8aS)-3-oxo-4,4a,5,7,8,8a-hexahydropyrido[4,3-b][1,4]oxazine-6-carboxylate (BB2a, 1.22 g, 3.8 mmol) and 4-(azetidin-3-yl)phenol trifluoroacetate salt (1 g, 3.8 mmol) in ACN (10 mL) was added DIPEA (4.91 g, 37.99 mmol) and the reaction mixture heated to 80° C. for 12 hours. The solution was evaporated to dryness and the residue was taken up in ACN (20 mL). The resulting solid precipitate was filtered, washed with ACN and further dried to give the title compound (0.65 g, 51.6%) as off-white solid. MS (ESI): m/z=332.1 [M+H]⁺.

Step a) tert-Butyl 3-(4-hydroxyphenyl)azetidine-1-carboxylate

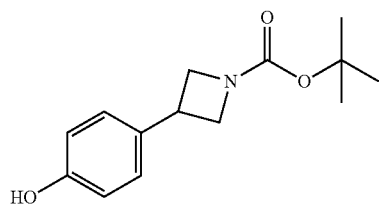 [SMILES: CC(C)(C)OC(=O)N1CC(c2ccc(O)cc2)C1]

To a solution of 4-bromophenol (3.6 g, 21.18 mmol, CAS RN 106-41-2), tert-butyl 3-bromoazetidine-1-carboxylate (5 g, 21.18 mmol, CAS RN 1064194-10-0), Ir[dF(CF₃)ppy]₂(dtbbpy)PF₆ (0.237 g, 0.210 mmol), NiCl₂-glyme (0.023 g, 0.110 mmol), 4-tert-butyl-2-(4-tert-butyl-2-pyridyl)pyridine (0.034 g, 0.130 mmol), bis(trimethylsilyl)silyl-trimethylsilane (5.26 g, 21.18 mmol) and Na₂CO₃ (4.49 g, 42.35 mmol) in DME (100 mL). The reaction mixture was stirred and irradiated with a 34 W blue LED lamp (7 cm away), with cooling fan to keep the reaction temperature at 25° C. for 14 hours. The reaction was filtered, the filtrate evaporated and purified by preparative HPLC to give the title compound (1.8 g, 34%) as light yellow solid. MS (ESI): m/z=194.0 [M+H-56]⁺.

Step b) 4-(Azetidin-3-yl)phenol; trifluoroacetate salt

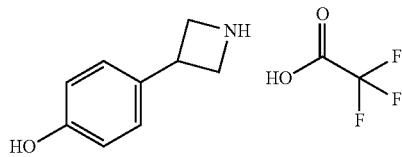 [SMILES: Oc1ccc(C2CNC2)cc1 ; O=C(O)C(F)(F)F]

To a solution of tert-butyl 3-(4-hydroxyphenyl)azetidine-1-carboxylate (1 g, 4.01 mmol) in DCM (30 mL) was added TFA (5.0 mL) and the reaction mixture was stirred at room temperature for 12 hours. The mixture was evaporated in vacuo to give the crude title compound (1 g, 94.7% yield) as yellow oil. MS (ESI): m/z=150.1 [M+H]⁺.

BB4

[4-[1-[(4aR,8aS)-3-Oxo-4,4a,5,7,8,8a-hexahydropyrido[4,3-b][1,4]oxazine-6-carbonyl]azetidin-3-yl]phenyl]boronic acid

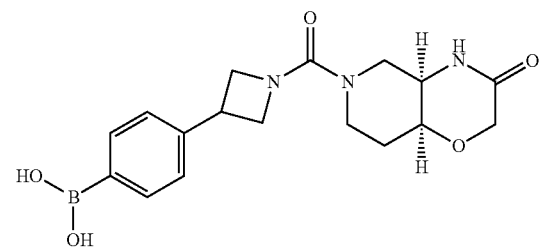 [SMILES: O=C1CO[C@H]2CCN(C(=O)N3CC(c4ccc(B(O)O)cc4)C3)C[C@H]2N1]

To a solution of (4aR,8aS)-6-(3-(4-(4,4,5,5-tetramethyl-1,3,2-dioxaborolan-2-yl)phenyl)azetidine-1-carbonyl)hexahydro-2H-pyrido[4,3-b][1,4]oxazin-3(4H)-one (0.2 g, 0.453 mmol) in H₂O (1.2 mL) and acetone (2.4 mL) was added NaIO₄ (0.29 g, 1.36 mmol) and NH₄OAc (0.21 g, 2.72 mmol) at room temperature. Then, the reaction mixture was stirred at 30° C. for 16 hours. The mixture was extracted with EtOAc (3×10 mL), the combined organic layers were dried over Na₂SO₄, filtered and concentrated in vacuo to give the crude title compound (0.176 g) as white solid. MS (ESI): m/z=360.2 [M+H]⁺.

Step a) tert-Butyl 3-(4-bromophenyl)azetidine-1-carboxylate

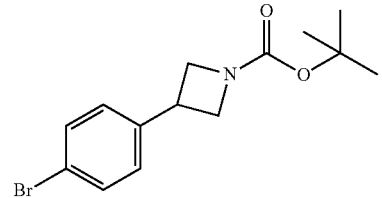 [SMILES: CC(C)(C)OC(=O)N1CC(c2ccc(Br)cc2)C1]

To a solution of tert-butyl 3-iodoazetidine-1-carboxylate (3.0 g, 10.6 mmol, CAS RN 254454-54-1) in 2-propanol (30 mL) was added a solution of 4-bromophenylboronic acid (4.26 g, 21.19 mmol, CAS RN 5467-74-3) in 2-propanol (15 mL) at room temperature. Then, rac-(1R,2R)-2-aminocyclohexan-1-ol (73.18 mg, 0.640 mmol), a 1M solution of sodium bis(trimethylsilyl)amide in THF (21.19 mL, 21.19 mmol) and nickel(II) iodide (198.69 mg, 0.640 mmol) were added to the mixture which was stirred at room temperature for 30 min. The mixture was transferred into 10 sealed tubes and heated under microwave irradiation at 80° C. for 30 min. The mixtures were combined, diluted with water (100 mL) and extracted with ethyl acetate (3×40 mL). The combined organic layer was washed with brine, dried over sodium sulfate, filtered and concentrated in vacuo. The residue was then purified by MPLC to yield the title compound (2.8 g, 84.6%) as yellow oil. MS (ESI): m/z=256.0 [M+H-56]+.

Step b) 3-(4-Bromophenyl)azetidine; trifluoroacetate salt

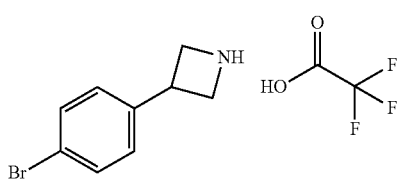 [SMILES: Brc1ccc(C2CNC2)cc1 ; O=C(O)C(F)(F)F]

To a solution of tert-butyl 3-(4-bromophenyl)azetidine-1-carboxylate (2.7 g, 8.65 mmol) in DCM (50 mL) was added TFA (8.0 mL) and the reaction mixture was stirred at room temperature for 12 hours. The mixture was evaporated to dryness to give the crude title compound (2.8 g, 99.3%) as yellow oil. MS (ESI): m/z=214.0 [M+H]+.

Step c) (4aR,8aS)-6-[3-(4-Bromophenyl)azetidine-1-carbonyl]-4,4a,5,7,8,8a-hexahydropyrido[4,3-b][1,4]oxazin-3-one

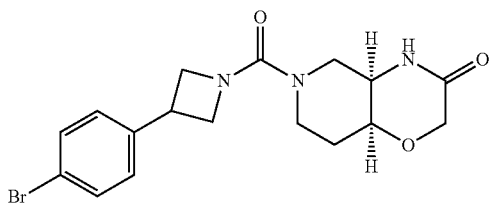 [SMILES: O=C1CO[C@H]2CCN(C(=O)N3CC(c4ccc(Br)cc4)C3)C[C@H]2N1]

To a solution of (4-nitrophenyl) (4aR,8aS)-3-oxo-4,4a,5,7,8,8a-hexahydropyrido[4,3-b][1,4]oxazine-6-carboxylate (BB2a, 2.36 g, 7.36 mmol) and 3-(4-bromophenyl)azetidine trifluoroacetate salt (2 g, 6.13 mmol) in ACN (20 mL) was added DIPEA (7.92 g, 61.33 mmol) and the reaction mixture heated to 80° C. for 12 hours. The mixture was evaporated to dryness and the residue purified by preparative HPLC to give the title compound (1.1 g, 45.5%) as yellow gum. MS (ESI): m/z=396.1 [M+2+H]+.

Step d) (4aR,8aS)-6-(3-(4-(4,4,5,5-Tetramethyl-1,3,2-dioxaborolan-2-yl)phenyl)azetidine-1-carbonyl)hexahydro-2H-pyrido[4,3-b][1,4]oxazin-3(4H)-one

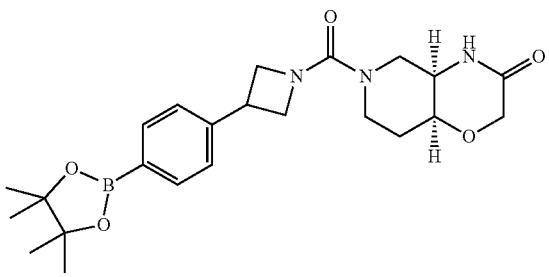 [SMILES: CC1(C)OB(c2ccc(C3CN(C(=O)N4CC[C@@H]5OCC(=O)N[C@@H]5C4)C3)cc2)OC1(C)C]

In a sealed tube, bis(pinacolato)diboron (0.97 g, 3.8 mmol), KOAc (0.747 g, 7.61 mmol) and (4aR,8aS)-6-[3-(4-bromophenyl)azetidine-1-carbonyl]-4,4a,5,7,8,8a-hexahydropyrido[4,3-b][1,4]oxazin-3-one (1 g, 2.54 mmol) were mixed in dioxane (20 mL). Then, PdCl$_2$(dppf)·CH$_2$Cl$_2$ (0.207 g, 0.250 mmol) was added, the reaction mixture purged with N$_2$ and heated to 90° C. for 12 hours. The mixture was filtered, the filtrate evaporated and the residue purified by preparative HPLC to yield the title compound (0.65 g, 58%) as a 3/2 mixture of boronic acid/boronic ester as light brown solid. MS (ESI): m/z=442.1 [M+H]+.

Example 59

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example 60

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound of formula (I):

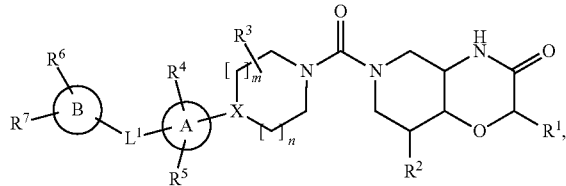

or pharmaceutically acceptable salts thereof, wherein:
A is selected from $C_6$-$C_{14}$-aryl, 5- to 14-membered heteroaryl and 3- to 14-membered heterocyclyl;
B is:
(i) $C_6$-$C_{14}$-aryl; and L is —O—; or
(ii) 5- to 14-membered heteroaryl; and L is a covalent bond or —O—;
m is 0, n is 0 or 1 and X is $CR^8$; or
m is 1, n is 1 or 2 and X is $CR^8$ or N;
$R^1$, $R^2$, and $R^3$ are independently selected from hydrogen and $C_{1-6}$-alkyl;
$R^4$, $R^5$, $R^6$ and $R^7$ are independently selected from hydrogen, halogen, cyano, hydroxy, $C_{1-6}$-alkoxy, halo-$C_{1-6}$-alkoxy, amino-$C_{1-6}$-alkoxy, $C_{1-6}$-alkyl, halo-$C_{1-6}$-alkyl, hydroxy-$C_{1-6}$-alkyl, $C_{1-6}$-alkylsulfonyl, $SF_5$, carbamoyl, $C_{3-10}$-cycloalkyl-$C_{1-6}$-alkoxy-, $C_{1-6}$-alkyl-NH—C(O)—, $C_{1-6}$-alkyl-C(O)—NH—, and $C_{3-10}$-cycloalkyl, wherein each $C_{3-10}$-cycloalkyl is optionally substituted with 1-2 substituents selected from $C_{1-6}$-alkyl and halo-$C_{1-6}$-alkyl; and
$R^8$ is selected from hydrogen, halogen, hydroxy, halo-$C_{1-6}$-alkyl, and $C_{1-6}$-alkyl.

2. The compound of claim 1, or a pharmaceutically acceptable salt thereof, wherein A is $C_6$-$C_{14}$-aryl or 5- to 14-membered heteroaryl, and $R^4$ and $R^5$ are both hydrogen.

3. The compound of claim 1, or a pharmaceutically acceptable salt thereof, wherein A is phenyl or pyridyl, and $R^4$ and $R^5$ are both hydrogen.

4. The compound of claim 1, or a pharmaceutically acceptable salt thereof, wherein
B is:
(i) phenyl; and $L^1$ is —O—; or
(ii) oxadiazolyl, pyridazinyl, pyridyl, or thiazolyl; and $L^1$ is a covalent bond or —O—.

5. The compound of claim 1, or a pharmaceutically acceptable salt thereof, wherein:
m is 1, n is 1, and X is $CR^8$ or N;
and $R^4$ and $R^5$ are both hydrogen.

6. The compound claim 1, or a pharmaceutically acceptable salt thereof, wherein:
m is 0, n is 0, and X is $CR^8$;
and $R^4$ and $R^5$ are both hydrogen.

7. The compound of claim 1, or a pharmaceutically acceptable salt thereof, wherein $R^1$, $R^2$, and $R^3$ are each hydrogen.

8. The compound of claim 1, or a pharmaceutically acceptable salt thereof, wherein the compound of formula (I) is a compound of formula (IIb):

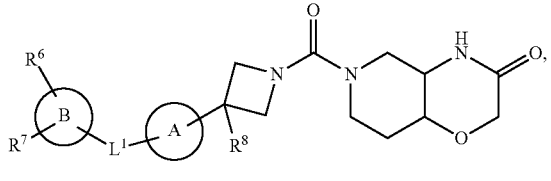

or a pharmaceutically acceptable salt thereof, wherein:
A is phenyl or pyridyl;
B is
(i) phenyl; and $L^1$ is —O—; or
(ii) selected from oxadiazolyl, pyridazinyl, pyridyl, and thiazolyl; and $L^1$ is a covalent bond or —O—;
$R^6$ is selected from hydrogen, fluoro, chloro, cyano, methyl, and 2,2-dimethylpropyl;
$R^7$ is selected from hydrogen, methyl, and fluoro; and
$R^8$ is selected from hydrogen and hydroxy.

9. The compound of claim 1, or a pharmaceutically acceptable salt thereof, wherein:
A is phenyl or pyridyl;
$R^4$ and $R^5$ are both hydrogen;
B is phenyl;
$L^1$ is —O—;
m and n are both 1;
X is $CR^8$ or N;
$R^6$ is hydrogen or halogen; and
$R^7$ and $R^8$ are hydrogen.

10. The compound of claim 1, or a pharmaceutically acceptable salt thereof, wherein
B is:
(i) phenyl; and $L^1$ is —O—; or
(ii) oxadiazolyl, pyridazinyl, pyridyl, or thiazolyl; and $L^1$ is a covalent bond or —O—;
m is 0, n is 0, and X is $CR^8$; or m is 1, n is 1, and X is $CR^8$ or N;
$R^4$ and $R^5$ are both hydrogen;
$R^6$ is hydrogen, halogen, cyano, or $C_{1-6}$-alkyl; and
$R^7$ is hydrogen, halogen, or $C_{1-6}$-alkyl.

11. The compound claim 1, or a pharmaceutically acceptable salt thereof, wherein:
$R^1$, $R^2$, $R^3$, $R^4$, and $R^5$ are each hydrogen;
$R^6$ is hydrogen, halogen, cyano, or $C_{1-6}$-alkyl;
$R^7$ is hydrogen, halogen, or $C_{1-6}$-alkyl; and
$R^8$ is hydrogen or hydroxy.

12. The compound of claim 1, wherein the compound is:
(4aR,8aS)-6-(3-(4-Phenoxyphenyl)azetidine-1-carbonyl) hexahydro-2H-pyrido[4,3-b][1,4]oxazin-3(4H)-one;
(4aR,8aS)-6-[3-[4-(2-Chlorophenoxy)phenyl]azetidine-1-carbonyl]-4,4a,5,7,8,8a-hexahydropyrido[4,3-b][1,4]oxazin-3-one;
(4aR,8aS)-6-[3-(4-Pyrimidin-2-yloxyphenyl)azetidine-1-carbonyl]-4,4a,5,7,8,8a-hexahydropyrido[4,3-b][1,4]oxazin-3-one;
(4aR,8aS)-6-[3-[4-[(2-Methyl-3-pyridyl)oxy]phenyl]azetidine-1-carbonyl]-4,4a,5,7,8,8a-hexahydropyrido[4,3-b][1,4]oxazin-3-one;
(4aR,8aS)-6-[3-[4-(4-Methylpyrimidin-2-yl)oxyphenyl]azetidine-1-carbonyl]-4,4a,5,7,8,8a-hexahydropyrido[4,3-b][1,4]oxazin-3-one;
(4aR,8aS)-6-[3-(4-Pyridazin-3-yloxyphenyl)azetidine-1-carbonyl]-4,4a,5,7,8,8a-hexahydropyrido[4,3-b][1,4]oxazin-3-one;

(4aR,8aS)-6-[3-[4-[(4-Methyl-3-pyridyl)oxy]phenyl]azetidine-1-carbonyl]-4,4a,5,7,8,8a-hexahydropyrido[4,3-b][1,4]oxazin-3-one;
(4aR,8aS)-6-[3-[4-[(5-Fluoro-3-pyridyl)oxy]phenyl]azetidine-1-carbonyl]-4,4a,5,7,8,8a-hexahydropyrido[4,3-b][1,4]oxazin-3-one;
(4aR,8aS)-6-[3-[4-[(5-Chloro-3-pyridyl)oxy]phenyl]azetidine-1-carbonyl]-4,4a,5,7,8,8a-hexahydropyrido[4,3-b][1,4]oxazin-3-one;
(4aR,8aS)-6-[3-[4-(3-Pyridyloxy)phenyl]azetidine-1-carbonyl]-4,4a,5,7,8,8a-hexahydropyrido[4,3-b][1,4]oxazin-3-one;
(4aR,8aS)-6-[3-[4-(4-Methylpyridazin-3-yl)oxyphenyl]azetidine-1-carbonyl]-4,4a,5,7,8,8a-hexahydropyrido[4,3-b][1,4]oxazin-3-one;
(4aR,8aS)-6-[3-[4-(3-Chloropyridazin-4-yl)oxyphenyl]azetidine-1-carbonyl]-4,4a,5,7,8,8a-hexahydropyrido[4,3-b][1,4]oxazin-3-one;
(4aR,8aS)-6-[3-[4-(4-Methoxypyrimidin-2-yl)oxyphenyl]azetidine-1-carbonyl]-4,4a,5,7,8,8a-hexahydropyrido[4,3-b][1,4]oxazin-3-one;
(4aR,8aS)-6-[3-[4 [4-(Trifluoromethyl)pyrimidin-2-yl]oxyphenyl]azetidine-1-carbonyl]-4,4a,5,7,8,8a-hexahydropyrido[4,3-b][1,4]oxazin-3-one;
(4aR,8aS)-6-[3-[4-(3-Fluorophenoxy)phenyl]azetidine-1-carbonyl]-4,4a,5,7,8,8a-hexahydropyrido[4,3-b][1,4]oxazin-3-one;
(4aR,8aS)-6-[3-[4-(4-Fluorophenoxy)phenyl]azetidine-1-carbonyl]-4,4a,5,7,8,8a-hexahydropyrido[4,3-b][1,4]oxazin-3-one;
(4aR,8aS)-6-[3-[4-(2,4-Difluorophenoxy)phenyl]azetidine-1-carbonyl]-4,4a,5,7,8,8a-hexahydropyrido[4,3-b][1,4]oxazin-3-one;
(4aR,8aS)-6-[3-[4-(2-Fluorophenoxy)phenyl]azetidine-1-carbonyl]-4,4a,5,7,8,8a-hexahydropyrido[4,3-b][1,4]oxazin-3-one;
(4aR,8aS)-6-[3-[4-(4-Chlorophenoxy)phenyl]azetidine-1-carbonyl]-4,4a,5,7,8,8a-hexahydropyrido[4,3-b][1,4]oxazin-3-one;
(4aR,8aS)-6-[3-[4-(3-Chlorophenoxy)phenyl]azetidine-1-carbonyl]-4,4a,5,7,8,8a-hexahydropyrido[4,3-b][1,4]oxazin-3-one;
(4aR,8aS)-6-[3-[4-(2-Methylphenoxy)phenyl]azetidine-1-carbonyl]-4,4a,5,7,8,8a-hexahydropyrido[4,3-b][1,4]oxazin-3-one;
(4aR,8aS)-6-[3-[4-[3-(Trifluoromethyl)phenoxy]phenyl]azetidine-1-carbonyl]-4,4a,5,7,8,8a-hexahydropyrido[4,3-b][1,4]oxazin-3-one;
2-[4-[1-[(4aR,8aS)-3-Oxo-4,4a,5,7,8,8a-hexahydropyrido[4,3-b][1,4]oxazine-6-carbonyl]azetidin-3-yl]phenoxy]benzonitrile;
(4aR,8aS)-6-[3-[4-(2-Chloropyrimidin-4-yl)oxyphenyl]azetidine-1-carbonyl]-4,4a,5,7,8,8a-hexahydropyrido[4,3-b][1,4]oxazin-3-one;
(+)-(4aR,8aS)-6-[3-[4-(4-Cyclopropylpyrimidin-2-yl)oxyphenyl]azetidine-1-carbonyl]-4,4a,5,7,8,8a-hexahydropyrido[4,3-b][1,4]oxazin-3-one;
(4aR,8aS)-6-[3-[4-[(6-Methyl-2-pyridyl)oxy]phenyl]azetidine-1-carbonyl]-4,4a,5,7,8,8a-hexahydropyrido[4,3-b][1,4]oxazin-3-one;
(4aR,8aS)-6-[3-[4-[(4-chloro-3-pyridyl)oxy]phenyl]azetidine-1-carbonyl]-4,4a,5,7,8,8a-hexahydropyrido[4,3-b][1,4]oxazin-3-one;
(4aR,8aS)-6-[3-[4-[(3-Fluoro-4-pyridyl)oxy]phenyl]azetidine-1-carbonyl]-4,4a,5,7,8,8a-hexahydropyrido[4,3-b][1,4]oxazin-3-one;
(+)-(4aR,8aS)-6-[3-[4-(2-Methylsulfonylpyrimidin-4-yl)oxyphenyl]azetidine-1-carbonyl]-4,4a,5,7,8,8a-hexahydropyrido[4,3-b][1,4]oxazin-3-one;
(4aR,8aS)-6-[3-[4-[(3,6-Dimethyl-2-pyridyl)oxy]phenyl]azetidine-1-carbonyl]-4,4a,5,7,8,8a-hexahydropyrido[4,3-b][1,4]oxazin-3-one;
(4aR,8aS)-6-[3-[4-(1H-Pyrazol-5-yl)phenyl]azetidine-1-carbonyl]-4,4a,5,7,8,8a-hexahydropyrido[4,3-b][1,4]oxazin-3-one;
(4aR,8aS)-6-[3-[4-[2-(2,2-Dimethylpropyl)pyrazol-3-yl]phenyl]azetidine-1-carbonyl]-4,4a,5,7,8,8a-hexahydropyrido[4,3-b][1,4]oxazin-3-one;
(4aR,8aS)-6-[3-[4-[1-(2,2-Dimethylpropyl)pyrazol-3-yl]phenyl]azetidine-1-carbonyl]-4,4a,5,7,8,8a-hexahydropyrido[4,3-b][1,4]oxazin-3-one;
(4aR,8aS)-6-[3-[4-(3-Chloro-2-pyridyl)phenyl]azetidine-1-carbonyl]-4,4a,5,7,8,8a-hexahydropyrido[4,3-b][1,4]oxazin-3-one;
(4aR,8aS)-6-[3-[4-(2,4-Dimethyloxazol-5-yl)phenyl]azetidine-1-carbonyl]-4,4a,5,7,8,8a-hexahydropyrido[4,3-b][1,4]oxazin-3-one;
(4aR,8aS)-6-[3-[4-(3,5-Dimethylpyrazol-1-yl)phenyl]azetidine-1-carbonyl]-4,4a,5,7,8,8a-hexahydropyrido[4,3-b][1,4]oxazin-3-one;
(4aR,8aS)-6-[3-[4-[3-(2,2-Dimethylpropyl)triazol-4-yl]phenyl]azetidine-1-carbonyl]-4,4a,5,7,8,8a-hexahydropyrido[4,3-b][1,4]oxazin-3-one;
(4aR,8aS)-6-[3-[4-[5-(2,2-Dimethylpropyl)-1,2,4-oxadiazol-3-yl]phenyl]azetidine-1-carbonyl]-4,4a,5,7,8,8a-hexahydropyrido[4,3-b][1,4]oxazin-3-one;
(4aR,8aS)-6-[3-[4-[5-(2,2-Dimethylpropyl)-1,3,4-oxadiazol-2-yl]phenyl]azetidine-1-carbonyl]-4,4a,5,7,8,8a-hexahydropyrido[4,3-b][1,4]oxazin-3-one;
(4aR,8aS)-6-[3-[4-[2-(2-Fluoroethyl)pyrazol-3-yl]phenyl]azetidine-1-carbonyl]-4,4a,5,7,8,8a-hexahydropyrido[4,3-b][1,4]oxazin-3-one;
(4aR,8aS)-6-[3-[4-[1-(2-Fluoroethyl)pyrazol-4-yl]phenyl]azetidine-1-carbonyl]-4,4a,5,7,8,8a-hexahydropyrido[4,3-b][1,4]oxazin-3-one;
(4aR,8aS)-6-[3-[4-(4-Methyl-1,3-thiazol-2-yl)phenyl]azetidine-1-carbonyl]-4,4a,5,7,8,8a-hexahydropyrido[4,3-b][1,4]oxazin-3-one;
(4aR,8aS)-6-[3-[4-(1-Methylpyrazol-3-yl)phenyl]azetidine-1-carbonyl]-4,4a,5,7,8,8a-hexahydropyrido[4,3-b][1,4]oxazin-3-one;
(4aR,8aS)-6-[3-[4-(6-Fluoropyridin-3-yl)phenyl]azetidine-1-carbonyl]-4,4a,5,7,8,8a-hexahydropyrido[4,3-b][1,4]oxazin-3-one;
(4aR,8aS)-6-[3-[4-(2-Fluoropyridin-4-yl)phenyl]azetidine-1-carbonyl]-4,4a,5,7,8,8a-hexahydropyrido[4,3-b][1,4]oxazin-3-one;
(4aR,8aS)-6-[3-[4-(1-Methylpyrazol-4-yl)phenyl]azetidine-1-carbonyl]-4,4a,5,7,8,8a-hexahydropyrido[4,3-b][1,4]oxazin-3-one;
(4aR,8aS)-6-[3-[4-(2-Methylpyrazol-3-yl)phenyl]azetidine-1-carbonyl]-4,4a,5,7,8,8a-hexahydropyrido[4,3-b][1,4]oxazin-3-one;
(4aR,8aS)-6-[3-[5-(4-Fluorophenoxy)-2-pyridyl]azetidine-1-carbonyl]-4,4a,5,7,8,8a-hexahydropyrido[4,3-b][1,4]oxazin-3-one;
(4aR,8aS)-6-(3-(6-(4-Fluorophenoxy)pyridin-3-yl)azetidine-1-carbonyl)hexahydro-2H-pyrido[4,3-b][1,4]oxazin-3(4H)-one;
(4aR,8aS)-6-(3-(6-(4-(Trifluoromethoxy)phenoxy)pyridin-3-yl)azetidine-1-carbonyl)hexahydro-2H-pyrido[4,3-b][1,4]oxazin-3(4H)-one;

(4aR,8aS)-6-(3-(6-(4-Chlorophenoxy)pyridin-3-yl)azeti-dine-1-carbonyl)hexahydro-2H-pyrido[4,3-b][1,4]oxazin-3(4H)-one;

(4aR,8aS)-6-[3-[4-(3,6-Dimethylpyridazin-4-yl)oxyphe-nyl]azetidine-1-carbonyl]-4,4a,5,7,8,8a-hexahydro-pyrido[4,3-b][1,4]oxazin-3-one;

(4aR,8aS)-6-(3-(6-(2-Chlorophenoxy)pyridin-3-yl)azeti-dine-1-carbonyl)hexahydro-2H-pyrido[4,3-b][1,4]oxazin-3(4H)-one;

(4aR,8aS)-6-(3-(6-(3-Chlorophenoxy)pyridin-3-yl)azeti-dine-1-carbonyl)hexahydro-2H-pyrido[4,3-b][1,4]oxazin-3(4H)-one;

(4aR,8aS)-6-[4-[4-(4-Fluorophenoxy)phenyl]piperidine-1-carbonyl]-4,4a,5,7,8,8a-hexahydropyrido[4,3-b][1,4]oxazin-3-one;

(4aR,8aS)-6-[3-Hydroxy-3-(4-phenoxyphenyl)azetidine-1-carbonyl]-4,4a,5,7,8,8a-hexahydropyrido[4,3-b][1,4]oxazin-3-one;

(4aR,8aS)-6-[3-Hydroxy-3-(5-phenoxy-2-pyridyl)azeti-dine-1-carbonyl]-4,4a, 5,7,8,8a-hexahydropyrido[4,3-b][1,4]oxazin-3-one;

(4aR,8aS)-6-[4-(4-Phenoxyphenyl)piperidine-1-carbo-nyl]-4,4a,5,7,8,8a-hexahydropyrido[4,3-b][1,4]oxazin-3-one; or (4aR,8aS)-6-[4-(4-Phenoxyphenyl)piperazine-1-carbo-nyl]-4,4a,5,7,8,8a-hexahydropyrido[4,3-b][1,4]oxazin-3-one;

or a pharmaceutically acceptable salt thereof.

13. A process of manufacturing a compound of claim 1, or a pharmaceutically acceptable salt thereof, comprising:

reacting 4a,5,6,7,8,8a-hexahydro-4H-pyrido[4,3-b][1,4]oxazin-3-ones 1, wherein $R^1$ and $R^2$ are as defined in claim 1,

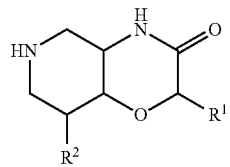

with a heterocyclic amine 2, wherein A, B, $L^1$, X, m, n, and $R^3$ to $R^7$ are as defined in claim 1,

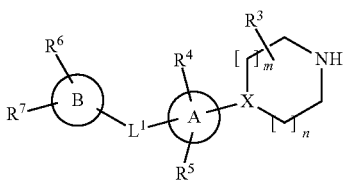

in the presence of a base and a urea forming reagent, to form said compound of claim 1, or a pharmaceutically acceptable salt thereof.

14. A pharmaceutical composition comprising a compound of claim 1, or a pharmaceutically acceptable salt thereof, and a therapeutically inert carrier.

15. A method for the treatment of a disease or disorder in a mammal, the method comprising administering an effective amount of a compound of claim 1, or a pharmaceutically acceptable salt thereof, to the mammal, wherein the disease or disorder is neurodegenerative disease.

16. The method of claim 15, wherein the neurodegenerative disease is multiple sclerosis, Alzheimer's disease, Parkinson's disease, amyotrophic lateral sclerosis, traumatic brain injury, neurotoxicity, stroke, or epilepsy.

17. A pharmaceutical composition comprising a compound of claim 12, or a pharmaceutically acceptable salt thereof, and a therapeutically inert carrier.

* * * * *